(12) United States Patent
Priller et al.

US008895303B2

(10) Patent No.: US 8,895,303 B2
(45) Date of Patent: Nov. 25, 2014

(54) METHOD OF CELL CULTURE AND METHOD OF TREATMENT COMPRISING A VEPO PROTEIN VARIANT

(75) Inventors: Josef Priller, Berlin (DE); Christel Bonnas, Berlin (DE); Andreas Meisel, Berlin (DE)

(73) Assignee: Charite-Universitatsmedizin Berlin, Berlin (DE)

( * ) Notice: Subject to any disclaimer, the term of this patent is extended or adjusted under 35 U.S.C. 154(b) by 1174 days.

(21) Appl. No.: 12/514,773

(22) PCT Filed: Nov. 12, 2007

(86) PCT No.: PCT/EP2007/062235
§ 371 (c)(1),
(2), (4) Date: Jul. 12, 2011

(87) PCT Pub. No.: WO2008/058942
PCT Pub. Date: May 22, 2008

(65) Prior Publication Data
US 2011/0300114 A1     Dec. 8, 2011

(30) Foreign Application Priority Data

Nov. 13, 2006   (EP) .................................. 06023576

(51) Int. Cl.
| | | |
|---|---|---|
| *A61K 31/7088* | (2006.01) | |
| *A61K 31/04* | (2006.01) | |
| *A61K 31/08* | (2006.01) | |
| *A61K 31/10* | (2006.01) | |
| *A61K 31/16* | (2006.01) | |
| *C07K 14/505* | (2006.01) | |
| *C12N 5/00* | (2006.01) | |
| *A61K 38/00* | (2006.01) | |
| *A61K 35/12* | (2006.01) | |

(52) U.S. Cl.
CPC ........... *C07K 14/505* (2013.01); *C12N 2501/14* (2013.01); *A61K 38/00* (2013.01); *A61K 35/12* (2013.01); *C12N 5/0018* (2013.01)
USPC ........ 435/387; 424/93.1; 424/93.2; 424/93.7; 424/94.1; 435/384; 435/455; 536/23.51

(58) Field of Classification Search
USPC ..................... 424/93.1, 93.2, 93.7, 94.1, 387; 435/384, 455; 536/23.51
See application file for complete search history.

(56) References Cited

U.S. PATENT DOCUMENTS

| | | | |
|---|---|---|---|
| 4,704,355 A | 11/1987 | Bernstein | |
| 4,798,824 A | 1/1989 | Belzer et al. | |
| 5,538,362 A | 7/1996 | Akesaka et al. | |
| 2004/0122216 A1* | 6/2004 | Nielsen et al. | 530/351 |

FOREIGN PATENT DOCUMENTS

| | | |
|---|---|---|
| EP | 2 081 956 | 7/2009 |
| WO | WO-91 04014 | 4/1991 |
| WO | WO-91 05867 A1 | 5/1991 |
| WO | WO-94 09257 A1 | 4/1994 |
| WO | WO-95 05465 A1 | 2/1995 |
| WO | WO-97 14307 | 4/1997 |
| WO | WO-99 21966 | 5/1999 |
| WO | WO-00 32772 A2 | 6/2000 |
| WO | WO-01 02017 A2 | 1/2001 |
| WO | WO-01 81405 A2 | 11/2001 |
| WO | WO-03 029291 A2 | 4/2003 |
| WO | WO-2004 011021 A1 | 2/2004 |
| WO | WO-2005 025606 A1 | 3/2005 |
| WO | WO-2007 019545 A2 | 2/2007 |

OTHER PUBLICATIONS

Jaroscak et al, Blood 101:5061-5067, 2003.*
Lin et al, PNAS 82:7580-7584, 1985.*
Wognum et al, Arch. Med. Res. 34:461-475, 2003.*
Altschul, Stephen F. et al., "Basic Local Alignment Search Tool," J. Mol. Biol., 1990, vol. 215, pp. 403-410.
Altschul, Stephen F. et al., "Gapped BLAST and PSI-BLAST: a new generation of protein database search programs," Nucleic Acids Research, 1997, vol. 25, No. 17, pp. 3389-3402.
Arvidsson, Andreas et al., "Neuronal replacement from endogenous precursors in the adult brain after stroke," Nature Medicine, Sep. 2002, vol. 8, No. 9, pp. 963-970.
Blau, H. M. et al., "The Evolving Concept of a Stem Cell: Entity of Function?" Cell, Jun. 29, 2001, vol. 105, pp. 829-841.
Boissel, Jean Paul et al., "Erythropoietin structure-function relationships," The Journal of Biological Chemistry, 1993, vol. 268, No. 21, pp. 15983-15993.
Campana, W. M. et al., "Identification of a neurotrophic sequence in erythropoietin," International Journal of Molecular Medicine, 1998, vol. 1, pp. 235-241.
Chang, L. J. et al., "The molecular genetics of lentiviral vectors—current and future perspectives," Current Gene Therapy, 2001, vol. 1, pp. 237-251.
During, Matthew J. et al., "Controlled Release of Dopamine from a polymeric brain implant: in vivo characterization," Annals of Neurology, Apr. 1989, vol. 25, No. 4, pp. 351-356.
Elliott, S. et al., "Mapping of the Active Site of Recombinant Human Erythropoietin," Blood, Jan. 15, 1997, vol. 89, No. 2, pp. 493-502.
Erbayraktar, Serhat et al., "Asialoerythropoietin is a nonerythropoietic cytokine with broad neuroprotective activity in vivo," PNAS, May 27, 2004, vol. 100, No. 11, pp. 6741-6746.

(Continued)

*Primary Examiner* — Kevin Hill
(74) *Attorney, Agent, or Firm* — Michael A. Whittaker; Acuity Law Group, P.C.

(57) ABSTRACT

In one aspect the present invention is concerned with a method of cell culture, comprising the steps of (i) obtaining a stem or progenitor cell sample, (ii) culturing the stem or progenitor cell sample in media and under closed conditions appropriate to cause proliferation or differentiation of the stem or progenitor cells, wherein the media comprises a vEPO protein variant, (iii) purifying the stem or progenitor cells ex vivo. The invention relates to a method of increasing the number and survival of stem and progenitor cells in vitro and in vivo using a vEPO protein variant. The invention also relates to improved

(56) References Cited

OTHER PUBLICATIONS

Figure 6:
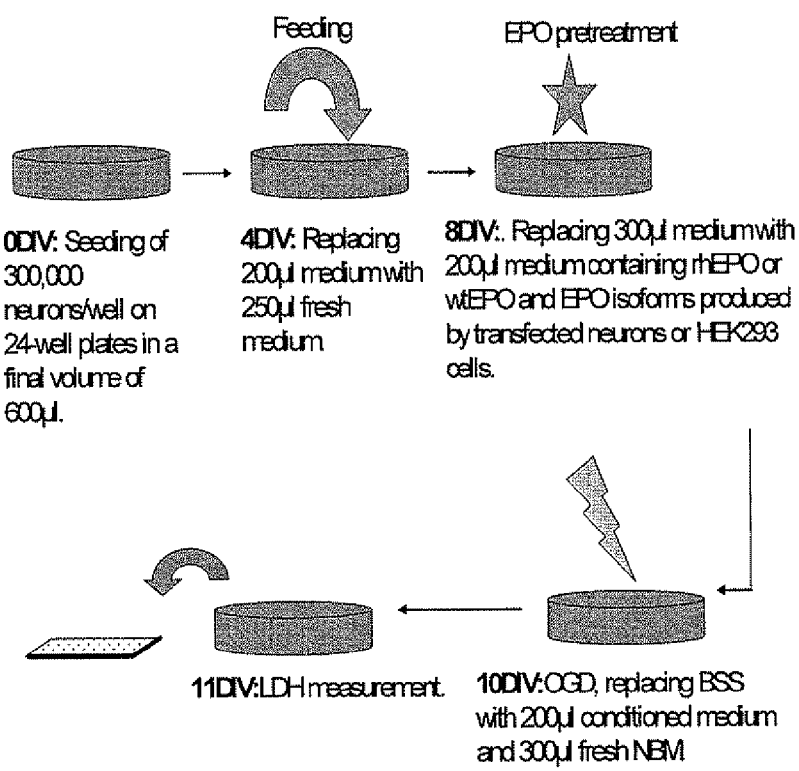

Fibi, Mathias R. et al., "Evidence for the location of the receptor-binding site of human erythropoietin at the Carboxyl-Terminal Domain," Blood, Mar. 15, 1991, vol. 77, No. 6, pp. 1203-1210.

Fidler, I. et al., "Liposomes in the therapy of infectious diseases and cancer," Feb. 16-20, 1988, pp. 244-262.

Gage, Fred H. et al., "Mammalian Neural Stem Cells," Science, Feb. 25, 2000, vol. 287, pp. 1433-1438.

Grodberg, Jennifer et al., "Functional and Structural Role of Arginine 103 in Human Erythropoietin," Archives of Biochemistry and Biophysics, Sep. 15, 1996, vol. 333, No. 2, pp. 471-431.

Grove, Joanna E. et al., "Plasticity of Bone Marrow-Derived Stem Cells," Stem Cells, 2004, vol. 22, pp. 487-500.

Guan, Kaomei et al., "Pluripotency of spermatogonial stem cells from adult mouse testis," Nature Letters, 2006, pp. 1-5.

Hulspas, R. et al., "Characterization of Neurosphere Cell Phenotypes by Flow Cytometry," Cytometry, 2000, vol. 40, pp. 245-250.

International Search Report for PCT/EP2007/062235 dated May 2, 2008.

Jiang, Yuehua et al., "Multipotent progenitor cells can be isolated from postnatal murine bone marrow, muscle, and brain," Experimental Hermatology, 2002, vol. 30, pp. 896-904.

Karlin, Samuel et al., "Applications and statistics for multiple high-scoring segments in molecular sequences," Proc. Natl. Acad. Sci., Jun. 1993, vol. 90, pp. 5873-5877.

Kobinger, G. P. et al., "Filovirus-pseudotyped lentiviral vector can efficiently and stably transducer airway epithelia in vivo," Nature Biotechnology, Mar. 2001, vol. 19, pp. 225-230.

Langer, Robert et al., "New methods of drug delivery," Science, Sep. 28, 1990, vol. 249, pp. 1527-1533.

Leist, Marcel et al., "Derivatives of Erythropoietin that are tissue protective but not erythropoietic," Science, Jul. 9, 2004, vol. 305.

Lindemann, D. et al., "Versatile Retrovirus Vector Systems for Regulated Gene Expression In Vitro and In Vivo," Molecular Medicine, Jul. 1997, vol. 3, No. 7, pp. 466-476.

Park, Mi Hee et al., "ERK-mediated production of neurotrophic factors by astrocytes promotes neuronal stem cell differentiation by erythropoietin," Biochemical and Biophysical Research Communications, 2006, vol. 339, pp. 1021-1028.

Pomerantz, Jason et al., "Nuclear reprogramming: A key to stem cell function in regenerative medicine," Natural Cell Biology, Sep. 2004, vol. 6, No. 9, pp. 810-816.

Recny, Michael A. et al., "Structural Characterization of Natural Human Urinary and Recombinant DNA-derived Erythropoietin," The Journal of Biological Chemistry, Dec. 15, 1987, vol. 262, No. 35, pp. 17156-17163.

Sambrook, Joseph et al., "Molecular Cloning: A Laboratory Manual—Third Ed.," 2001.

Sorokan, S. T. et al., "Erythropoietin mediates increased neurogenesis by embryonic cns stem cells following a modest hypoxic insult," Departments of Anatomy and Pharmacology & Therapetics, 1997, p. 320.

Springer, Matthew L. et al., "VEGF gene delivery to muscle: potential role for vasculogenesis in adults," molecular Cell, Nov. 1998, vol. 2, pp. 549-558.

Tarnowski, M. et al., "Adult stem cells and their ability to differentiate," Med. Sci. Monit., 2006, vol. 12, No. 8.

Weiss, S. et al., "Epidermal growth factor (EGF) and erythropoietin (EPO) stimulate intrinsic brain repair and functional recovery after stroke," Society for Neuroscience, 2003.

* cited by examiner

Fig. 1
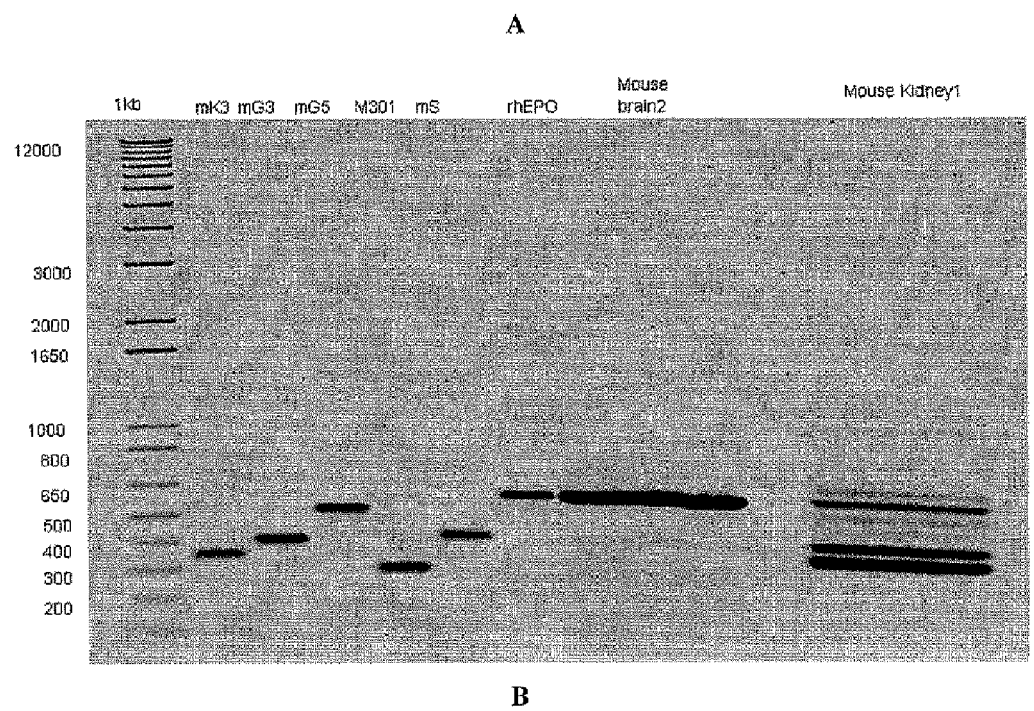
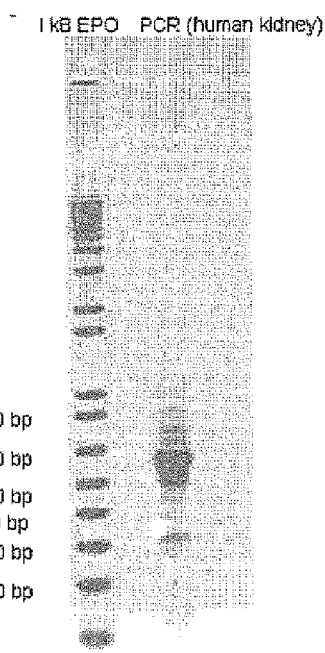

Fig. 2a

```
mEpo    atgggggtgcccgaacgtcccaccctgctgcttttactctccttgctactgattc   55
mS      atgggggtgcccgaacgtcccaccctgctgcttttactctccttgctactgattc   55
mG3     atgggggtgcccgaacgtcccaccctgctgcttttactctccttgctactgattc   55
mG5     atgggggtgcccgaacgtcccaccctgctgcttttactctccttgctactgattc   55
m301    atgggggtgcccgaacgtcccaccctgctgcttttactctccttgctactgattc   55
mK3     atgggggtgcccgaacgtcccaccctgctgcttttactctccttgctactgattc   55 mEpo    ctctgggcctcccagtcctctgtgctcccccacgcctcatctgcgacagtcgagt   110
mS      ctctgggcctcccagtcctctgtgctcccccacgcctcatctgcgacagtcgagt   110
mG3     ctctgggcctcccagtcctctgtgctcccccacgcctcatctgcgacagtcgagt   110
mG5     ctctgggcctcccagtcctctgtgctcccccacgcctcatctgcgacagtcgagt   110
m301    ctctgggcctcccagtcctctgtgctcccccacgcctcatctgcgacagtcgagt   110
mK3     ctctgggcctcccagtcctctgtgctcccccacgcctcatctgcgacagtcgagt   110 mEpo    tctggagaggtacatcttagaggccaaggaggcagaaaatgtcacgatgggttgt   165
mS      tctggagaggtacatcttagaggccaaggaggcagaaaatgtcacgatgggttgt   165
mG3     tctggagaggtacatcttagaggccaaggaggcagaaaatgtcacgatgggttgt   165
mG5     tctggagaggtacatcttagaggccaaggaggcagaaaatgtcacgatgggttgt   165
m301    tctggagaggtacatcttagaggccaaggaggcagaaaatgtcacgatgggttgt   165
mK3     tctggagaggtacatcttagaggccaaggaggcagaaaatgtcacgatgggttgt   165 mEpo    gcagaaggtcccagactgagtgaaaatattacagtcccagataccaaagtcaact   220
mS      gcagaaggtcccagactgagtgaaaatattacagtcccagataccaaagtcaact   220
mG3     gcagaaggtcccagactgagtgaaaatattacagtcccagataccaaagtcaact   220
mG5     gcagaaggtcccagactgagtgaaaatattacagtcccagataccaaagtcaact   220
m301    gcagaaggtcccagactgagtgaaaatattacagtcccagataccaaagtcaact   220
mK3     gcagaaggtcccagactgagtgaaaatattacagtcccagataccaaagtcaact   220 mEpo    tctatgcttggaaaagaatggaggtggaagaacaggccatagaagtttggcaagg   275
mS      tctatgcttggaaaagaatggag--------------------------------   243
mG3     tctatgcttggaaaagaatggaggtggaagaacaggccatagaagtttggcaagg   275
mG5     tctatgcttggaaaagaatggaggtggaagaacaggccatagaagtttggcaagg   275
m301    tc-----------------------------------------------------   222
mK3     tctatgcttggaaaagaatggaggtggaagaacaggccatagaagtttggcaagg   275 mEpo    cctgtccctgctctcagaagccatcctgcaggcccaggccctgctagccaattcc   330
mS      -------------------------------------------------------   -
mG3     cctgtccctgctctcagaagccatcctgcaggcccaggccctgctagccaa----   326
mG5     cctgtccctgctctcagaagccatcctgcaggcccaggccctgctagccaattcc   330
m301    -------------------------------------------------------   -
mK3     cctgtccctgctctcagaagc----------------------------------   296 mEpo    tcccagccaccagagacccttcagcttcatatagacaaagccatcagtggtctac   385
mS      -------------------------------------------------------   -
mG3     -------------------------------------------------------   -
mG5     tcccagccaccagagacccttcagcttcatatagacaaagccatcagtggtctac   385
m301    -------------------------------------------------------   -
mK3     :------------------------------------------------------:  -
```

Fig. 2b

```
mEpo   gtagcctcacttcactgcttcgggtactgggagctcagaaggaattgatgtcgcc   440
mS     ------------------------------------aaggaattgatgtcgcc   260
mG3    ----------------------------------------------------    -
mG5    gtagcctcacttcactgcttcgggtactgggagctcagaaggaattgatgtcgcc   440
m301   ----------------------------------------------------    -
mK3    ----------------------------------------------------    - mEpo   tccagataccaccccacctgctccactccgaacactcacagtggatactttctgc   495
mS     tccagataccaccccacctgctccactccgaacactcacagtggatactttctgc   315
mG3    ----------------------------------------------------    -
mG5    tccagataccaccccacctgctccactccgaacactcacagtggatactttctgc   495
m301   ----------------------------------------------------    -
mK3    ----------------------------------------------------    - mEpo   aagctcttccgggtctacgccaacttcctcggggggaaactgaagctgtacacgg   550
mS     aagctcttccgggtctacgccaacttcctcggggggaaactgaagctgtacacgg   370
mG3    ------------------------cttcctcggggggaaactgaagctgtacacgg   358
mG5    a----------------------------------------------------   496
m301   --------------------------ctccggggggaaactgaagctgtacacgg   250
mK3    --------------------------------------------tgtacacgg   305 mEpo   gagaggtctgcaggagaggggacaggtga   579
mS     gagaggtctgcaggagaggggacaggtga   399
mG3    gagaggtctgcaggagaggggacaggtga   387
mG5    ------------ggagaggggacaggtga   513
m301   gagaggtctgcaggagaggggacaggtga   279
mK3    gagaggtctgcaggagaggggacaggtga*catgctgctgccaccgtggtggaccg*   360 mEpo   ----------------------------------------------------
mK3    *acgaacttgctccccgtcactgtgtcatgccaaccctccaccactcccaaccctc*   415 mEpo   ----------------------------------------------------
mK3    *atcaaacgggtcattaccttcttaccagtctgtcccatggacactccagcaccag*   470 mEpo   ----------------------------------------------------
mK3    *cagtgacatcctcggggccagaagaacttcccagagctccattctgaaatctaaa*   525 mEpo   ----------------------------------------------------
mK3    *gatgtcgctggacaagcccgaggccccagagaagaagagcctcagaatcagctcg*   580 mEpo   ----------------------------------------------------
mK3    *gatttgtttag*   591
```

| | |
|---|---|
| hWT | atgggggtgcacgaatgtcctgctggctgtgcttctcctgctgtgcctcctctgggcctcccagtc |
| hS3 | atgggggtgcacgaatgtcctgctggctgtgcttctcctgctgtgcctcctctgggcctcccagtc |
| h1-4 | atgggggtgcacgaatgtcctgctggctgtgcttctcctgctgtgcctcctctgggcctcccagtc |
| h1-5 | atgggggtgcacgaatgtcctgctggctgtgcttctcctgctgtgcctcctctgggcctcccagtc |
| hS4 | atgggggtgcacgaatgtcctgctggctgtgcttctcctgctgtgcctcctctgggcctcccagtc |
| h1-1 | atgggggtgcacgaatgtcctgctggctgtgcttctcctgctgtgcctcctctgggcctcccagtc |
| h2-1 | atgggggtgcacgaatgtcctgctggctgtgcttctcctgctgtgcctcctctgggcctcccagtc |
| | |
| hWT | ctgggcgcccccaccacgcctcatctgtgacagccagtcctggagaggtacctcttggaggccaaggaggccgag |
| hS3 | ctgggcgcccccaccacgcctcatctgtgacagccagtcctggagaggtacctcttggaggccaaggaggccgag |
| h1-4 | ctgggcgcccccaccacgcctcatctgtgacagccagtcctggagaggtacctcttggaggccaaggaggccgag |
| h1-5 | ctgggcgcccccaccacgcctcatctgtgacagccagtcctggagaggtacctcttggaggccaaggaggccgag |
| hS4 | ctgggcgcccccaccacgcctcatctgtgacagccagtcctggagaggtacctcttggaggccaaggaggccgag |
| h1-1 | ctgggcgcccccaccacgcctcatctgtgacagccagtcctggagaggtacctcttggaggccaaggaggccgag |
| h2-1 | ctgggcgcccccaccacgcctcatctgtgacagccagtcctggagaggtacctcttggaggccaaggaggccgag |
| | |
| Hwt | aatatcacgacgggctgtgctgaacactgcagcttgaatgagaatatcactgtcccagacaccaaagttaatttc |
| hS3 | aatatcacg------------------------------------------------------------------- |
| h1-4 | aatatcacgacgggctgtgctgaacactgcagcttgaatgagaatatcactgtcccagacaccaaagttaatttc |
| h1-5 | aatatcacgacgggctgtgctgaacactgcagcttgaatgagaatatcactgtcccagacaccaaagttaatttc |
| hS4 | aatatcacgacgggctgtgctgaacactgcagcttgaatgagaatatcactgtcccagacaccaaagttaatttc |
| h1-1 | aatatcacgacgggctgtgctgaacactgcagcttgaatgagaatatcactgtccag----------------- |
| h2-1 | aatatcacgacgggctgtgctgaacactgcagcttgaatgagaatatcactgtgacaa---------------- |

FIG.3a

```
hWT    tatgcctggaagaggatggaggtcgggcagcaggccgtagaagtctggcagggcctggccctgctgtcgaagct
hS3    ----------gtcgggcagcaggccgtagaagtctggcagggcctggccctgctgtcgaagct
h1-4   tatgcctggaagaggatggaggtcgggcagcaggcc-----
h1-5   tatgcc-----
hS4    tatgcctggaagaggatggag-----
h1-1   -----
h2-1   ----- hWT    gtcctgcgggccaggccctgttggtcaactcttccagcctgggagcccctgcagctgcatgtggataaagcc
hS3    gtcctgcgggccaggccctgttggtcaactcttccagcctgggagcccctgcagctgcatgtggataaagcc
h1-4   -----ctgttggtcaactcttccagcctgggagcccctgcagctgcatgtggataaagcc
h1-5   -----ctgttggtcaactcttccagcctgggagcccctgcagctgcatgtggataaagcc
hS4    -----cgtgggagcccctgcagctgcatgtggataaagcc
h1-1   -----gccctgttggtcaactcttccagcctgggagcccctgcagctgcatgtggataaagcc
                                418
h2-1   ----- hWT    gtcagtggccttcgcagcctcaccactctgcttcgggctcgcgagcccagaaggaggagccatctccctccagat
hS3    gtcagtggccttcgcagcctcaccactctgcttcgggctcgcgagcccagaaggaggagccatctccctccagat
h1-4   gtcagtggccttcgcagcctcaccactctgcttcgggctcgcgagcccagaaggaggagccatctccctccagat
h1-5   gtcagtggccttcgcagcctcaccactctgcttcgggctcgcgagcccagaaggaggagccatctccctccagat
hS4    gtcagtggccttcgcagcctcaccactctgcttcgggctcgggagcccagaaggaggagccatctccctccagat
h1-1   gtcagtggccttcgcagcctcaccactctgcttcgggctcgggagcccagaaggaggagccatctccctccagat
h2-1   -----
```

FIG.3a (CONTINUED)

```
hWT    gcggcctcagctgctccactccgaacaatcactgctgacactttccgcaaactcttccgagtctactccaatttc
hS3    gcggcctcagctgctccactccgaacaatcactgctgacactttccgcaaactcttccgagtctactccaatttc
h1-4   gcggcctcagctgctccactccgaacaatcactgctgacactttccgcaaactcttccgagtctactccaatttc
h1-5   gcggcctcagctgctccactccgaacaatcactgctgacactttccgcaaactcttccgagtctactccaatttc
hS4    gcggcctcagctgctccactccgaacaatcactgctgacactttccgcaaactcttccgagtctactccaatttc
h1-1   gcggcctcagctgctccactccgaacaatcactgctgacactttccgcaaactcttccgagtctactccaatttc
h2-1   ---------------caatcactgctgacactttccgcaaactcttccgagtctactccaatttc
```

FIG. 3a (CONTINUED)

Fig 3b

```
hWT   ctccggggaaagctgaagctgtacacaggggaggcctgcaggacaggggacagatga
hS3   ctccggggaaagctgaagctgtacacaggggaggcctgcaggacaggggacagatga
h1-4  ctccggggaaagctgaagctgtacacaggggaggcctgcaggacaggggacagatga
h1-5  ctccgggasagctgaagctgtacacaggggaggcctgcaggacaggggacagatga
hS4   ctccgggaaagctgaagctgtacacaggggaggcctgcaggacaggggacagatga
h1-1  ctccggggaaagctgaagctgtacacaggggaggcctgcaggacaggggacagatga
h2-1  ctccggggaaagctgaagctgtacacaggggaggcctgcaggacaggggacagatga
```

Fig. 4

| Helix | | Helix A | | Helix B |
|---|---|---|---|---|
| Affinity | | x xx | x | |

```
hWT   MGVHECPAWLWLLLSLLSLPLGLPVLGAPPRLICDSRVLERYLLEAKEAENITTGCAEHCSLNENITVPDTKVNFYAWKRMEVGQQAVEVWQGLALLSEAVLRGQALLVN
hS3   MGVHECPAWLWLLLSLLSLPLGLPVLGAPPRLICDSRVLERYLLEAKEAENITTGCAEHCSLNENITVPDTKVNFYAWKRMEVGQQAVEVWQGLALLSEAVLRGQALLVN
h1-4  MGVHECPAWLWLLLSLLSLPLGLPVLGAPPRLICDSRVLERYLLEAKEAENIT------------------------------VGQQAVEVWQGLALLSEAVLRGQALLVN
h1-5  MGVHECPAWLWLLLSLLSLPLGLPVLGAPPRLICDSRVLERYLLEAKEAENITTGCAEHCSLNENITVPDTKVNFYAWKRMEVGQQ----------------ALLVN
hS4   MGVHECPAWLWLLLSLLSLPLGLPVLGAPPRLICDSRVLERYLLEAKEAENITTGCAEHCSLNENITVPDTKVNFYAWKRMEVGQQ----------------ALLVN
h1-1  MGVHECPAWLWLLLSLLSLPLGLPVLGAPPRLICDSRVLERYLLEAKEAENITTGCAEHCSLNENITVPDTKVNFYAWKRME---------------
h2-1  MGVHECPAWLWLLLSLLSLPLGLPVLGAPPRLICDSRVLERYLLEAKEAENITTGCAEHCSLNENITVPgpvgqlfpavgapaaacgStop------- mWT   MGVPERP-TLLLLLSLLLLIPLGLPVLCAPPRLICDSRVLERYILEAKEAENVTMGCAEGPRLSENITVPDTKVNFYAWKRMEVEEQAIEVWQGLSLLSEAILQAQALLAN
mS    MGVPERP-TLLLLLSLLLLIPLGLPVLCAPPRLICDSRVLERYILEAKEAENVTMGCAEGPRLSENITVPDTKVNFYAWKRME---------------
mG3   MGVPERP-TLLLLLSLLLLIPLGLPVLCAPPRLICDSRVLERYILEAKEAENVTMGCAEGPRLSENITVPDTKVNFYAWKRMEVEEQAIEVWQGLSLLSEAILQAQALLAN
mG5   MGVPERP-TLLLLLSLLLLIPLGLPVLCAPPRLICDSRVLERYILEAKEAENVTMGCAEGPRLSENITVPDTKVNFYAWKRMEVEEQAIEVWQGLSLLSEAILQAQALLAN
m301  MGVPERP-TLLLLLSLLLLIPLGLPVLCAPPRLICDSRVLERYILEAKEAENVTMGCAEGPRLSENITVPDTKVNF-----------
mK3   MGVPERP-TLLLLLSLLLLIPLGLPVLCAPPRLICDSRVLERYILEAKEAENVTMGCAEGPRLSENITVPDTKVNFYAWKRMEVEEQAIEVWQGLSLLSEAVHGRGLQERG
```

| Helix | | Helix C | | C' | | Helix D |
|---|---|---|---|---|---|---|
| Affinity | | x x | | | | x xx |

```
hWT   SSQPWEPLQLHVDKAISGLRSLTSLLRVLGAQKEAISPPDAASAAPLRTITADTFRKLFRVYSNFLRGKLKLYTGEACRTGDRStop
hS3   SSQPWEPLQLHVDKAISGLRSLTSLLRVLGAQKEAISPPDAASAAPLRTITADTFRKLFRVYSNFLRGKLKLYTGEACRTGDRStop
h1-4  SSQPWEPLQLHVDKAISGLRSLTSLLRVLGAQKEAISPPDAASAAPLRTITADTFRKLFRVYSNFLRGKLKLYTGEACRTGDRStop
h1-5  SSQPWEPLQLHVDKAISGLRSLTSLLRVLGAQKEAISPPDAASAAPLRTITADTFRKLFRVYSNFLRGKLKLYTGEACRTGDRStop
hS4   ---PWEPLQLHVDKAISGLRSLTSLLRVLGAQKEAISPPDAASAAPLRTITADTFRKLFRVYSNFLRGKLKLYTGEACRTGDRStop
h1-1  
h2-1 mWT   SSQPPETLQLHIDKAISGLRSLTSLLRVLGAQKELMSPPDTTPPAPLRTLTVDTFCKLFRVYANFLRGKLKLYTGEVCRRGDRStop
mS    ----------KELMSPPDTTPPAPLRTLTVDTFCKLFRVYANFLRGKLKLYTGEVCRRGDRStop
mG3   
mG5   SSQPPETLQLHIDKAISGLRSLTSLLRVLGAQKELMSPPDTTPPAPLRTLTVDTFC------FLRGKLKLYTGEVCRRGDRStop
M301  -------------RRGDRStop
mK3   QVTCCCHRGGPTNLLPVTVSCQPSTTPNPHQTGHYLLTSLSHGHSSTSSDILGARRTSQSSILKSKDVAGQARGPREEEPQNQLGFV
```

Fig. 5
A
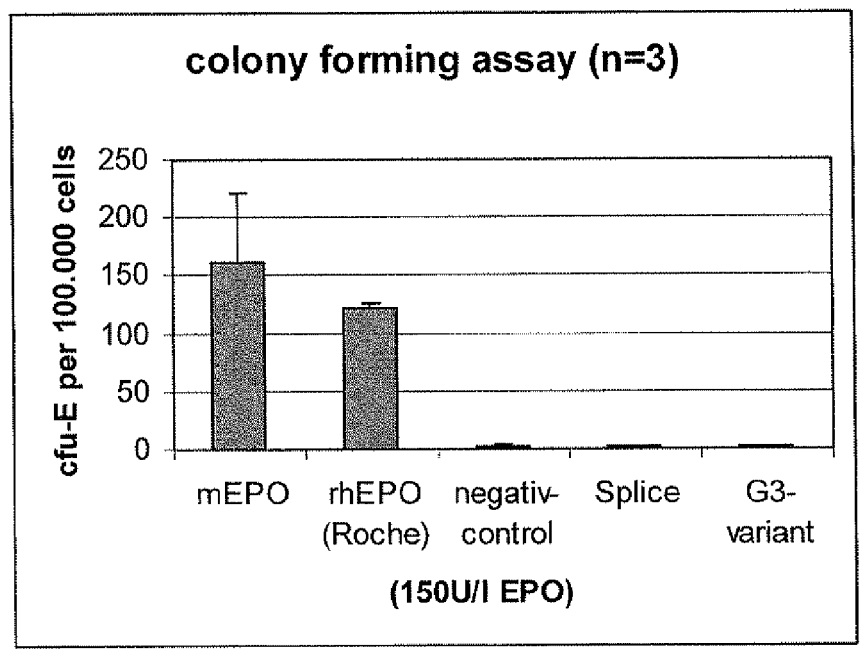
B
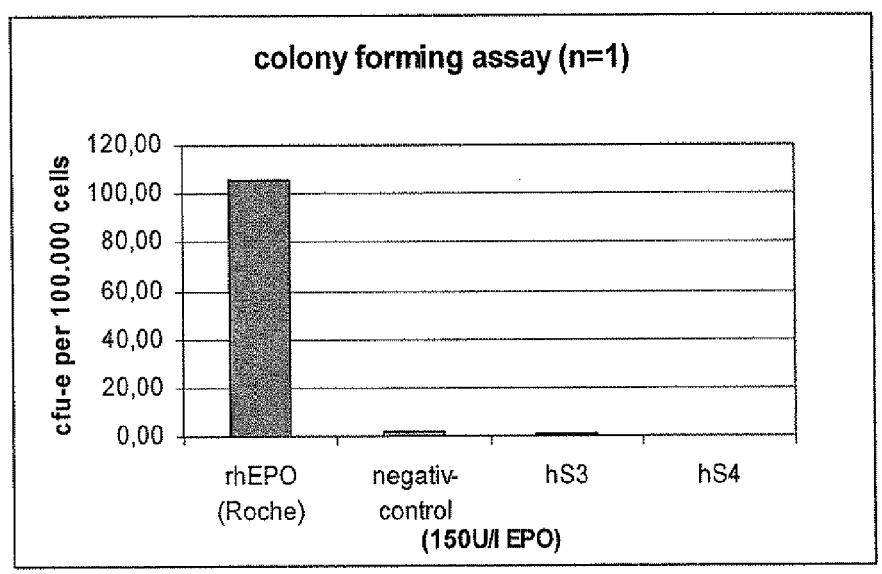

Fig. 7
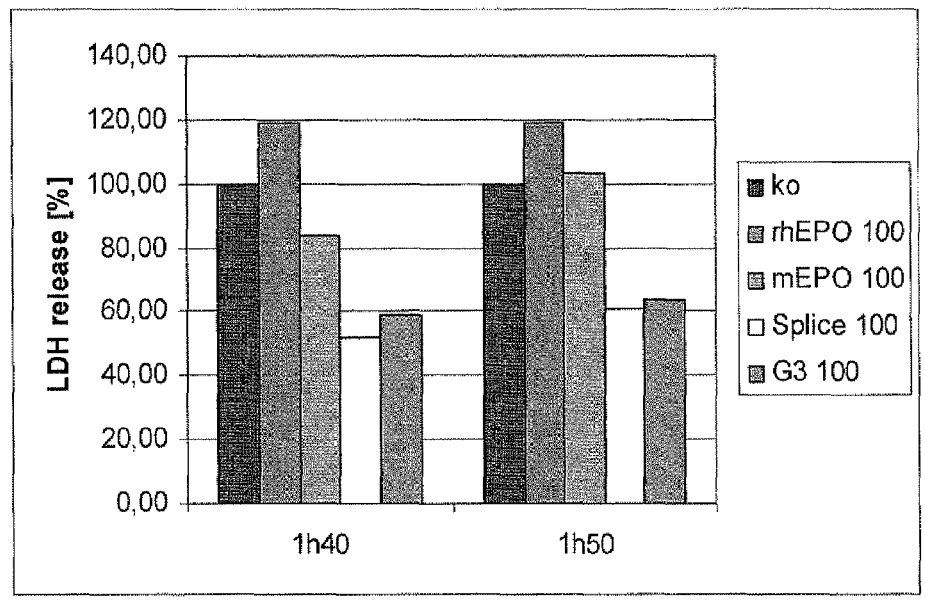
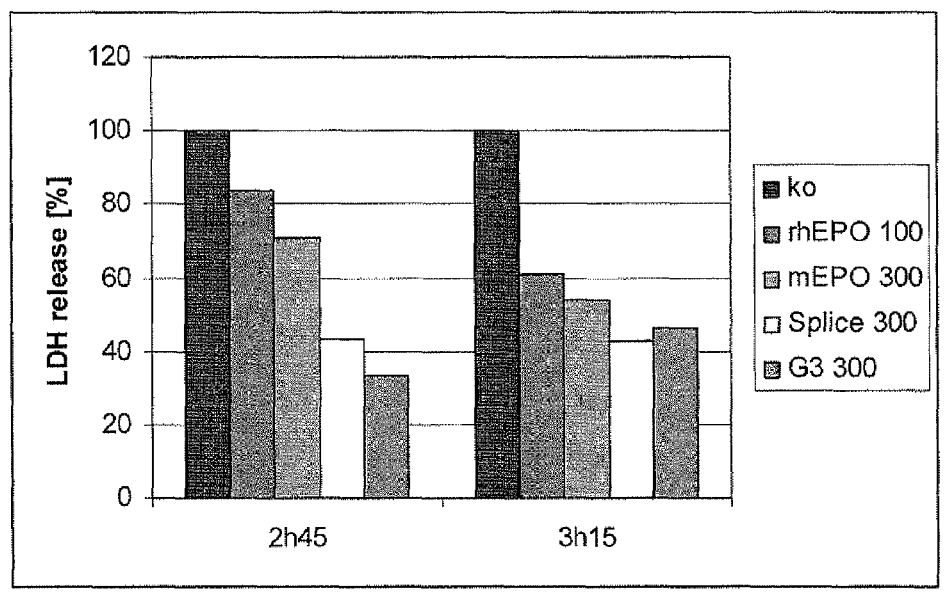

Fig. 8
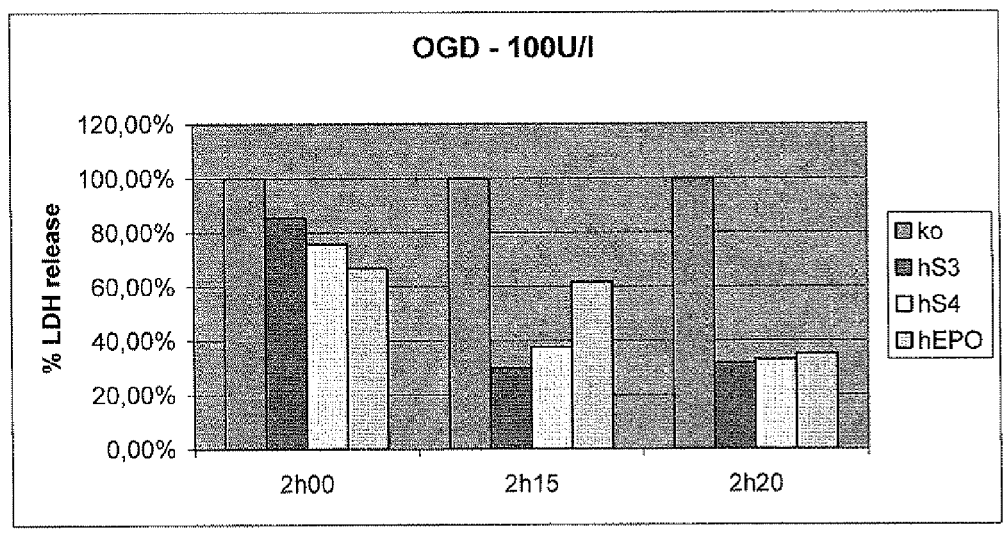
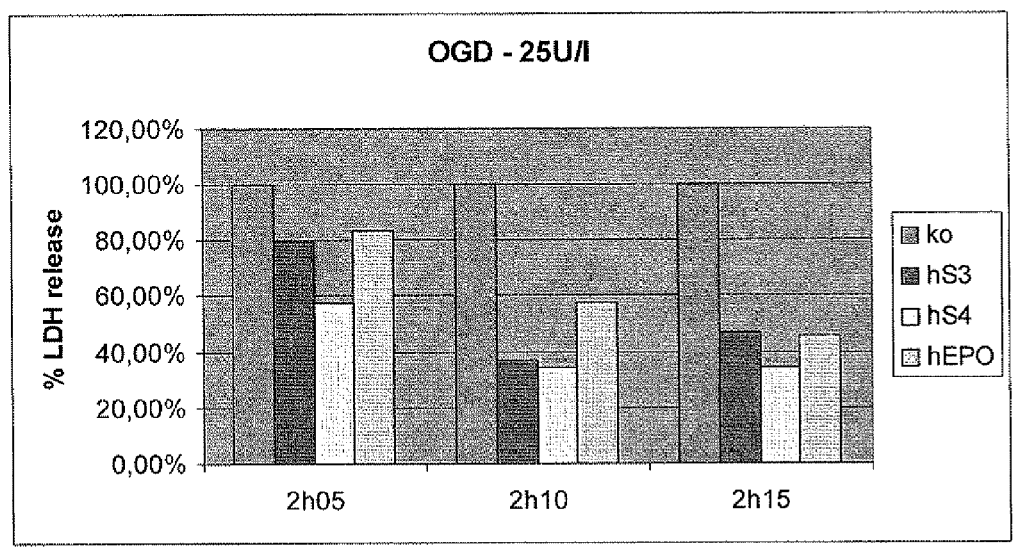

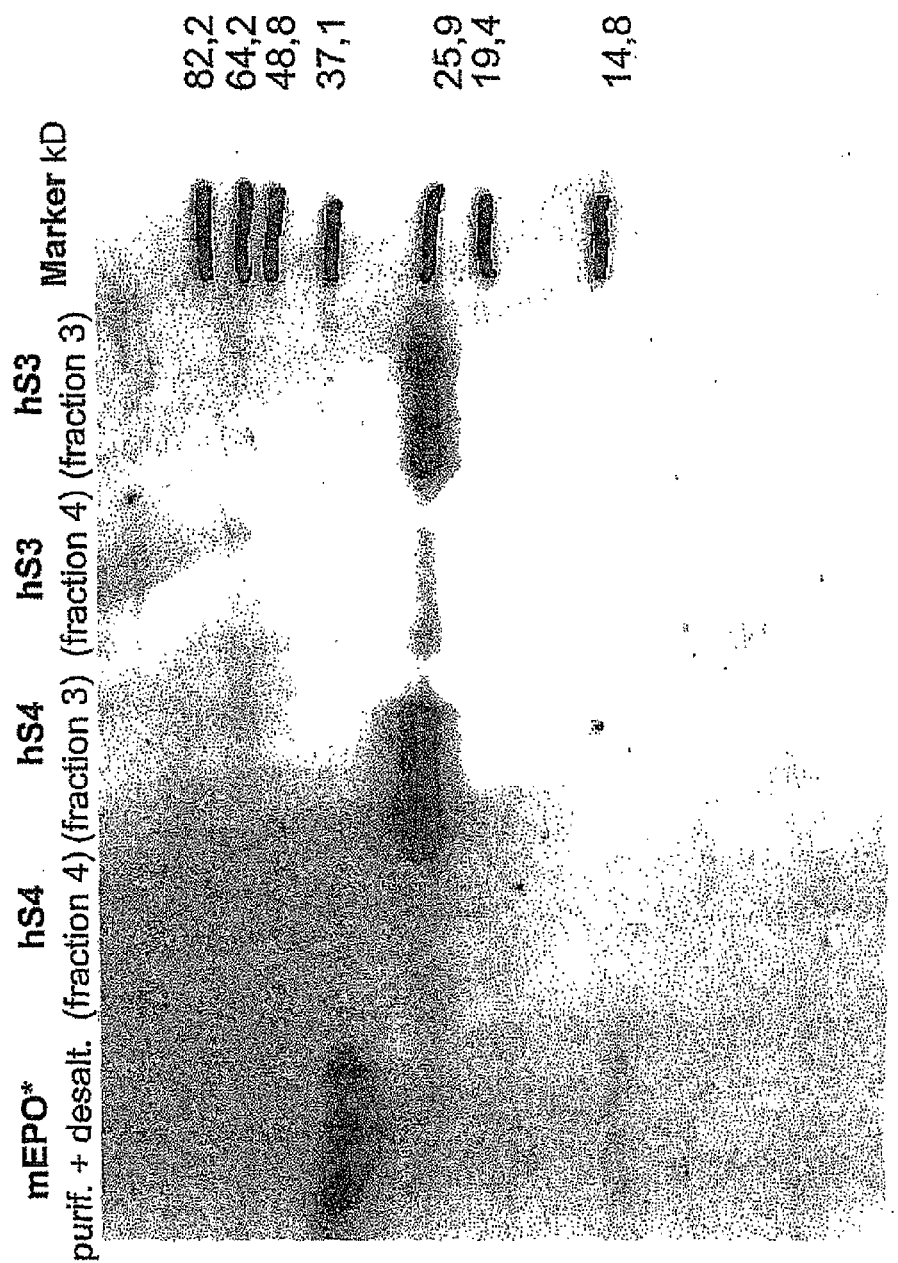

```
       Helix B                                                Helix C                Helix C'       Helix D
                                                                                                      x  xx
       0000000000      G    0000000000000000000                   000000000000000000000        000000000000000000000
hwT    ALLSEAVLRGQALLVNSSQPWEPLQLHVDKAVSGLRSLTTLLRALGAQKEAISPPDAASAAPLRTITADTFRKLFRVYSNFLRGKLKLYTGEAC
Hs3    ALLSEAVLRGQALLVNSSQPWEPLQLHVDKAVSGLRSLTTLLRALGAQKEAISPPDAASAAPLRTITADTFRKLFRVYSNFLRGKLKLYTGEAC
h1-4   ---------ALLVNSSQPWEPLQLHVDKAVSGLRSLTTLLRALGAQKEAISPPDAASAAPLRTITADTFRKLFRVYSNFLRGKLKLYTGEAC
h1-5   ---------ALLVNSSQPWEPLQLHVDKAVSGLRSLTTLLRALGAQKEAISPPDAASAAPLRTITADTFRKLFRVYSNFLRGKLKLYTGEAC
hS4    ----------------PWEPLQLHVDKAVSGLRSLTTLLRALGAQKEAISPPDAASAAPLRTITADTFRKLFRVYSNFLRGKLKLYTGEAC
h1-1   ------------------------------------------------------------------------------------------
h2-1   ------------------------------------------------------------------------------------------
hA     ------------------------------------------------------------------------------------------
hAmA   ------------------------------------------------------------------------------------------
hAmE   ------------------------------------------------------------------------------------------
hA-10  ------------------------------------------------------------------------------------------
hA-20  ------------------------------------------------------------------------------------------
mWT    SLLSEAILQAQALLANSSQPPETLQLHIDKAISGLRSLTSLLRVLGAQKELMSPPDTTPPAPLRTLTVDTFCKLFRVYANFLRGKLKLYTGEVC
mS     ------------------------------------------KELMSPPDTTPPAPLRTLTVDTFCKLFRVYANFLRGKLKLYTGEVC
mG3    SLLSEAILQAQALLAN--------------------------------------------------------------------------
mG5    SLLSEAILQAQALLANSSQPPETLQLHIDKAISGLRSLTSLLRVLGAQKELMSPPDTTPPAPLRTLTVDTFC------FLRGKLKLYTGEVC
m301   SLLSEAVHGRGLQERGQVTCCHRGGPTNLLPVTVSCQPSTTPNPHQTGHYLLTSLSHGHSSTSSDILGARRTSQSSILKSKDVAGQARGPREE
mK3    SLLSEAVHGRGLQERGQVTCCHRGGPTNLLPVTVSCQPSTTPNPHQTGHYLLTSLSHGHSSTSSDILGARRTSQSSILKSKDVAGQARGPREE
```

FIG. 10 (CONTINUED)

| | |
|---|---|
| hWT | RTGDRStop |
| hS3 | RTGDRStop |
| h1-4 | RTGDRStop |
| h1-5 | RTGDRStop |
| hS4 | RTGDRStop |
| h1-1 | ------ |
| h2-1 | ------ |
| hA | ------ |
| hAmA | ------ |
| hAmE | ------ |
| hA-10 | ------ |
| hA-20 | ------ |
| hWT | RTGDRStop |
| mS | RTGDRStop |
| mG3 | RTGDRStop |
| mG5 | RTGDRStop |
| m301 | RTGDRStop |
| mK3 | EPQNQLGFV |

FIG. 10 (CONTINUED)

Fig. 15
A
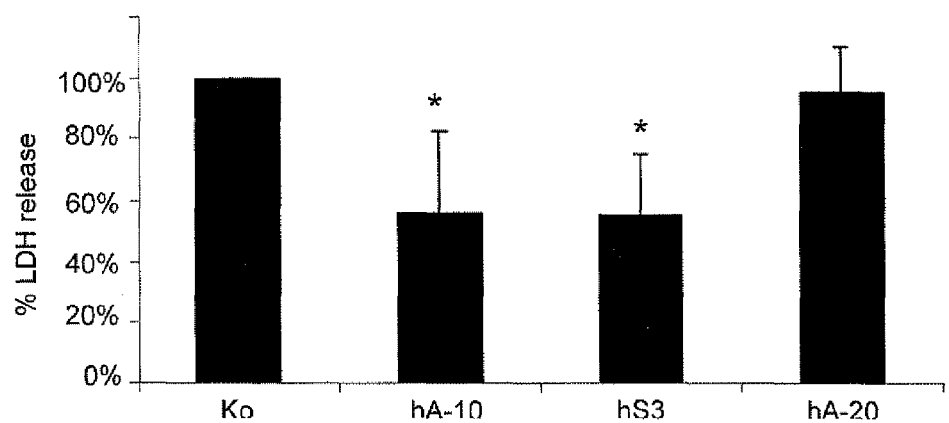
B
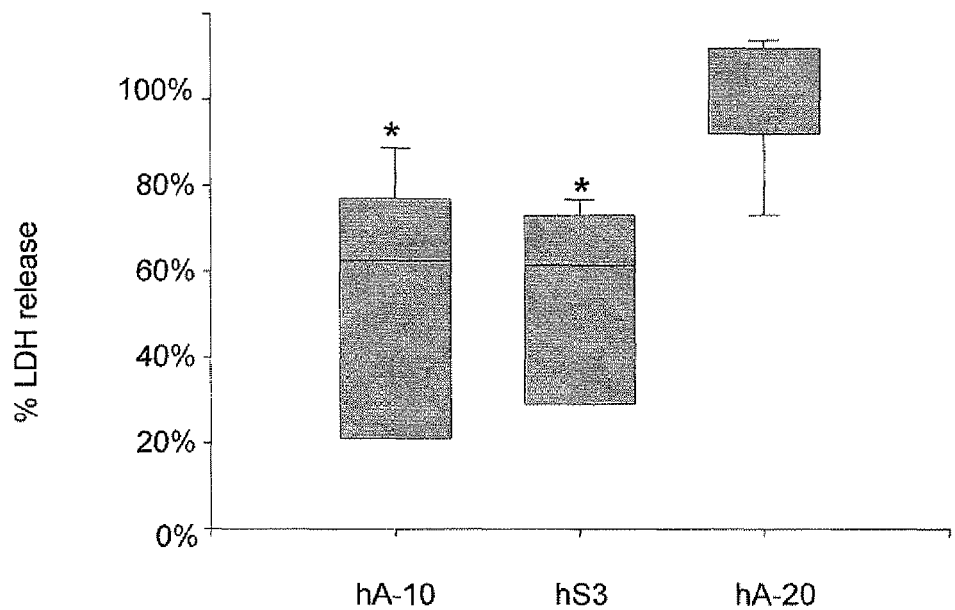

Fig. 17

```
atgggggtgcacgaatgtcctgcctggctgtggcttctcctgtccctgctgtcgctccctctgggcctcccagtc
atgggggtgcacgaatgtcctgcctggctgtggcttctcctgtccctgctgtcgctccctctgggcctcccagtc
atgggggtgcacgaatgtcctgcctggctgtggcttctcctgtccctgctgtcgctccctctgggcctcccagtc
atgggggtgcacgaatgtcctgcctggctgtggcttctcctgtccctgctgtcgctccctctgggcctcccagtc
atgggggtgcacgaatgtcctgcctggctgtggcttctcctgtccctgctgtcgctccctctgggcctcccagtc
atgggggtgcacgaatgtcctgcctggctgtggcttctcctgtccctgctgtcgctccctctgggcctcccagtc ctgggcgccccaccacgcctcatctgtgacagccgagtcctggagaggtacctcttggaggccaaggaggccgag
ctgggcgccccaccacgcctcatctgtgacagccgagtcctggagaggtacctcttggaggccaaggaggccgag
ctgggcgccccaccacgcctcatctgtgacagccgagtcctggaggcgtacctcttggaggccaaggaggccgag
ctgggcgccccaccacgcctcatctgtgacagccgagtcctggaggagtacctcttggaggccaaggaggccgag
ctgggcgccccaccacgcctcatctgtgacagccgagtcctggagaggtacctc---------------------
ctgggcgccccaccacgcctcatc---------------------------------------------------- aatatcacgacgggctgtgctgaacactgcagcttgaatgagaatatcactgtcccagacaccaaagttaatttc
aatatcacg-------------------------------------------------------------------
aatatcacg-------------------------------------------------------------------
aatatcacg-------------------------------------------------------------------
----------------------------------------------------------------------------
---------------------------------------------------------------------------- tatgcctggaagaggatggaggtcgggcagcaggccgtagaagtctggcagggcctggccctgctgtcggaagct
----------------------------------------------------------------------------
----------------------------------------------------------------------------
----------------------------------------------------------------------------
----------------------------------------------------------------------------
---------------------------------------------------------------------------- gtcctgcggggccaggccctgttggtcaactcttcccagccgtgggagcccctgcagctgcatgtggataaagcc
----------------------------------------------------------------------------
----------------------------------------------------------------------------
----------------------------------------------------------------------------
----------------------------------------------------------------------------
---------------------------------------------------------------------------- gtcagtggccttcgcagcctcaccactctgcttcgggctctgcgagcccagaaggaagccatctcccctccagat
----------------------------------------------------------------------------
----------------------------------------------------------------------------
----------------------------------------------------------------------------
----------------------------------------------------------------------------
---------------------------------------------------------------------------- gcggcctcagctgctccactccgaacaatcactgctgacactttccgcaaactcttccgagtctactccaatttc
----------------------------------------------------------------------------
----------------------------------------------------------------------------
----------------------------------------------------------------------------
----------------------------------------------------------------------------
---------------------------------------------------------------------------- ctccggggaaagctgaagctgtacacaggggaggcctgcaggacaggggacagatga  hWT
--------------------------------------------------------  hA
--------------------------------------------------------  hAmA
--------------------------------------------------------  hAmE
--------------------------------------------------------  hA-10
--------------------------------------------------------  hA-20
```

Fig. 18 hA (hWT-EPO Helix A) – SEQ ID NO 55 atggggtgcacgaatgtcctgcctggctgtggcttctcctgtccctgctgtcgctccctc
tgggcctcccagtcctgggcgccccaccacgcctcatctgtgacagccgagtcctggagag
gtacctcttggaggccaaggaggccgagaatatcacg hAmA (Mutant Alanin hWT-EPO Helix A) SEQ ID NO 56
atggggtgcacgaatgtcctgcctggctgtggcttctcctgtccctgctgtcgctccctc
tgggcctcccagtcctgggcgccccaccacgcctcatctgtgacagccgagtcctggaggc
gtacctcttggaggccaaggaggccgagaatatcacg hAmE (Mutant Glutamic-Acid hWT-EPO Helix A)  SEQ ID NO 57
atggggtgcacgaatgtcctgcctggctgtggcttctcctgtccctgctgtcgctccctc
tgggcctcccagtcctgggcgccccaccacgcctcatctgtgacagccgagtcctggagga
gtacctcttggaggccaaggaggccgagaatatcacg hA-10 (hWT-EPO Helix A minus 10aa) SEQ ID NO 58
atggggtgcacgaatgtcctgcctggctgtggcttctcctgtccctgctgtcgctccctc
tgggcctcccagtcctgggcgccccaccacgcctcatctgtgacagccgagtcctggagag
gtacctc hA-20 (hWT-EPO Helix A minus 20aa) SEQ ID NO 59
atggggtgcacgaatgtcctgcctggctgtggcttctcctgtccctgctgtcgctccctc
tgggcctcccagtcctgggcgccccaccacgcctcatc

Fig. 19

A - hA DNA without leader (SEQ ID NO. 65) - hWT-EPO Helix A without leader (transport or signal) sequence, sequence encoding mature exported protein:

5'-gccccaccacgcctcatctgtgacagccgagtcctggagaggtacctcttggaggccaaggaggccgagaatatcacg-3'

Leader-Sequence (SEQ ID NO 63):

5'-atgggggtgcacgaatgtcctgcctggctgtggcttctcctgtccctgctgtcgctccctctgggcctcccagtcctgggc-3'

B - hA amino acid without leader (SEQ ID NO. 66):

(hWT-EPO Helix A without leader transport sequence, mature exported protein):

APPRLICDSRVLERYLLEAKEAENIT

C - hA-10 DNA without leader (SEQ ID NO 60)

5'- gccccaccac gcctcatctg tgacagccga gtcctggaga ggtacctc -3'

D - hA-10 amino acid sequence without leader (SEQ ID NO 61)

APPRLICDSRVLERYL

E - Leader amino acid sequence (SEQ ID NO 62):

MGVHECPAWLWLLLSLLSLPLGLPVLG

Fig. 20
Experimental Design 1
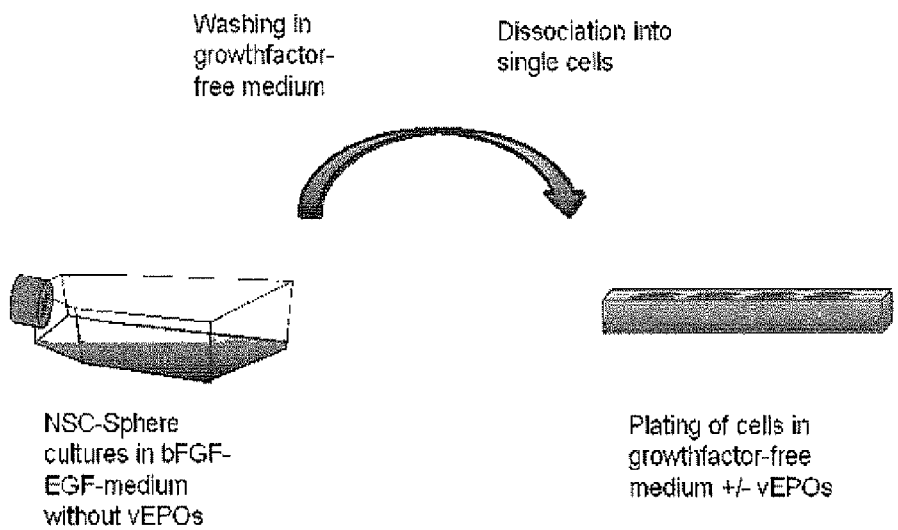
Experimental Design 2
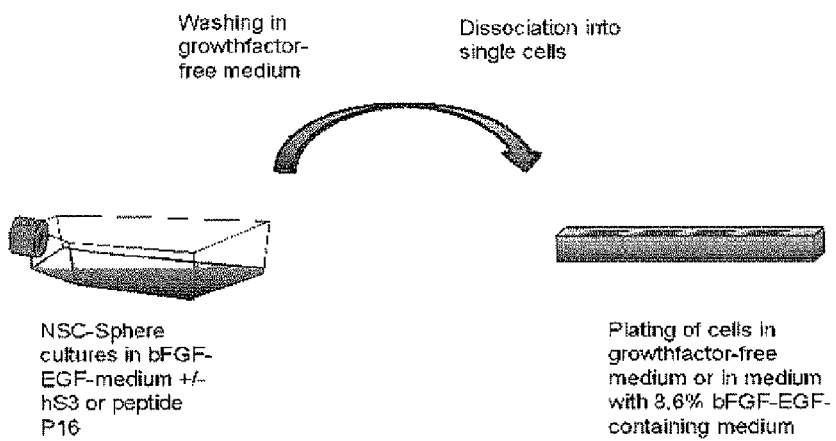

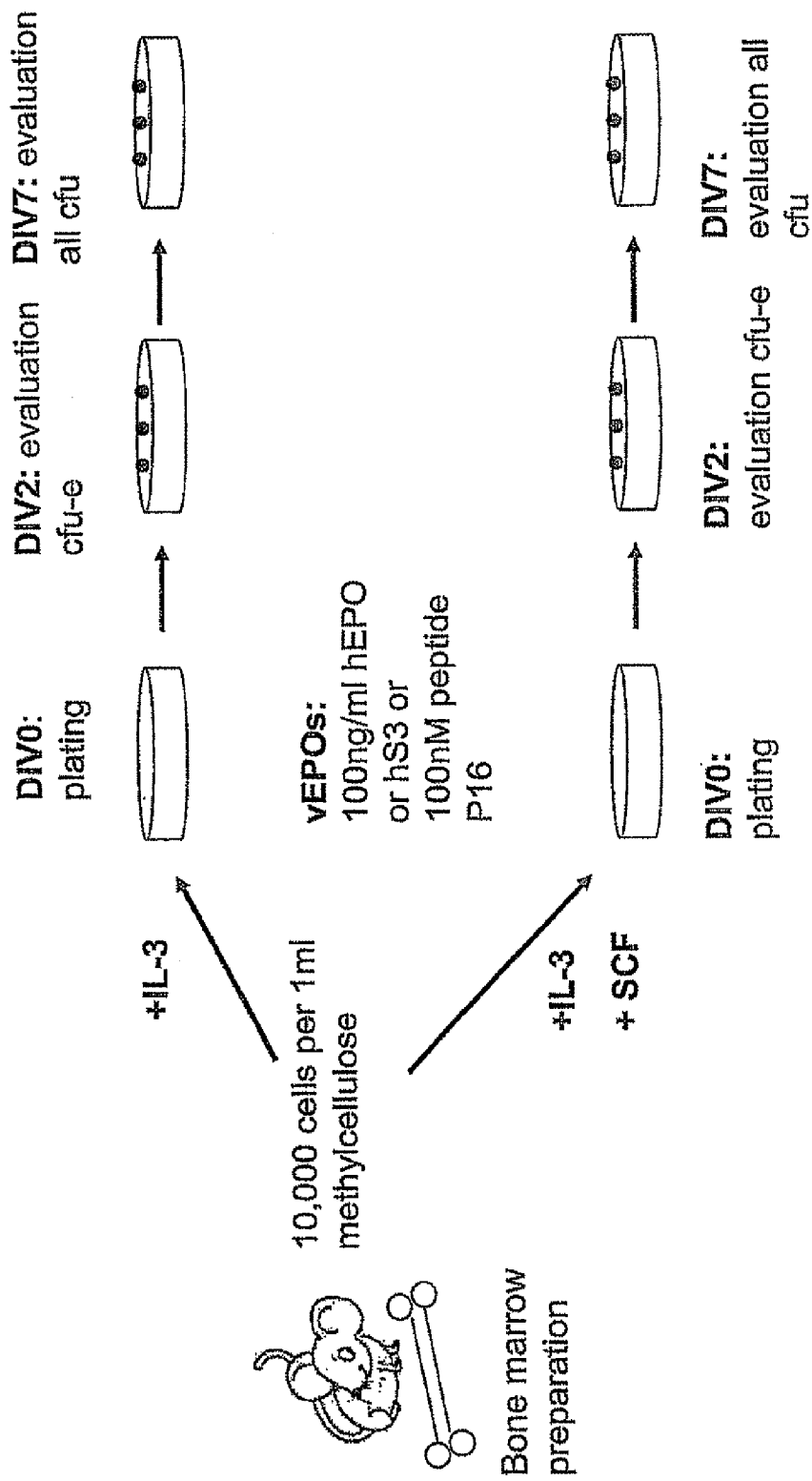

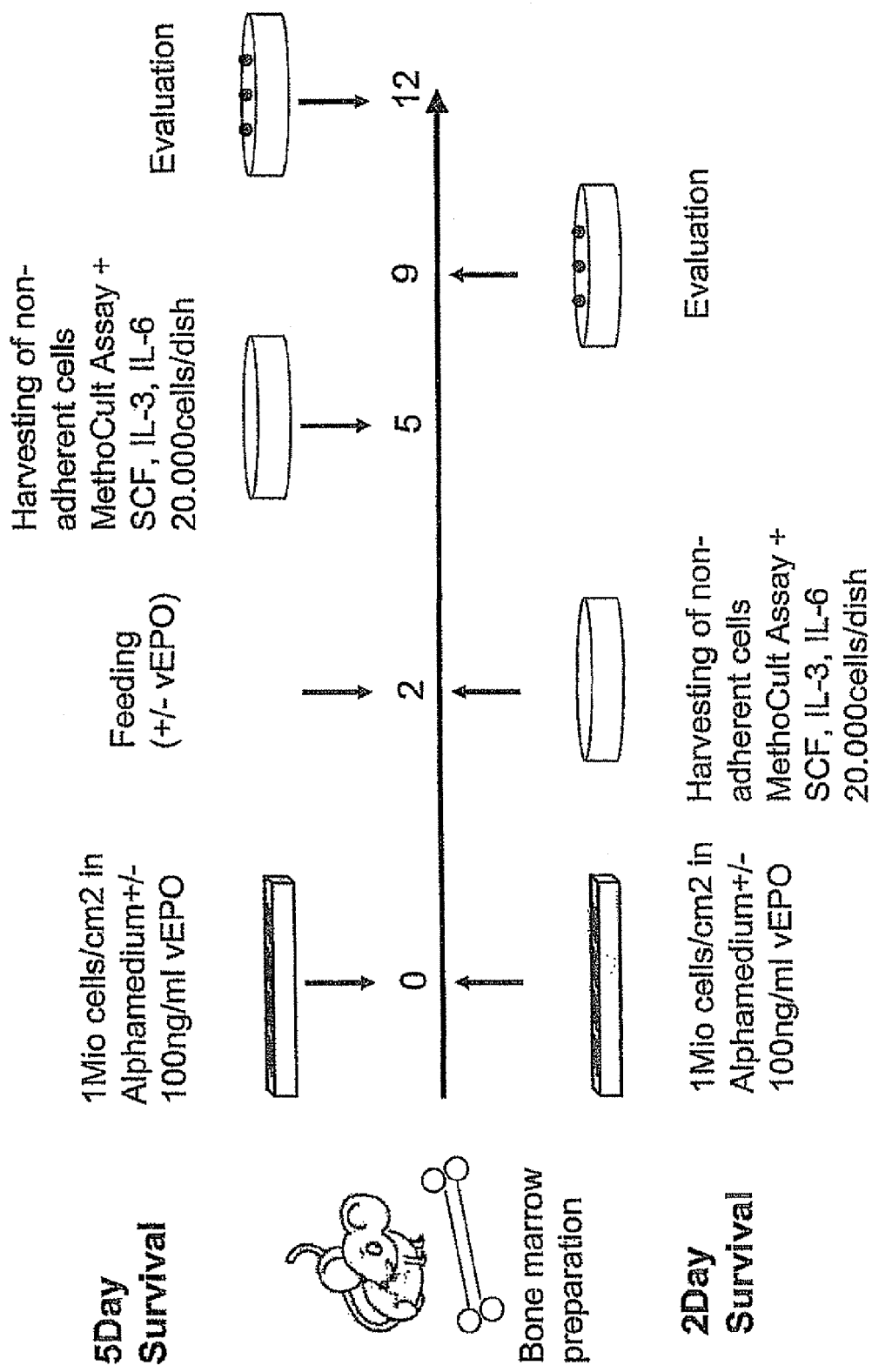

METHOD OF CELL CULTURE AND METHOD OF TREATMENT COMPRISING A VEPO PROTEIN VARIANT

SEQUENCE LISTING

The instant application contains a Sequence Listing which has been submitted in ASCII format via EFS-Web and is hereby incorporated by reference in its entirety. Said ASCII copy, created on Aug. 10, 2011, is named SCH1400U.txt and is 46,376 bytes in size.

FIELD OF THE INVENTION

The invention relates to methods for expanding stem or progenitor cells in a controllable bioprocess, providing for expansion of the stem or progenitor cells, controlling endogenous factor production, and providing cell populations (mixtures of stem, progenitor, and/or mature cells) that are useful for transplantation and other therapeutic treatments. The invention also relates to promoting survival of stem or progenitor cells in culture, bioreactors and in living organisms. Moreover, the invention relates to methods for differentiating stem or progenitor cells and for providing a milieu supportive of stem or progenitor cell function. The present invention relates in particular to a method of cell culture and treatment comprising a vEPO protein variant. In one embodiment, a method of increasing the number, survival and differentiation of neural stem or progenitor cells and the survival of hematopoietic and mesenchymal (stromal) stem or progenitor cells using a vEPO protein variant is described. In another embodiment, the invention can be used for treating an individual with an acute or chronic neurological, psychiatric or hematological disorder with stem or progenitor cells making use of a vEPO protein variant.

BACKGROUND OF THE INVENTION

Stem cells are primal cells that retain the ability to renew themselves through cell division and can differentiate into a wide range of specialized cell types. Research in the stem cell field grew out of findings by Canadian scientists Ernest A. McCulloch and James E. Till in the 1960s.

The two categories of stem cells include embryonic stem cells and adult stem cells and possibly a third, cord blood-derived embryonic-like stem cells (CBEs). In a blastocyst of a developing embryo, stem cells differentiate into all of the specialized embryonic tissues. In adult organisms, stem cells and progenitor cells act as a repair system for the body, replenishing specialized cells. This makes stem cells interesting for therapeutic applications.

Totipotent stem cells are produced from the fusion of an egg and sperm cell. Cells produced by the first few divisions of the fertilized egg cell are also totipotent. These cells can differentiate into embryonic and extraembryonic cell types.

Pluripotent stem cells are the descendants of totipotent cells and can differentiate into cells derived from the three germ layers.

Multipotent stem cells can produce only cells of a closely related family of cells (e.g. hematopoietic stem cells differentiate into red blood cells, white blood cells, platelets, etc.).

Unipotent cells can produce only one cell type, but have the property of self-renewal which distinguishes them from non-stem cells.

The term progenitor cell is used in cell biology and developmental biology to refer to immature or undifferentiated cells. While progenitor cells share many common features with stem cells, the term is far less restrictive. The majority of progenitor cells lies dormant or possesses little activity in the tissue in which they reside. They exhibit slow growth and their main role is to replace cells lost by normal attrition.

Embryonic stem cells (ES cells) are stem cells derived from the inner cell mass of a blastocyst. ES cells are pluripotent, and give rise during development to all derivatives of the three primary germ layers: ectoderm, endoderm and mesoderm. In other words, they can develop into each of the more than 200 cell types of the adult body when given sufficient and necessary stimulation for a specific cell type. When given no stimuli for differentiation, ES cells will continue to divide in vitro and each daughter cell will remain pluripotent. The pluripotency of ES cells has been rigorously demonstrated in vitro and in vivo, thus they can be indeed classified as stem cells. Because of their unique combined abilities of unlimited expansion and pluripotency, embryonic stem cells are a potential source for regenerative medicine and tissue replacement after injury or disease. To date, no approved medical treatments have been derived from embryonic stem cell research, ES cells were first derived from mouse embryos in 1981 by two independent research groups (Evans & Kaufman and Martin). A breakthrough in human embryonic stem cell research came in November 1998 when a group led by James Thomson at the University of Wisconsin-Madison first developed a technique to isolate and grow the cells when derived from human blastocysts.

Adult stem cells reside in nearly every tissue, including the brain, bone marrow, peripheral blood, kidney, epithelia of the digestive system, and also the skin, retina, muscles, pancreas and liver (Blau et al., 2001; Tarnowski and Sieron, 2006). They contribute to tissue homeostasis and regeneration after damage. However, their specific properties are often elusive because of their heterogeneity and technical difficulties in identifying these rare cells and their progeny. Hematopoietic stem cells are the best characterized adult stem cells. They are able to reconstitute all cells of the blood. Stem cells also exist in the adult brain (Gage, 2000). These so-called neural stem cells give rise to neurons and glial cells in tissue culture or following direct injection into brains. Neural stem cells can be obtained from adult brain tissue following proteolytic dissociation and density gradient centrifugation. They can be grown and expanded as ‘neurospheres’ in culture (Quesenberry et al., 1999). Mesenchymal (stromal) stem cells derived from bone marrow, umbilical cord, placenta or adipose tissue give rise to adipocytes, chondrocytes, tenocytes and osteocytes. However, they also possess a remarkable degree of plasticity when exposed to specific environmental factors (Grove at al., 2004). Multipotent adult progenitor cells are pluripotent cells obtained in culture from mesenchymal stem cells (Jiang of al., 2002). Recently, pluripotent spermatogonial stem cells were isolated from adult mouse testis (Gunn et al., 2006).

Pluripotent cells can also be obtained from somatic cells by nuclear reprogramming, including cloning, cell fusion and cytoplasmic mixing (Pomerantz and Blau, 2004).

The goal of regenerative medicine is to restore tissue function. Stem cells and progenitor cells offer the potential to replace lost or damaged cells and to create a milieu supportive of functional recovery. Clinical interventions can encompass stimulation of endogenous stem and progenitor cells populations. Unfortunately, most of the newly generated cells do not fully differentiate or die or fail to migrate to the sites of damage. These obstacles are exemplified in a study on neuronal replacement from endogenous neural precursors after cerebral ischemia (Arvidsson et al., 2002). Erythropoietin was recently shown to enhance and/or induce the migration of multipotent neural stem cells and their progeny (see patent WO 2004/011021). Administration of exogenous stem or progenitor cells is an equally appealing avenue for the treatment of diseases which are refractory to most other treatments. ES and ES-like cells would seem ideally suited for stem cell therapy due to their pluripotency and self-renewal capacity. However, the use of ES cells is ethically controversial. Moreover, challenges to overcome are making the stem cells differentiate into specific viable cells consistently, and controlling against unchecked cell division because undifferentiated embryonic stem cells can form teratomas after transplantation. Allogeneic transplantation of stem cells and progenitor cells also carries the likelihood of immune rejection. Transplantation of adult stem cells may overcome some of these obstacles, but the differentiative potential of these cells is limited and many cells die after transplantation. Thus, pre-differentiation of the stem cells ex vivo may be required for their functional integration into target tissue. Adult stem cells are difficult to expand or even to maintain in culture (e.g. expansion of naive hematopoietic stem cells is impossible ex vivo). In general, it is laborious to keep stem and progenitor cells growing, well-nourished and stable in the laboratory so they do not die or turn into a cell type with less potential. Further, purification of the stem or progenitor cells is required prior to transplantation because a mixed population of cells could cause the growth of unwanted tissues. The purification procedure is very strenuous on the cells and often associated with substantial cell loss.

The invention of methods of cell culture and treatment comprising a vEPO protein variant will help to overcome many of the difficulties associated with stem or progenitor cell therapy.

SUMMARY OF THE INVENTION

In one aspect the present invention is concerned with a method of cell culture, comprising the steps of (i) obtaining a stem or progenitor cell sample, (ii) culturing the stem or progenitor cell sample in media and under closed conditions appropriate to cause proliferation or differentiation of the stem or progenitor cells, wherein the media comprises a vEPO protein variant, optionally (iii) purifying the stem or progenitor cells ex vivo.

The invention relates to a method of increasing the number and survival of stem and progenitor cells in vitro and in vivo using a vEPO protein variant. The invention also relates to improved differentiation of stem and progenitor cells in vitro and in vivo using a vEPO protein variant.

The invention relates to a method of treating an individual with an acute or chronic degenerative, inflammatory or other disorder leading to cell loss and/or tissue dysfunction, wherein the individual is treated with vEPO or cells expressing a vEPO protein variant due to the presence of an exogenous copy of a nucleic acid encoding a vEPO protein to support and enhance regeneration by endogenous stem and progenitor cells populations.

The invention also relates to a method of treating an individual with an acute or chronic degenerative, inflammatory or other disorder leading to cell loss or tissue dysfunction, wherein the individual is treated by transplanting stem or progenitor cells, wherein
  i) the stem or progenitor cells are pre-incubated in a cell culture comprising a vEPO protein variant prior to transplantation and/or,
  ii) the stem or progenitor cells express the vEPO protein variant due to the presence of an exogenous copy of a nucleic acid encoding a vEPO protein and/or,
  iii) the stem or progenitor cells are transplanted and the vEPO protein variant is administered shortly before the transplant, shortly after the transplant or together with the transplant.

The vEPO protein variant may be selected from the group consisting of:
  (a) proteins termed hs3, h1-4, h1-5, hs4, h1-1, h2-1, mS, mG3, mG5, m301 and mK3 having the deduced amino acid sequence as shown in SEQ ID NOs 2, 4, 6, 8, 10, 12, 14, 16, 18, 20, and 22, respectively;
  (b) proteins encoded by polynucleotides having the coding sequence as shown in SEQ ID NOs: 1, 3, 5, 7, 9, 11, 13, 15, 17, 19, and 21 encoding at least the mature form of the protein;
  (c) proteins encoded by a polynucleotide encoding a humanized version of the proteins mS, mG3, mG5, m301 and mK3 having the deduced amino acid sequence as shown in SEQ ID NOs 14, 16, 18, 20, and 22;
  (d) a protein comprising a fusion of an amino acid sequence selected from the group of amino acid sequences as shown in SEQ ID NO 24, 26, 28, and 30, at the N-terminus of an amino acid sequence selected from the group of amino acid sequences as shown in SEQ ID NO 32, 34, 36, and 38;
  (e) a protein encoded by a polynucleotide comprising a fusion of polynucleotide sequences selected from the group of polynucleotide sequences as shown in SEQ ID NO 23, 25, 27, and 29, 5' of a polynucleotide sequence selected from the group of polynucleotide sequences as shown in SEQ ID NO. 31, 33, 35, and 37;
  (f) a derivative of a protein or a peptide encoded by a polynucleotide of any one of (a) to (e), wherein in said derivative between 1 and 10 amino acid residues are conservatively substituted compared to said protein, and said derivative has cell protective and in particular neuroprotective activity, but essentially no hematopoietic activity;
  (g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;
  (h) a protein termed ha, hAmA, hAmE, hA-10 and hA-10-transport, hA-transport sequence, having the deduced amino acid sequence as shown in SEQ ID NOs 50, 51, 52, 53, 61 and 66 respectively;
  (i) a protein encoded by a polynucleotide having the coding sequence, as shown in SEQ ID NOs: 55, 56, 57, 58, 60 and 65 encoding at least the mature form of the protein;
  (j) a derivative of a protein of any one of (h) to (i), wherein in said derivative between 1 and 10 amino acid residues are conservatively substituted compared to said protein, and said derivative has cell protective and in particular neuroprotective activity, but essentially no hematopoietic activity;
  (k) a fragment of a protein of any one of (h) to (i), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;

(l) an erythropoietin (EPO) variant encoded by a polynucleotide selected from the group consisting of:
(1) polynucleotides, which comprise more than six amino acids from the N-terminus of mature human EPO,
(2) polynucleotides, which comprise the N-terminal part of full length EPO including helix A and which lack at least one of the following:
(i) a fragment of at least 10 amino acids between helix A and helix B,
(ii) a fragment of at least 10 amino acids of helix B,
(iii) a fragment of at least 2 amino acids between helix B and helix C,
(iv) a fragment of at least 10 amino acids of helix C,
(v) a fragment of at least 10 amino acids between helix C and D, and/or
(vi) a fragment of at least 10 amino acids of helix D, wherein said variant has cell protective and in particular neuroprotective activity, but essentially no hematopoietic activity,
(3) polynucleotides encoding a derivative of a protein encoded by a polynucleotide of any one of (a), wherein in said derivative between 1 and 10 amino acid residues are conservatively substituted compared to said protein, and said derivative has cell protective and in particular neuroprotective activity, but essentially no hematopoietic activity and,
(4) polynucleotides, the complementary strand of which hybridizes under stringent conditions to a polynucleotide as defined in any one of (1) to (2) and which code for a protein having cell protective and in particular neuroprotective activity, but essentially no hematopoietic activity; or the complementary strand of such a polynucleotide;
(m) a derivative of a protein of any one of (a) to (l), wherein in said derivative amino acid residues are truncated from the transport sequence (SEQ ID NO. 62 for amino acid sequence and SEQ ID NO 63 for polynucleotide sequence), and said derivative has cell protective and in particular neuroprotective activity, but essentially no hematopoietic activity such as, but not limited to hA without leader (SEQ ID NO. 66).

DETAILED DESCRIPTION OF THE INVENTION

Unless otherwise defined, all technical and scientific terms used herein have the same meaning as commonly understood by one of ordinary skill in the art to which this invention pertains. The terms "vEPO variants", "vEPO proteins" and "vEPO (poly)peptides" are used interchangeably. Early characterization of human urinary and recombinant erythropoietin revealed that the 27-residue NH2-terminal "leader" peptide was correctly and consistently cleaved during secretion of the recombinant protein into conditioned medium, yielding the "mature" NH2 terminus (Recny et al., 1987). Thus, the "leader" sequence, herein also called "transport" or "signal" sequence (SEQ ID NO 62 for amino acid sequence and SEQ ID NO 63 for polynucleotide sequence), is of relevance for the secretion of vEPO variants from cells, e.g. for the production of recombinant vEPO protein (see also below). The therapeutically active vEPO variants are the "mature" proteins and peptides, thus sequences must encode "at least the mature form of the protein". In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The present invention is based on the surprising observation that it is possible to increase the number and viability of stem and progenitor cells during isolation from tissues and cell culture when the novel vEPO peptide or protein is incubated with said cells. The present invention is also based on the observation that the differentiation of stem and progenitor cells is improved in the presence of the novel vEPO peptide or protein. In a preferred embodiment, neural, hematopoietic and mesenchymal (stromal) stem and progenitor cells are treated with vEPO peptide or protein.

This allows for improved characterization and selection of stem and progenitor cells ex viva Further, maintenance and/or expansion in culture, genetic modification, labelling with markers for cell tracking including contrast agents, partial or complete differentiation ex vivo and purification prior to administration is now improved.

The novel vEPO proteins facilitate survival and partial or full differentiation of stem and progenitor cells ex vivo, including but not restricted to the prevention of cell death, modulation of epigenetic modification and gene expression, initiation of intra-cellular signal transduction. As can be seen in particular from FIGS. 22 and 27, the vEPO variants according to the invention have the capability of enhancing the survival rate of stem cells as well progenitor cells. Here, the figures show data for neural stem and progenitor cells. This effect of the vEPO variants can also be observed in hematopoietic progenitor cells as can be seen from FIGS. 33 and 35, as well in mesenchymal (stromal) cells (FIG. 36). The inventors have also found that the vEPO variants according to the invention enhance proliferation of stem cells and progenitor cells. This was demonstrated for neural stem and progenitor cells (see FIGS. 24 and 28). The vEPO variants according to the invention are able to enhance the differentiation of stem cells and progenitor cells as can be seen for neural stem and progenitor cells in FIGS. 22, 25 and 26.

The invention relates to a method of cell culture, comprising the steps of (i) obtaining a stem or progenitor cell sample, (ii) culturing the stem or progenitor cell sample in media and under closed conditions appropriate to cause proliferation or differentiation of the stem or progenitor cells and optionally (iii) purifying the stem or progenitor cells ex vivo, wherein the media comprises a vEPO protein variant selected from the group consisting of:
(a) proteins termed hs3, h1-4, h1-5, hs4, h1-1, h2-1, mS, mG3, mG5, m301 and mK3 having the deduced amino acid sequence as shown in SEQ ID NOs 2, 4, 6, 8, 10, 12, 14, 16, 18, 20, and 22, respectively;
(b) proteins encoded by polynucleotides having the coding sequence as shown in SEQ ID NOs: 1, 3, 5, 7, 9, 11, 13, 15, 17, 19, and 21 encoding at least the mature form of the protein;
(c) proteins encoded by a polynucleotide encoding a humanized version of the proteins mS, mG3, mG5, m301 and mK3 having the deduced amino acid sequence as shown in SEQ ID NOs 14, 16, 18, 20, and 22;
(d) a protein comprising a fusion of an amino acid sequence selected from the group of amino acid sequences as shown in SEQ ID NO 24, 26, 28, and 30, at the N-terminus of an amino acid sequence selected from the group of amino acid sequences as shown in SEQ ID NO 32, 34, 36, and 38;
(e) a protein encoded by a polynucleotide comprising a fusion of polynucleotide sequences selected from the group of polynucleotide sequences as shown in SEQ ID NO 23, 25, 27, and 29, 5' of a polynucleotide sequence selected from the group of polynucleotide sequences as shown in SEQ ID NO 31, 33, 35, and 37;
(f) a derivative of a protein or a peptide encoded by a polynucleotide of any one of (a) to (e), wherein in said derivative between 1 and 10 amino acid residues are conservatively substituted compared to said protein, and said derivative has cell protective and in particular neuroprotective activity, but essentially no hematopoietic activity;
(g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;
(h) a protein termed ha, hAmA, hAmE, hA-10 and hA-10-transport, hA-transport sequence, having the deduced amino acid sequence as shown in SEQ ID NOs 50, 51, 52, 53, 61 and 66 respectively;
(i) a protein encoded by a polynucleotide having the coding sequence, as shown in SEQ ID NOs: 55, 56, 57, 58, 60 and 65 encoding at least the mature form of the protein;
(j) a derivative of a protein of any one of (h) to (i), wherein in said derivative between 1 and 10 amino acid residues are conservatively substituted compared to said protein, and said derivative has cell protective and in particular neuroprotective activity, but essentially no hematopoietic activity;
(k) a fragment of a protein of any one of (h) to (i), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;
(l) an erythropoietin (EPO) variant encoded by a polynucleotide selected from the group consisting of:
  (1) polynucleotides, which comprise more than six amino acids from the N-terminus of mature human EPO,
  (2) polynucleotides, which comprise the N-terminal part of full length EPO including helix A and which lack at least one of the following:
    (i) a fragment of at least 10 amino acids between helix A and helix B,
    (ii) a fragment of at least 10 amino acids of helix B,
    (iii) a fragment of at least 2 amino acids between helix B and helix C,
    (iv) a fragment of at least 10 amino acids of helix C,
    (v) a fragment of at least 10 amino acids between helix C and D, and/or
    (vi) a fragment of at least 10 amino acids of helix D, wherein said variant has cell protective and in particular neuroprotective activity, but essentially no hematopoietic activity,
  (3) polynucleotides encoding a derivative of a protein encoded by a polynucleotide of any one of (a), wherein in said derivative between 1 and 10 amino acid residues are conservatively substituted compared to said protein, and said derivative has cell protective and in particular neuroprotective activity, but essentially no hematopoietic activity and,
  (4) polynucleotides, the complementary strand of which hybridizes under stringent conditions to a polynucleotide as defined in any one of (1) to (2) and which code for a protein having cell protective and in particular neuroprotective activity, but essentially no hematopoietic activity; or the complementary strand of such a polynucleotide;
(m) a derivative of a protein of any one of (a) to (l), wherein in said derivative amino acid residues are truncated from the transport sequence (SEQ ID NO 62 for amino acid sequence and SEQ ID NO 63 for polynucleotide sequence), and said derivative has cell protective and in particular neuroprotective activity, but essentially no hematopoietic activity such as, but not limited to hA without leader (SEQ ID NO 66).

Optionally one or more of the following substances is in the culture, Dulbecco's minimal essential medium and Eagle's medium, N2 medium, HEPES, neurobasal medium with B27, fetal calf serum, mercaptoethanol, L-glutamine, glutamate, nonessential amino acids, insulin, transferrin, selenium, fibronectin, polyL-lysine, gelatine, retinoic acid, penicillin, streptomycin, growth factors including, but not restricted to LIF, BDNF, CNTF, NGF, EGF, FGF-2, IL-3, IL-6, SCF, PDGF.

In this context helix A, B, C, and D of the vEPO polypeptide are regions homologous to the respective helix A, B, C, and D regions of full length EPO from mouse and human as outlined in FIG. 4. It is well known in the art how to determine homologies between two polypeptide sequences and someone of skill in the art will be capable to align a given EPO polypeptide sequence derived, e.g. from another species, and to determine the respective position of helix A, B, C, and D in this EPO polypeptide. It is preferred that the vEPO variant polynucleotide is derived from a higher eukaryote, in particular a mammal or bird. Preferred mammals are humans, non-human primates; rodents, e.g. rat, or guinea pig; ruminant, e.g. cow; or sheep; horse; pig; rabbit; dog; or cat. A larger number of such full length EPO encoding polynucleotides from various species are known, including without limitation cat (Gene Bank Acc. L10606), pig (Gene Bank Acc. 10607), sheep (Gene Bank Acc.10610), dog (Gene Bank Acc. L13027), macaque (Gene Bank Acc. M18189), rhesus monkey (Gene Bank Ace. L10609), mouse (Gene Bank Acc. 12930), rat (Gene Bank Acc. L10608), human (Gene Bank Acc. M11319), Bos taurus (Gene Bank Acc. U44762) and Bos indicus (Gene Bank Ace. L41354).

Preferably the polynucleotides encoding a vEPO variant polypeptide lack the following: (i); (ii); (iii); (iv); (v); (vi); (i) and (ii); (i) and (iii); (i) and (iv); (i) and (v); (i) and (vi); (ii) and (iii); (ii) and (iv); (ii) and (v); (ii) and (vi); (iii) and (iv); (iii) and (v); (iii) and (vi); (iv) and (v); (iv) and (vi); (v) and (vi); (i), (ii) and (iii); (i), (ii) and (iv), (i), (ii) and (v), (i), (ii), (vi), (i), (iii) and (iv); (i), (iii) and (v); (i), (iii) and (vi); (i), (iv) and (v); (i), (iv) and (vi); (i), (v) and (vi); (ii), (iii) and (iv); (ii), (iii) and (v); (ii), (iii) and (vi); (ii), (iv) and (v); (ii), (iv) and (vi); (ii), (v) and (vi); (iii), (iv) and (v); (iii), (iv) and (vi); (iii), (v) and (vi); or (iv), (v) and (vi).

Another aspect of the invention is a polypeptide having the amino acid sequence encoded by a polynucleotide of the invention or obtainable by the process mentioned below. The polypeptides of the invention include all those disclosed herein and fragments of these polypeptides, which carry between 1 and 10 N- and/or C-terminal deletions. Preferably, the deletions are less than 10, less than 9, less than 8, less than 7, less than 8, less than 7, less than 6, less than 5, less than 4, less than 3, less than 2, less than 1 amino acids. The polypeptides embraced by the invention also include fusion proteins that contain either the EPO splice variant as indicated in SEQ ID NOs 2, 4, 6, 8, 10, 12, 14, 16, 18, 20 and 22 or humanized version of 14, 16, 18, 20 and 22 or a fragment thereof as defined above fused to an unrelated amino acid sequence. The unrelated sequences can comprise additional functional domains or signal peptides. Signal peptides are described in greater detail and exemplified below.

The polypeptides can be any of those described above, but with not more than 10 (e.g. not more than: 10, nine, eight, seven, six, five, four, three, two, or one) conservative substitutions. Conservative substitutions are known in the art and typically include substitution of, e.g. one polar amino acid with another polar amino acid and one acidic amino acid with another acidic amino acid. Accordingly, conservative substitutions preferably include substitutions within the following groups of amino acids: glycine, alanine, valine, proline, isoleucine, and leucine (non polar, aliphatic side chain); aspartic acid and glutamic acid (negatively charged side chain); asparagine, glutamine, methionine, cysteine, serine and threonine (polar uncharged side chain); lysine, histidine and arginine; and phenylalanine, tryptophane and tyrosine (aromatic side chain); and lysine, arginine and histidine (positively charged side chain). It is well known in the art how to determine the effect of a given substitution, e.g. on $pK_i$ etc.

All that is required of a polypeptide having one or more conservative substitutions is that it has at least 50% (e.g. at least: 55%; 60%; 65%, 70%; 75%; 80%; 85%; 90%; 95%; 98%; 99%; 99.5%; or 100% or more) of the ability of the unaltered vEPO variant to protect neurons from damage/cell death (e.g. by apoptosis or necrosis), wherein the cell death is induced by oxygen and/or glucose deprivation, by toxic, chemical, physical, mechanical, inflammatory or radiation exposure or by viral or bacterial infection.

Both polypeptides and peptides can be produced by standard in vitro recombinant DNA techniques and in vivo transgenesis, using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook at al., *Molecular Cloning: A Laboratory Manual* (2nd Ed.) [Cold Spring Harbor Laboratory, N.Y., 1989], and Ausubel et al., Current *Protocols in Molecular Biology* [Green Publishing Associates and Wiley Interscience, N.Y., 1989].

Polypeptides and fragments of the invention also include those described above, but modified for in vivo use or for the cell culture use according to the invention by the addition, at the amino- and/or carboxyl-terminal ends, of blocking agents to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues or the amino group at the amino terminus or carboxyl group at the carboxyl terminus can be replaced with a different moiety. Likewise, the peptides can be covalently or noncovalently coupled to pharmaceutically acceptable "carrier" proteins prior to use or administration.

It is known in the prior art that the pharmacokinetic of protein drugs can be significantly altered by modification of the protein. For full length EPO it has been described that glycosylation, in particular the presence of sialic acid residues at the end of the oligosaccharide side chains, attributes to the circulation time (WO 95/05465) and that removal of sialic acid groups exposes galactose residues, which increases clearance by the liver. Therefore, one approach taken to enhance EPO circulation time was the increase in sialic acid residues. Several approaches, thus, involve the provision of additional glycosylation sites (see e.g. WO 91/05867, WO 94/09257 and WO 01/81405). Such modified EPO analogs may have at least one additional N-linked and/or O-linked carbohydrate chain. Other attempts to improve the half-life of EPO involved the addition of polyethylene glycol residues (PEG) of varying length the amino acid backbone (see e.g. WO 00/32772, WO 01/02017, WO 03/029291). Another attempt used the modification of EPO molecules with at least one N-linked and/or O-linked oligosaccharide, which were further modified with oxidation, sulfation, phosphorylation, PEGylation or a combination thereof (see WO 2005/025606). All these approaches can equally be employed to extend the half-life of the vEPO variants of the present invention and accordingly in a preferred embodiment the invention further comprises the step of modifying the vEPO variant, wherein the modification is selected from the group consisting of oxidation, sulfation, phosphorylation, addition of oligosaccharides or combinations thereof. If the addition of further N-linked or O-linked oligonucleotides is desired, it is possible to introduce them by introducing additional glycosylation sites as has been described in the prior art, e.g. at positions 30, 51, 57, 69, 88, 89, 136 and/or 138, if the respective position is present in the variant of the present invention (see WO 01/81405).

The term "isolated" polypeptide or peptide fragment as used herein refers to a polypeptide or a peptide fragment which either has no naturally-occurring counterpart or has been separated or purified from components which naturally accompany it, e.g. in tissues such as tongue, pancreas, liver, spleen, ovary, testis, muscle, joint tissue, neural tissue, gastrointestinal tissue or tumor tissue, or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide is "isolated."

An isolated polypeptide (or peptide fragment) of the invention can be obtained, for example, by extraction from a natural source (e.g. from tissues or bodily fluids); by expression of a recombinant nucleic acid encoding the polypeptide; or by chemical synthesis. A polypeptide that is produced in a cellular system different from the source from which it naturally originates is "isolated", because it will necessarily be free of components, which naturally accompany it. The degree of isolation or purity can be measured by any appropriate method, e.g. column chromatography, poly-acrylamide gel electrophoresis, or HPLC analysis.

A polypeptide that exhibits cell-protective activity is a polypeptide that has at least 50% (e.g. at least: 55%; 60%; 65%; 70%; 75%; 80%; 85%; 90%; 95%; 98%; 99%; 99.5%; or 100% or even more) of the ability of the respective vEPO variant to protect neurons from cell death, wherein cell death is induced by oxygen or glucose deprivation, by chemical or radiation exposure or by viral or bacterial infection. Assays to determine damage to cells, in particular to neuronal cells are known in the art. A suitable assay is the oxygen glucose deprivation assay described herein below. In the described assay the readout is the amount of lactate dehydrogenase activity (LDH). However, a variety of other methods exist, which allow assessing the damage induced in a cell and in particular the amount of cell death (e.g. apoptosis, necrosis). These assays include without limitation TUNEL assays, MTT-assay, life/death assay by staining (e.g. ethidium bromide and acridine orange staining), caspase assays, electron microscopy, DNA-laddering, which are all well known in the art.

A vEPO variant polypeptide that exhibits essentially no hematopoietic activity is a polypeptide, which elicits in art-known colony forming assays, an example of which is described below, at the same molar concentration as the rhEPO and wt mEPO, respectively, less than 10% of the CFU-E (colony forming unit-erythroblast), preferably less than 9%, 8%, 7%, 6%, 5%, 4%, 3%, 2%, or 1%. The respective CFU-E numbers are calculated for a given rhEPO, wt mEPO or EPO variant by subtracting from each value the number of CFU-E observed in a control reaction (without wt or EPO variant).

In the context of the polypeptides of the present invention the term "junction" refers to the site wherein two amino acids follow each other which are not consecutive in the rhEPO or mouse wt EPO and which are potentially the result of splice events or other rearrangements in the vEPO mRNA. The respective junction of the vEPO variants of the present invention can be derived from FIG. 4, e.g. is ENIT|VGQQ for hS3, VGQQ|ALLV for h1-4, VNFY|ALLV for h1-5, KRME|PWEP for hS4, ITVP|GPVG for h1-1, LNEN|NHC for h2-1, KRME|KELM for mS, LLAN|FLRG for mG3, DTFC|RRGD for mG5, KVNF|LRGK for m301 or LSEA|VHGR for mK3. (SEQ ID NOS 67-77, respectively).

The polynucleotide molecules of the invention can be synthesized in vitro (for example, by phosphoramidite-based synthesis) or can be obtained from a cell, such as the cell of a mammal.

The EPO variants termed mS, mG3, mG5, m301 and mK3 having the deduced amino acid sequence as shown in SEQ ID NOs 14, 16, 18, 20, and 22, respectively were isolated from mouse. The mouse sequence is highly homologous to the human sequence. An alignment of the amino acid sequences of EPO derived from humans and mouse is provided in FIG. 4. As is apparent the mouse sequence is distinguished from the human sequence by the lack of an alanine residue at position 8 and by the following 39 substitutions (the numbering is according to the respective amino acid position in the human EPO, the first amino acid indicated is the human amino acid at that position and the second is the corresponding mouse amino acid): $^{4}H{\rightarrow}^{4}P$; $^{6}C{\rightarrow}^{6}R$; $^{9}W{\rightarrow}^{9}T$; $^{11}W{\rightarrow}^{11}L$; $^{18}S{\rightarrow}^{18}L$; $^{19}L{\rightarrow}^{19}I$; $^{27}G{\rightarrow}^{27}C$; $^{43}L{\rightarrow}^{43}I$; $^{52}I{\rightarrow}^{52}V$; $^{54}T{\rightarrow}^{54}M$; $^{60}H{\rightarrow}^{60}G$; $^{61}C{\rightarrow}^{61}P$; $^{62}S{\rightarrow}^{62}R$; $^{64}N{\rightarrow}^{64}S$; $^{84}G{\rightarrow}^{84}E$; $^{85}Q{\rightarrow}^{85}E$; $^{95}A{\rightarrow}^{95}S$; $^{101}V{\rightarrow}^{101}I$; $^{103}R{\rightarrow}^{103}Q$; $^{104}F{\rightarrow}^{104}A$; $^{109}V{\rightarrow}^{109}A$; $^{115}W{\rightarrow}^{115}P$; $^{117}P{\rightarrow}^{117}T$; $^{122}V{\rightarrow}^{122}I$; $^{126}V{\rightarrow}^{126}I$; $^{134}T{\rightarrow}^{134}S$; $^{138}A{\rightarrow}^{138}V$; $^{145}A{\rightarrow}^{145}L$; $^{146}I{\rightarrow}^{146}M$; $^{151}A{\rightarrow}^{151}T$; $^{152}A{\rightarrow}^{152}T$; $^{153}S{\rightarrow}^{153}P$; $^{154}A{\rightarrow}^{154}P$; $^{160}I{\rightarrow}^{160}L$; $^{162}A{\rightarrow}^{162}V$; $^{166}R{\rightarrow}^{166}C$; $^{173}S{\rightarrow}^{173}A$; $^{187}A{\rightarrow}^{187}V$ and $^{190}T{\rightarrow}^{190}R$. A humanized mS, mG3, mG5, m301 or mK3 carries the additional alanine residue at position 8 and/or at one or more preferably 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 positions the human rather than the mouse amino io acid sequence. It is particularly preferred that mS, mG3, mG5, m301 and mK3 are fully humanized, i.e. that every amino acid at the above outlined positions, in as far as they are present in the respective variant, is of the human sequence rather than the mouse sequence. It is expected that the humanization of the mouse variants will diminish any immunological problems, which might be encountered when applied for the methods of the invention.

The vEPO variant nucleic acid molecules of the invention can be DNA, cDNA, genomic DNA, synthetic DNA, or, RNA, and can be double-stranded or single-stranded, the sense and/or an antisense strand. These molecules can be produced by, for example, polymerase chain reaction (PCR) or generated by treatment with one or more restriction endonucleases. A ribonucleic acid (RNA) molecule can be produced by in vitro transcription.

The polynucleotide molecules of the invention can contain naturally occurring sequences, or sequences that differ from those that occur naturally, but, due to the degeneracy of the genetic code, encode the same polypeptide, i.e. the polypeptides with SEQ ID NOs: 2, 4, 6, 8, 10, 12, 14, 16, 18, 20, and 22. In addition, these nucleic acid molecules are not limited to coding sequences, e.g. they can include some or all of the non-coding sequences that lie upstream or downstream from a coding sequence.

In addition, the isolated nucleic acid molecules of the invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses thereof are discussed further below.

In preferred embodiments, the polynucleotides of the present invention also comprise nucleic acid molecules which are at least 50%, preferably 55%, 60%, 65%, 70%, 75%, 80%, 85%/a, 86%, 87%, 88%, 89%, 90%, 91%, 92%, 93%, 94%, 95%, 96%, 97%, 98%, or 99% identical to: (a) a nucleic acid molecule that encodes the polypeptide of SEQ ID NOs: 2, 4, 6, 8, 10, 12, 14, 16, 18, 20, 22, 50, 51, 52, 53, 61 or 66 and (b) the nucleotide sequence of SEQ ID NOs: 1, 3, 5, 7, 9, 11, 13, 15, 17, 19, 21, 55, 56, 57, 58, 60 or 65, respectively, and which at the same time has cell-protective and in particular neuroprotective activity, but essentially no hematopoietic activity.

The determination of percent identity between two sequences is accomplished using the mathematical algorithm of Karlin and Altschul (1993) *Proc. Natl. Acad. Sci. USA* 90: 5873-5877. Such an algorithm is incorporated into the BLASTN and BLASTP programs of Altschul et al. (1990) J. Mol. Biol. 215: 403-410. BLAST nucleotide searches are performed with the BLASTN program, score=100, word length=12, to obtain nucleotide sequences homologous to the EPO variant polypeptide encoding nucleic acids. BLAST protein searches are performed with the BLASTP program, score=50, word length=3, to obtain amino acid sequences homologous to the EPO variant polypeptide, respectively. To obtain gapped alignments for comparative purposes, Gapped BLAST is utilized as described in Altschul et al. (1997)

Nucleic Acids Res. 25: 3389-3402. When utilizing BLAST and Gapped BLAST programs, the default parameters of the respective programs are used.

Hybridization can also be used as a measure of homology between two nucleic acid sequences. A nucleic acid sequence encoding any of the vEPO variants disclosed herein, or a derivative or fragment thereof, can be used as a hybridization probe according to standard hybridization techniques. The hybridization of a vEPO variant probe to DNA or RNA from a test source (e.g. a mammalian cell) is an indication of the presence of the relevant EPO or vEPO DNA or RNA in the test source. Hybridization conditions are known to those skilled in the art and can be found in Current Protocols in Molecular Biology, John Wiley & Sons, N.Y., 6.3.1-6.3.6, 1991. Stringent conditions are defined as equivalent to hybridization in 6× sodium chloride/sodium citrate (SSC) at 45° C., followed by a wash in 0.2×SSC, 0.1% SDS at 65° C. When selecting a probe specific for a variant carrying an internal deletion it is preferred that the probe used to detect homologous nucleic acids overlaps the boundaries of the deletion, e.g. hs3, h1-4, h1-5, hS4, mS, mG3, mG5 or m301. In cases where the splicing leads to an alternate C-terminus of the protein, e.g. h1-1, h2-1 or mK3 it is preferred that the probe used to detect homologous DNA sequences overlaps the boundaries between the known EPO sequence and the alternate C-terminus. For example, a probe could be designed, which comprises 10 complementary bases 5' of the splice site and 10 complementary bases 3' of the splice site.

An "isolated DNA" is either (1) a DNA that contains sequence not identical to that of any naturally occurring sequence, or (2) in the context of a DNA with a naturallyoccurring sequence (e.g. a cDNA or genomic DNA), a DNA free of at least one of the genes that flank the gene containing the DNA of interest in the genome of the organism, in which the gene containing the DNA of interest naturally occurs. The term therefore includes a recombinant DNA incorporated into a vector, into an autonomously replicating plasmid or virus, or into the genomic DNA of a prokaryote or eukaryote. The term also includes a separate molecule such as a cDNA, where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e. a gene encoding a nonnaturally occurring fusion protein. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

A further aspect of the present invention is a vector containing the vEPO polynucleotide(s) of the present invention or a protein encoded by a polynucleotide of the present invention for replicating the gene and/or expressing the vEPO protein in a stem cell or a progenitor cell. The term "vector" refers to a protein or a polynucleotide or a mixture thereof, which is capable of being introduced or of introducing the proteins and/or nucleic acid comprised into a stem cell or a progenitor cell. It is preferred that the proteins encoded by the introduced polynucleotide are expressed within the stem cell or progenitor upon introduction of the vector.

In a preferred embodiment, the vector of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, L.J. and Gay, E.E. (20001) Curr. Gene Therap. 1:237-251), herpes viruses, in particular Herpes simplex virus (HSV-1, Carlezon, W.A. et al. (2000) Grit. Rev. Neurobiol.), baculovirus, retrovirus, adeno-associated-virus (AAV, Carter, P. J. and Samuiski, R. J. (2000) J. Md. Med. 6:17-27), rhinovirus, human immune deficiency virus (HIV), filovirus and engineered versions thereof (see, for example, Cobinger G. P. at al, (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3:466-76 and Springer et al. (1998) Mol. Cell. 2:549-58). Most preferred vectors are adeno-associated virus, onco-retrovirus and lentivirus.

Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1, 2-Dioleyloxypropyl-3-trimethylammoniumbromid) and DPOE (Dioleoylphosphatidyl-ethanolamin) which both have been used on a variety of cell lines.

Nucleofection and electroporation are other means for the introduction of nucleic acids into cells. Nucleic acid-coated particles can be used for the introduction of nucleic acids into cells using so-called "gene guns", which allow the mechanical introduction of particles into the progenitor cells or stem cells. Preferably the particles itself are inert, and therefore, are in a preferred embodiment made out of gold spheres.

In a further aspect the polynucleotide of the present invention is operatively linked to expression control sequences allowing expression in prokaryotic and/or eukaryotic host cells. The transcriptional/translational regulatory elements referred to above include but are not limited to inducible and non-inducible, constitutive, cell cycleregulated, metabolically-regulated promoters, enhancers, operators, silencers, repressors and other elements that are known to those skilled in the art and that drive or otherwise regulate gene expression. Such regulatory elements include, but are not limited to regulatory elements directing constitutive expression like, for example, promoters transcribed by RNA polymerase III, e.g. promoters for the snRNA U6 or scRNA 7SK gene, the cytomegalovirus hCMV immediate early gene, the early or late promoters of SV40 adenovirus, viral promoter and activator sequences derived from, e.g. NBV, HCV, HSV, HPV, EBV, HTLV, MMTV or HIV; which allow inducible expression like, for example, CUP-1 promoter, the tet-repressor as employed, for example, in the tet-on or tet-off systems, the lac system, the trp system; regulatory elements directing tissue specific expression, preferably nerve cell-specific expression, e.g. promoter (e.g. Thy-1.2, NSE, prion protein, myosin light chain II, tyrosine hydroxylase, CaMKIIalpha promoter, platelet-derived growth factor beta-chain (PDGF), dopamine beta-hydroxylase, Tau, regulatory elements (e.g. NRSE/RE-1; neuron-restrictive silencing element/repressor element 1) directing cell cycle-specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or a-mating factors.

As used herein, "operatively linked" means incorporated into a genetic construct so that expression control sequences effectively control expression of a coding sequence of interest.

Similarly, the polynucleotides of the present invention can form part of a hybrid gene encoding additional polypeptide sequences, for example, a sequence, which encodes a protein that functions as a marker or reporter. The hybrid gene can lead to a fusion protein or the two or more parts can be separated by internal ribosomal entry sites (IRES) sequence, which lead to the expression of two or more separate proteins. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), green fluorescent protein (GFP) and variants thereof and xanthine guanine phosphoribosyltransferase (XGPRT). As with many of the standard procedures associated with the practice of the invention, skilled artisans will be aware of additional useful reagents, for example, additional sequences that can serve the function of a marker or reporter. If the expression of the hybrid gene leads to one polypeptide, the hybrid polypeptide will usually include a first portion and a second portion; the first portion being an EPO variant polypeptide and the second portion being, for example, the reporter described above or an Ig constant region or part of an Ig constant region, e.g. the CH2 and CH3 domains of IgG2a heavy chain. Other hybrids could include a heterologous peptide sequence to facilitate purification and/or detection, e.g. an antigenic tag-like, for example, a myc tag, or a tag with preferential binding to a region, e.g. chitin tag or His tag. Recombinant nucleic acid molecules can also contain a polynucleotide sequence encoding a vEPO variant polypeptide operatively linked to a heterologous localization sequence. Such localization sequences can direct the protein to different compartments within the cell and are well known to someone of skill in the art. A preferred localization sequence is a sequence, that facilitates secretion of the resulting protein, e.g. the naturally occurring transport sequence (SEQ ID NO 62 for amino acid sequence and SEQ ID NO 63 for polynucleotide sequence). Preferably these localization and/or tag sequences are designed in such a way, that they can be cleaved off the vEPO variant after purification to provide an essentially pure protein without too many amino acids, preferably not more than 10 additional amino acids to the final vEPO. Such cleavage sites are well known in the art and comprise, e.g endopeptidase cleavage sites and intein cleavage sites.

vEPO may be expressed in a host cell genetically engineered with the polynucleotide or the vector as outlined above. The host cells that may be used for purposes of the invention include, but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 of Hi5 cells, which can be infected with, for example, recombinant virus expression vectors (for example, baculovirus) containing the polynucleotide molecules of the invention; Xenopus oocytes, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing an EPO variant nucleotide sequence; or mammalian cell systems (for example, COS, CHO, BHK, HEK293, VERO, HeLa, MDCK, Wi38, Swiss 3T3 and NIH 3T3 cells), which can be transformed with recombinant expression constructs containing, for example, promoters derived from the genome of mammalian cells (for example, the metallothionein promoter), from mammalian viruses (for example, the adenovirus late promoter, CMV IE and the vaccinia virus 7.5K promoter) or from bacterial cells (for example, the tet-repressor binding employed in the tet-on and tet-off systems). Also useful as host cells are primary or secondary cells obtained directly from a mammal and transfected with a plasmid vector or transduced with a viral vector. Depending on the host cell and the respective vector used to introduce the polynucleotide of the invention, the polynucleotide can integrate, for example, into the chromosome or the mitochondrial DNA or can be maintained extrachromosomally like, for example, episomally or can be only transiently contained in the cells.

Since Erythropoietin is heavily glycosylated in vivo, it is desirable to choose an expression system, which provides faithful glycosylation of the protein. Consequently, it is preferred to introduce the polynucleotides encoding the vEPO splice variants of the present invention into higher eukaryotic cells, in particular into mammalian cells, such as COS, CHO, BHK, HEK293, VERO, HeLa, MDCK, Wi38, Swiss 3T3 or NIH 3T3 cells.

The nucleic acid may be in a cassette, where it is operably linked to a promoter. The promoter may be capable of driving the expression only in particular tissues or cells, such as, but not limited to neural tissue, bone marrow or tissue which exhibits inflammation or degeneration. Respective teaching may be taken from WO 97/14307.

In a preferred embodiment, the stem cell according to the invention is an embryonic, fetal or adult (postnatal-derived) stem cell selected from the group of totipotent stem cells, pluripotent stem cells, multipotent stem cells, unipotent stem cells and reprogrammed somatic cells with the capacity to self-renew and to give rise to various differentiated progeny. The progenitor cell is an immature cell with limited capacity for self-renewal and differentiation compared with the stem cell. The embodiment also includes manipulated cells, e.g. cloned cells, fused cells and reprogrammed cells. In its broadest sense, the cells according to the invention are differentiated or undifferentiated cells, such as neoplastic cells.

In a preferred embodiment the totipotent and the pluripotent stem cell is selected from the group of embryonic stem cells, embryonic germ cells and embryonal carcinoma cells, germline stem cells, including spermatogonial stem cells, or from cloned cells or from fused or in vitro reprogrammed cells.

In a further preferred embodiment the multipotent stem cell and progenitor cell is selected from the group of fetal or adult stem and progenitor cells derived from any tissue or from cloned cells or from fused or reprogrammed cells, including but not restricted to hematopoietic stem and progenitor cells, peripheral blood stem and progenitor cells, umbilical cord stem and progenitor cells, endothelial precursor cells, mesenchymal stem and progenitor cells, multipotent adult progenitor cells, neural stem and progenitor cells, glomus cells, epidermal stem and progenitor cells, intestinal stem and progenitor cells, hair follicle stem and progenitor cells, cardiac and skeletal muscle stem and progenitor cells, adipose-derived stem and progenitor cells, hepatic stem and progenitor cells, pancreatic stem and progenitor cells, neoplastic cells.

In a particularly preferred embodiment the multipotent stem cell and progenitor cell is selected from the group of multipotent adult progenitor cells and reprogrammed somatic cells.

In a most preferred embodiment the multipotent stem cell and progenitor cell is selected from the group of neural stem and progenitor cells, hematopoietic stem and progenitor cells and mesenchymal (stromal) stem and progenitor cells.

In a preferred embodiment, the adult stem and progenitor cells are derived from the following tissues or from the following fused or reprogrammed cells: skeletal muscle, liver, skin and hair follicle, glomus, testis/ovaries.

In another preferred embodiment, stem and progenitor cells are obtained from embryonic/fetal tissue.

In a more preferred embodiment, adult stem and progenitor cells are derived from the following tissues or from the following fused or reprogrammed cells: nervous system; bone marrow, peripheral blood, umbilical cord, placenta, adipose tissue; pancreas, heart.

In one embodiment of the method, the vEPO protein is an erythropoietin (EPO) variant, which is a homologue of an erythropoietin (EPO) variant from another higher eukaryotic species.

In one embodiment, the differentiated cells are segregated from the undifferentiated or less differentiated stem and progenitor cells.

It is preferred, that the cells are segregated by immunoaffinity separation or dye exclusion.

In one embodiment, the immunoaffinity separation is performed using a selection element having an antibody of fragment thereof selected from the group of (or homologues): Oct3/4, Nanog, Sox2, Utf1, Esg1, Rex1, FoxD3, Utf1, Tdgf1, LeftB, Left1, Tcf4, Dsh, Lin28, Dnmt3B, Smoothened, SMO, Gdf3, Gja1, Notch1, Manic Fringe, Tal1, Lmo2, Hox A9, Meis-1, GcnS, Sirt2, Atrx, TGIF, Enx1, Tal1, Lmo2, Bmi1, Bmp4, Meis1, Lhx2, CyclinD1, CyclinG2, MDR1, Osteopontin, LIFR, AA4.1, CLQR1, IFI16, JAK3, FZD6, StraB, Islet-1, Gata4, Nkx2.5, Mef2c, alpha-MHC, 2v, MyoD, SM alpha-actin, VSM-MHC, Pecam1, Flk1, Flt1, VWF, Nestin, GFAP, Synaptophysin, GAD, Calbindin, TH, TPH, ChAT, VGLUT1, VGLUT2, Drd2, Afp, Krt1-18, Krt1-10, CD45, Ly6C/G, Mac-1, CD19, CD3, CD4, CD8, CD17, CD25, FoxP3, CD11c, CD13, c-Kit, CD34, Sca-1, MHCI, MHCII, CD44, SSEA-1, Ter119, Thy1, CD31, CD62E, CD133, Otx1, Otx2, Pax2, Pax5, Pax6, Doublecortin, class III beta-Tubulin, MAP2, Neurofilament, NeuN, Calretinin, GalC, NG2, Iba1, CD11b, F4/80, CCR2, MBP, MOG.

The invention relates to a method of treating an individual with an acute or chronic degenerative, inflammatory or other disorder leading to cell loss and/or tissue dysfunction, wherein the individual is treated with vEPO or cells expressing a vEPO protein variant according to the invention due to the presence of an exogenous copy of a nucleic acid encoding a vEPO protein in order to support and enhance regeneration by endogenous stem and progenitor cells populations. In a preferred embodiment, the invention relates to a method of increasing the number, viability and/or differentiation of neural, hematopoietic and mesenchymal (stromal) stem and progenitor cells in an individual, comprising administering to an individual in need of such treatment a vEPO variant selected from the group consisting of:
(a) proteins termed hs3, h1-4, h1-5, hs4, h1-1, h2-1, mS, mG3, mG5, m301 and mK3 having the deduced amino acid sequence as shown in SEQ ID NOs 2, 4, 6, 8, 10, 12, 14, 16, 18, 20, and 22, respectively;
(b) proteins encoded by polynucleotides having the coding sequence as shown in SEQ ID NOs: 1, 3, 5, 7, 9, 11, 13, 15, 17, 19, and 21 encoding at least the mature form of the protein;
(c) proteins encoded by a polynucleotide encoding a humanized version of the proteins mS, mG3, mG5, m301 and mK3 having the deduced amino acid sequence as shown in SEQ ID NOs 14, 16, 18, 20, and 22;
(d) a protein comprising a fusion of an amino acid sequence selected from the group of amino acid sequences as shown in SEQ ID NO 24, 26, 28, and 30, at the N-terminus of an amino acid sequence selected from the group of amino acid sequences as shown in SEQ ID NO 32, 34, 36, and 38;
(e) a protein encoded by a polynucleotide comprising a fusion of polynucleotide sequences selected from the group of polynucleotide sequences as shown in SEQ ID NO 23, 25, 27, and 29, 5' of a polynucleotide sequence selected from the group of polynucleotide sequences as shown in SEQ ID NO 31, 33, 35, and 37;
(f) a derivative of a protein or a peptide encoded by a polynucleotide of any one of (a) to (e), wherein in said derivative between 1 and 10 amino acid residues are conservatively substituted compared to said protein, and said derivative has cell protective and in particular neuroprotective activity, but essentially no hematopoietic activity;
(g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;
(h) a protein termed ha, hAmA, hAmE, hA-10 and hA-10-transport, hA-transport sequence, having the deduced amino acid sequence as shown in SEQ ID NOs 50, 51, 52, 53, 61 and 66 respectively;
(i) a protein encoded by a polynucleotide having the coding sequence, as shown in SEQ ID NOs: 55, 56, 57, 58, 60 and 65 encoding at least the mature form of the protein;
(j) a derivative of a protein of any one of (h) to (i), wherein in said derivative between 1 and 10 amino acid residues are conservatively substituted compared to said protein, and said derivative has cell protective and in particular neuroprotective activity, but essentially no hematopoietic activity;
(k) a fragment of a protein of any one of (h) to (i), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;
(l) an erythropoietin (EPO) variant encoded by a polynucleotide selected from the group consisting of:
(1) polynucleotides, which comprise more than six amino acids from the N-terminus of mature human EPO,
(2) polynucleotides, which comprise the N-terminal part of full length EPO including helix A and which lack at least one of the following:
(i) a fragment of at least 10 amino acids between helix A and helix B, (ii) a fragment of at least 10 amino acids of helix B,
(iii) a fragment of at least 2 amino acids between helix B and helix C,
(iv) a fragment of at least 10 amino acids of helix C,
(v) a fragment of at least 10 amino acids between helix C and D, and/or
(vi) a fragment of at least 10 amino acids of helix D, wherein said variant has cell protective and in particular neuroprotective activity, but essentially no hematopoietic activity,
(3) polynucleotides encoding a derivative of a protein encoded by a polynucleotide of any one of (a), wherein in said derivative between 1 and 10 amino acid residues are conservatively substituted compared to said protein, and said derivative has cell protective and in particular neuroprotective activity, but essentially no hematopoietic activity and, (4) polynucleotides, the complementary strand of which hybridizes under stringent conditions to a polynucleotide as defined in any one of (1) to (2) and which code for a protein having cell protective and in particular neuroprotective activity, but essentially no hematopoietic activity; or the complementary strand of such a polynucleotide;

(m) a derivative of a protein of any one of (a) to (l), wherein in said derivative amino acid residues are truncated from the transport sequence (SEQ ID NO 62 for amino acid sequence and SEQ ID NO 63 for polynucleotide sequence), and said derivative has cell protective and in particular neuroprotective activity, but essentially no hematopoietic activity such as, but not limited to hA without leader (SEQ ID NO 66).

Likewise, the invention relates to use of the vEPO nucleic acids and/or vEPO peptides and proteins for the production of a medicament for increasing the number of neural, hematopoietic and/or mesenchymal (stromal) stem and/or progenitor cells in an individual.

The invention relates to a method of treating an individual with an acute or chronic degenerative, inflammatory or other disorder leading to cell loss or tissue dysfunction, wherein the individual is treated by transplanting stem or progenitor cells, wherein i) the stem or progenitor cells are pre-incubated in a cell culture comprising a vEPO protein variant prior to transplantation and/or, ii) the stem or progenitor cells express the vEPO protein variant due to the presence of an exogenous copy of a nucleic acid encoding a vEPO protein and/or, iii) the stem or progenitor cells are transplanted and the vEPO protein variant is administered shortly before the transplant, shortly after the transplant or together with the transplant, wherein the vEPO protein variant selected from the group consisting of:

(a) proteins termed hs3, h1-4, h1-5, hs4, h1-1, h2-1, mS, mG3, mG5, m301 and mK3 having the deduced amino acid sequence as shown in SEQ ID NOs 2, 4, 6, 8, 10, 12, 14, 16, 18, 20, and 22, respectively;

(b) proteins encoded by polynucleotides having the coding sequence as shown in SEQ ID NOs: 1, 3, 5, 7, 9, 11, 13, 15, 17, 19, and 21 encoding at least the mature form of the protein;

(c) proteins encoded by a polynucleotide encoding a humanized version of the proteins mS, mG3, mG5, m301 and mK3 having the deduced amino acid sequence as shown in SEQ ID NOs 14, 16, 18, 20, and 22;

(d) a protein comprising a fusion of an amino acid sequence selected from the group of amino acid sequences as shown in SEQ ID NO 24, 26, 28, and 30, at the N-terminus of an amino acid sequence selected from the group of amino acid sequences as shown in SEQ ID NO 32, 34, 36, and 38;

(e) a protein encoded by a polynucleotide comprising a fusion of polynucleotide sequences selected from the group of polynucleotide sequences as shown in SEQ ID NO 23, 25, 27, and 29, 5' of a polynucleotide sequence selected from the group of polynucleotide sequences as shown in SEQ ID NO 31, 33, 35, and 37;

(f) a derivative of a protein or a peptide encoded by a polynucleotide of any one of (a) to (e), wherein in said derivative between 1 and 10 amino acid residues are conservatively substituted compared to said protein, and said derivative has cell protective and in particular neuroprotective activity, but essentially no hematopoietic activity;

(g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;

(h) a protein termed ha, hAmA, hAmE, hA-10 and hA-10-transport, hA-transport sequence, having the deduced amino acid sequence as shown in SEQ ID NOs 50, 51, 52, 53, 61 and 66 respectively;

(i) a protein encoded by a polynucleotide having the coding sequence, as shown in SEQ ID NOs: 55, 56, 57, 58, 60 and 65 encoding at least the mature form of the protein;

(j) a derivative of a protein of any one of (h) to (i), wherein in said derivative between 1 and 10 amino acid residues are conservatively substituted compared to said protein, and said derivative has cell protective and in particular neuroprotective activity, but essentially no hematopoietic activity;

(k) a fragment of a protein of any one of (h) to (i), wherein in said fragment between 1 and 10 amino acid residues are N- and/or C-terminally deleted and/or between 1 and 10 amino acids are deleted N- and or C-terminally of the junction compared to said protein, and said fragment has cell protective and in particular neuroprotective activity, but essentially no hematopoietic activity;

(l) an erythropoietin (EPO) variant encoded by a polynucleotide selected from the group consisting of:

(1) polynucleotides, which comprise more than six amino acids from the N-terminus of mature human EPO, (2) polynucleotides, which comprise the N-terminal part of full length EPO including helix A and which lack at least one of the following:

(i) a fragment of at least 10 amino acids between helix A and helix B, (ii) a fragment of at least 10 amino acids of helix B, (iii) a fragment of at least 2 amino acids between helix B and helix C, (iv) a fragment of at least 10 amino acids of helix C, (v) a fragment of at least 10 amino acids between helix C and D, and/or (vi) a fragment of at least 10 amino acids of helix D, wherein said variant has cell protective and in particular neuroprotective activity, but essentially no hematopoietic activity, (3) polynucleotides encoding a derivative of a protein encoded by a polynucleotide of any one of (a), wherein in said derivative between 1 and 10 amino acid residues are conservatively substituted compared to said protein, and said derivative has cell protective and in particular neuroprotective activity, but essentially no hematopoietic activity and, (4) polynucleotides, the complementary strand of which hybridizes under stringent conditions to a polynucleotide as defined in any one of (1) to (2) and which code for a protein having cell protective and in particular neuroprotective activity, but essentially no hematopoietic activity; or the complementary strand of such a polynucleotide;

(m) a derivative of a protein of any one of (a) to (l), wherein in said derivative amino acid residues are truncated from the transport sequence (SEQ ID NO 62 for amino acid sequence and SEQ ID NO 63 for polynucleotide sequence), and said derivative has cell protective and in particular neuroprotective activity, but essentially no hematopoietic activity such as, but not limited to hA without leader (SEQ ID NO 66).

In a preferred embodiment, said acute or chronic degenerative disorder and/or inflammatory disorder or neoplasia, is an acute or chronic disorder of the central and peripheral nervous system, sensory organs, skeletal and cardiac muscle, smooth muscle, vasculature, lung, liver, pancreas, upper and lower GI tract, kidneys and urinary tract, prostate, hematopoietic system, immune system, reproductive organs, bone and joints or said condition is associated with an organ or cell transplantation.

The stem or progenitor cells are transplanted and a vEPO protein variant is administered shortly before the transplant, shortly after the transplant or together with the transplant. Thus, likewise the invention relates to use of the vEPO nucleic acids and/or vEPO peptides and proteins according to the invention for the production of a formula for the treatment of an acute or chronic degenerative, inflammatory or other disorder leading to cell loss or tissue dysfunction in this context. A pharmaceutical composition will encompass a stem or progenitor cell and a vEPO protein or peptide.

In one embodiment, the said acute or chronic degenerative disorder, inflammatory or other disorder leading to cell loss or tissue dysfunction, is an acute or chronic disorder of the central and peripheral nervous system, sensory organs, skeletal and cardiac muscle, smooth muscle, vasculature, lung, liver, pancreas, upper and lower GI tract, kidneys and urinary tract, prostate, hematopoietic system, immune system, reproductive organs, bone and joints or said condition is associated with an organ or cell transplantation or neoplasia.

In an embodiment of the invention, the said condition may be selected from cerebral ischemia/hypoxia, multiple sclerosis, epilepsy, CNS infections, neurodegenerative disorders (e.g. Alzheimer's disease, Parkinson's disease, Huntington's disease, multi-system atrophy, ALS, spinocerebellar ataxias), movement disorders, cerebral palsy and other paralytical disorders, (poly)neuritis/neuropathy, chronic fatigue syndrome, chronic pain, headache, mental and behavioural disorders due to psychoactive substance use, affective disorders, schizophrenia, mental retardation, retinal degeneration, glaucoma, optic neuritis, cataract, hearing loss, loss of taste and smell, tinnitus, muscle wasting, myopathy, mitochondriopathy, inflammatory muscle disease, myasthenia, rheumatic fever, cardiac valve diseases, hypertension and hypertensive diseases, angina pectoris, myocardial infarction, endo-/peri-/myocarditis, cardiomyopathy, bronchitis, pneumonia, chronic obstructive pulmonary disease, asthma, interstitial pulmonary diseases, atherosclerosis, embolism/thrombosis, vasculitis, Crohn's, ulcerative colitis, vascular disorders of intestine, alcoholic and toxic liver disease, hepatitis, fatty liver, liver cirrhosis, cholelithiasis, cholecystitis, pancreatitis, diabetes mellitus, malabsorption, dermatitis, alopecia, acne, vitiligo, urticaria, psoriasis, lichen, inflammatory polyarthropathies, connective tissue disorders, rheumatoid disorders, dorsopathies, spondylopathies, arthrosis, osteoporosis, osteomyelitis, pyelonephritis, glomerular diseases, renal failure, urolithiasis, hyperplasia of the prostate, prostatitis, endometriosis, amenorrhea, infertility, complications during childbirth, birth trauma, Respiratory and cardiovascular disorders specific to the perinatal period, traumatic tissue damage, neoplasms, anemias, hypothyroidism, hyperthyroidism, thyroiditis, hypoparathyroidism, hyperthyroisism, malnutrition and metabolic disorders.

In a preferred embodiment, the said acute or chronic degenerative disorder, inflammatory or other disorder leading to cell loss or tissue dysfunction is epilepsy, ALS, spinocerebellar ataxics, (poly)neuritis/neuropathy, glaucoma, hearing loss, mental and behavioural disorders due to psychoactive substance use, affective disorders, schizophrenia, atherosclerosis, rheumatoid disorders.

In a preferred embodiment, the stem or progenitor cells migrate to the lesioned or damaged areas of the brain of the subject cases, where the acute or chronic neurodegenerative disorder and/or neuroinflammatory disorder involves the brain.

In the most preferred embodiment, the said acute or chronic degenerative disorder, inflammatory or other disorder leading to cell loss or tissue dysfunction is cerebral ischemia/hypoxia, retinal degeneration, dementia, multiple sclerosis, movement disorders, cardiac ischemic/hypoxia, hematological disorders and diabetes mellitus.

The activity (in units) of EPO polypeptide is traditionally defined based on its effectiveness in stimulating red cell production in rodent models (and as derived by international standards of EPO). One unit (U) of regular EPO (MW of about 34,000 Da) is about 10 ng of protein (1 mg protein is approximately 100,000 U). However, as mentioned the invention involves the use of non-hematopoietic forms of erythropoietin, and as such, this definition based on hematopoietic activity is inappropriate. Thus, as used herein, the activity unit of vEPO variant is defined as the amount of protein required to elicit the same cytoprotective activity in neural or other erythropoietinresponsive cellular systems as is elicited by native EPO in the same system.

In the practice of one aspect of the present invention, a pharmaceutical composition as described above (stem or progenitor cell and vEPO variant) may be administered to a mammal by any route, which provides a sufficient level of an erythropoietin variant. It can be administered systemically or locally. Such administration may be parenterally, transmucosally, e.g. orally, nasally, rectally, intravaginally, sublingually, submucosally, or transdermally. Preferably, administration is parenteral, e.g. via intravenous or intraperitoneal injection, and also including, but not limited to, intraarterial, intramuscular, transdermal and subcutaneous administration. If the pharmaceutical composition of the present invention is administered locally, it can be injected directly into the organ or tissue to be treated. In cases of treating the nervous system, this administration route includes, but is not limited to, the intracerebral, intraventricular, intracerebroventricular, intrathecal, intracisternal, intraspinal and/or pen-spinal, epidural routes of administration, which can employ intracranial and intravertebral needles, and catheters with or without pump devices.

In a preferred embodiment, a pharmaceutical composition comprises a vEPO variant polypeptide in a dosage unit form adapted for protection or enhancement of vEPO-responsive cells, tissues or organs, which comprises, per dosage unit, an effective non-toxic amount within the range from about 0.5 mg to 5 mg of vEPO variants; 0.6 mg to 5 mg of vEPO variants; 0.7 mg to 5 mg of vEPO variants; 0.8 mg to 5 mg of vEPO variants; 0.9 mg to 5 mg of vEPO variants; 1 to 5 mg of vEPO variants; 1.5 to 5 mg of vEPO variants; 2 to 5 mg of vEPO variants; 2.5 to 5 mg of vEPO variants; 3.5 to 5 mg of vEPO variants; 4 mg to 5 mg of vEPO variants; or 4.5 to 5 mg of vEPO variants and a pharmaceutically acceptable carrier.

In a preferred embodiment, a vEPO variant polypeptide may be administered systemically at a dosage between 100 nanograms to about 50 micrograms per kg body weight, preferably about 20 micrograms to about 50 micrograms per kg body weight. Relevant serum levels may be achieved at about 1, 2, 3, 4, 5, 6, 7, 8, 9, or 10 hours post-administration. Such dosages may be repeated as necessary. For example, administration may be repeated daily, or every other, third, fourth, fifth, sixth, or seventh day, as long as clinically necessary, or after an appropriate interval, e.g. every 1 to 12 weeks, preferably, every 3 to 8 weeks. In one embodiment, the effective amount of vEPO variant and a pharmaceutically acceptable carrier may be packaged in a single dose vial or other container. Depending on the respectively treated disease or condition, the vEPO variant can be administered in a single dose for a predetermined period of time or continuously. When an acute condition or disease is treated, it might be sufficient to provide the patient with a single dose of vEPO variant or provide vEPO for a period of, e.g. 2 days to 12 months, preferably 1 week to 6 months, more preferably 2 weeks to 3 months. If the vEPO variant of the present invention is administered for a given time period or continuously, it is preferably administered in the intervals and preferred intervals indicated above. The intervals necessary will depend in part on the serum level of the vEPO variant necessary to treat or ameliorate the respective disease and on the pharmacokinetic of the respective vEPO variant, which will in part depend on modifications of vEPO by, for example, PEG. It will be in the discretion of the practitioner to determine the exact duration, dose and type of EPO variant taking into consideration, e.g. the condition of the patient to be treated, the severity of the condition etc.

For other routes of administration, such as by use of a perfusate, injection into an organ, or other local administration, a pharmaceutical composition will be provided, which results in similar levels of a vEPO variant as described above. A level of about 10 pg/ml to about 1000 ng/ml is desired.

The pharmaceutical compositions may comprise a therapeutically effective amount of a compound, e.g. polynucleotide, polypeptide, cell or vector, and a pharmaceutically acceptable carrier. In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semisolid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g. glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g. in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g. nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g. sterile saline solution for injections, immediately prior to use. Extemporaneous injection solutions and suspensions may be prepared from sterile powders, granules and tablets. In one embodiment, an autoinjector comprising an injectable solution of an EPO variant may be provided for emergency use by ambulances, emergency rooms, and battlefield situations, and even for selfadministration in a domestic setting, particularly where the possibility of traumatic amputation may occur, such as by imprudent use of a lawn mower. The likelihood that cells and tissues in a severed foot or toe will survive after reattachment may be increased by administering an EPO variant to multiple sites in the severed part as soon as practicable, even before the arrival of medical personnel on site, or arrival of the afflicted individual with severed toe in tow at the emergency room.

Typically, compositions for intravenous administration are solutions in sterile isotonic aqueous buffer. Where necessary, the composition may also include a solubilizing agent and a local anaesthetic, such as lidocaine, to ease pain at the site of the injection. Generally, the ingredients are supplied either separately or mixed together in unit dosage form, for example, as a dry lyophilized powder or water-free concentrate in a hermetically-sealed container, such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided, so that the ingredients may be mixed prior to administration.

Suppositories generally contain active ingredient in the range of 0.5% to 10% by weight; oral formulations preferably contain 10% to 95% active ingredient.

The vEPO variant can be delivered in a controlled-release system. For example, the polypeptide may be administered using intravenous infusion, an implantable osmotic pump, a transdermal patch, liposomes, or other modes of administration. In one embodiment, a pump may be used (see Sefton (1987) *CRC Crit. Ref. Biomed. Eng.* 14: 201; Buchwald et al. (1980) *Surgery* 88:507; Saudek et al. (1989) *N. Eng. J. Med.* 321: 574). In another embodiment, the compound can be delivered in a vesicle, in particular a liposome (see Langer (1990) *Science* 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23: 61; see also Levy et at (1985) *Science* 228:190; During et al. (1989) *Ann. Neurol.* 25: 351; Howard et al. (1989) *J. Neurosurg.* 71: 105).

In yet another embodiment, a controlled release system can be placed in proximity of the therapeutic target, i.e. the target cells, tissue or organ, thus requiring only a fraction of the systemic dose (see, e.g. Goodson (1984) 115-138 in Medical Applications of Controlled Release, vol. 2). Other controlled-release systems are discussed in the review by Langer (1990, *Science* 249: 1527-1533).

In another embodiment, EPO variant, as properly formulated, can be administered by nasal, oral, rectal, vaginal, or sublingual administration.

In a specific embodiment, it may be desirable to administer the pharmaceutical compositions of the invention locally to the area in need of treatment; this may be achieved by, for example and not by way of limitation, local infusion during surgery, topical application, e.g. in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors, which will be known to one of ordinary skill in the art. Such factors include the particular form of the pharmaceutic composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g. depending upon the condition and the immune status of the individual patient, according to standard clinical techniques.

in another aspect of the invention, a perfusate or perfusion solution is provided for perfusion and storage of organs for transplant, the perfusion solution including an amount of an pharmaceutic compositions effective to protect vEPO variant-esponsive cells and associated cells, tissues or organs.

Transplant includes autologous transplantation, allogeneic transplantation and xenotransplantation, where an organ (including cells, tissue or other bodily part) or stem/progenitor cells are harvested from the recipient, from another donor of the same species or from another species, respectively. Organs can be taken from one part of a body and replaced at another, including bench surgical procedures, in which an organ may be removed, and while ex vivo, resected, repaired, or otherwise manipulated, such as for tumor removal, and then returned to the original location. In one embodiment, the perfusion solution is the University of Wisconsin (UW) solution (U.S. Pat. No. 4,798,824), which contains from about 1 to about 25 U/ml erythropoietin, 5% hydroxyethyl starch (having a molecular weight of from about 200,000 to about 300,000 and substantially free of ethylene glycol, ethylene chlorohydrin, sodium chloride and acetone); 25 mM $KH_2PO_4$; 3 mM glutathione; 5 mM adenosine; 10 mM glucose; 10 mM HEPES buffer; 5 mM magnesium gluconate; 1.5 mM $CaCl_2$. 105 mM sodium gluconate; 200,000 units penicillin; 40 units insulin; 16 mg Dexamethasone; 12 mg Phenol Red; and has a pH of 7.4-7.5 and an osmolality of about 320 mOSm/1. The solution is used to maintain cadaveric kidneys and pancreases prior to transplant. Using the solution, preservation may be extended beyond the 30-hour limit recommended for cadaveric kidney preservation. This particular perfusate is merely illustrative of a number of such solutions that may be adapted for the present use by inclusion of an effective amount of the pharmaceutical composition. In a further embodiment, the perfusate solution contains the equivalent from about 5 to about 35 U/ml erythropoietin, or from about 10 to about 30 U/ml erythropoietin. In a preferred embodiment, the solution contains 10 pg/ml to about 1000 ng/ml of vEPO protein. For the transplantation of stem or progenitor cells, these can be resuspended in saline solution containing 10 pg/ml to about 1000 ng/ml of vEPO protein and 10,000-50 million stem/progenitor cells.

While the preferred recipient of a vEPO variant for the purposes herein throughout is a human, the methods herein apply equally to other mammals, particularly domesticated animals, livestock, companion and zoo animals. However, the invention is not so limiting and the benefits may be applied to any mammal.

In preferred embodiments, the invention relates to: A method of treatment with vEPO wherein either stem cells or progenitor have been transfected using, e.g. electroporation, a gene gun, nucleofection, lipofection, magnetofection or have been transduced (virus-mediated gene delivery) with a nucleic acid encoding a vEPO protein.

The invention relates to the use of vEPO for supporting cells in co-culture transfected or transduced with nucleic acid encoding a vEPO.

The invention relates to the use of vEPO for administration to stem cells and progenitor cells ex vivo.

The invention relates to the use of nucleic acid encoding a vEPO protein for transfection or transduction of endogenous stem cells or progenitor cells or supportive somatic cells or cells of the immune system.

The invention relates to the use of a vEPO protein for administration to endogenous stem cells and progenitor cells or supportive somatic cells or cells of the immune system in vivo.

The invention relates to the use of a vEPO protein for co-administration with stem cells or progenitor cells during transplantation in vivo.

The invention relates to the use of a nucleic acid encoding a vEPO protein for transfection or transduction of somatic cells obtained from tissues, into which stem cells and/or progenitor cells are transplanted or home to after administration in vivo; the invention relates to the use of a nucleic acid encoding a vEPO protein variant for transduction or transfection of stem cells and progenitor cells used for co-transplantation.

BRIEF DESCRIPTION OF THE FIGURES AND DRAWINGS

FIG. 1: Comparison of EPO PCR products: Panel A depicts the DNA products of various PCR reactions performed with either pure plasmid comprising the different murine vEPO variants or cDNA from mouse brain or kidney, which are separated on a 1.2% agarose gel. From the left to the right the lanes comprise: 1 kb molecular weight marker, the product of pure mK3, pure mG3, pure mG5, pure m301, pure mS, pure mWT, brain cDNA, kidney cDNA. Panel B depicts the DNA product of a PCR performed with cDNA from human kidney. From the left to the right the lanes comprise 1 kb molecular weight standard and the PCR product of human kidney cDNA.

FIG. 2: Alignment of nucleotide sequences of the vEPO variants (SEQ ID NOS 13, 15, 17, 19, and 21, respectively, in order of appearance) identified in murine brain and kidney cDNA and "wild type" murine EPO (SEQ ID NO: 78), i.e. the sequence of the previously described EPO.

FIG. 3: Alignment of nucleotide sequences of the vEPO variants (SEQ ID NOS 1, 3, 5, 7, 9, and 11, respectively, in order of appearance) identified in human brain and/or kidney cDNA and "wild type" human EPO (SEQ ID NO: 79) (WT). At position 418, we found a sequence polymorphism, which is known from the public databases: in our WT and vEPO variants, we determined at this position a guanine G (please compare NM_000799.2 and SEQ ID No. 64) instead of a cytosine C (please compare X02157.1). The latter sequence leads to an amino acid change of the EPO sequence at position 140: Arginine (please compare CAA26094.1) instead of Glycine (please compare NM_000790.2).

FIG. 4: Alignment of the amino acid sequences of the vEPO variants identified in mouse (SEQ ID NOS 14, 16, 18, 20, and 22, respectively, in order of appearance) and human (SEQ ID NOS 2, 4, 6, 8, 10, and 12, respectively, in order of appearance) with the respective "wild type" Erythropoietin (mWT, hWT (SEQ ID NOS 81 and 80, respectively)). For sequence variability at position 140 of the amino sequence (WT sequence numbering), please see legend to FIG. 3.

FIG. 5: Hematopoietic activity of murine and human Erythropoietin and the vEPO variants of the present invention. Panel A depicts the results of a colony forming assay cfu-E for 150 U/l murine Erythropoietin (mEPO), human recombinant Erythropoietin (rhEPO) and comparable protein concentrations of murine vEPO variants (Splice, G3 variant) and Panel B depicts the results of a colony forming assay for human Erythropoietin (rhEPO) and vEPO variants (hS3, hS4).

FIG. 6: Experimental setup for neuroprotection assays with rhEPO (Erythropoietin) and vEPO-variants.

FIG. 7: Panel A shows an experiment with 1 h 40 min and 1 h 50 min duration of oxygen glucose deprivation (OGD). At both time-points, a protection rate of 40-50% was observed for the murine vEPO variants (Splice, G3), but no protection was detected for mEPO and rhEPO. Panel B shows an experiment with two different time-points (OGD duration varied between the two experiments according to the density of neurons). At 2 h 45 min, only weak protection was achieved with rhEPO or mEPO (20-30%) compared to murine vEPO variants (60-70%). Full protection capacity of rh EPO was only observed at higher levels of damage (3 h 15 min), where murine vEPO variants still showed neuroprotection of ~60%. All concentrations are in U/l or comparable protein concentrations of vEPO variants.

FIG. 8: Panel A shows an experiment with 2 h 00 min, 2 h 15 min and 2 h 20 min of OGD duration with a protein concentration equalling 100 U/l hEPO and comparable concentrations of human vEPO variants (hS3, hS4). At 2 h 20 min, a protection rate of 60-70% was observed for the human vEPO variants and for hEPO. Panel B shows an experiment with with 2 h 05 min, 2 h 10 min and 2 h 15 min of OGD duration with a protein concentration equalling 25 U/l hEPO and comparable concentrations of human vEPO variants (hS3, hS4). At 2 h 15 min, a protection rate of 50-70% was observed for the human vEPO variants and for hEPO.

Figure 9A:
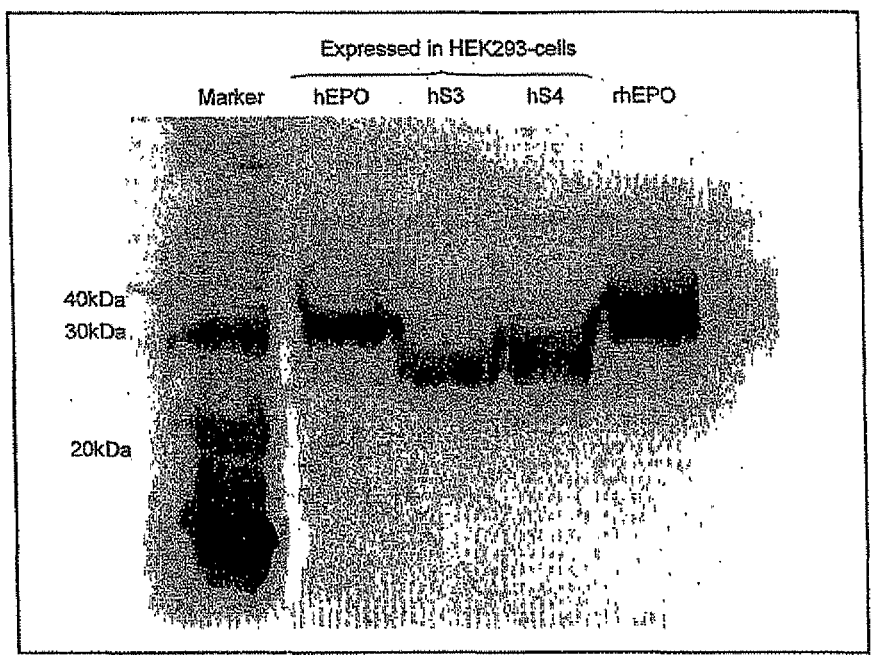

FIG. 9: Panel A shows a Western Blot from medium of HEK293-cells transfected with pcDNA3.1-V5/His-hEPO, pcDNA3.1-V5/His-hS3 or pcDNA3.1-V5/His-hS4, respectively. These media were used for experiments shown in FIG. 8. Concentration of hEPO, quantified by the mouse-EPO-ELISA (R&D) was 2U/ml. rhEPO (=2.5 ng were loaded on the gel), hEPO (=0.4 ng were loaded on the gel), hS3 and hS4: each 20 µl medium (collected 2 days after transfection). Marker=5 µl BenchMark™ His-tagged Protein Standard (Invitrogen). Panel B shows a Western Blot of His-Tag-purified mouse wild type EPO (mEPO), and different fractions of His-Tag-purified human hS3 and hS4 vEPO variants. mEPO was quantified with the EPO-mouse-ELISA. 130 pg mEPO were loaded onto the gel. (primary antibody: rabbit anti-rhEPO; Santa-Cruz).

Figure 10:
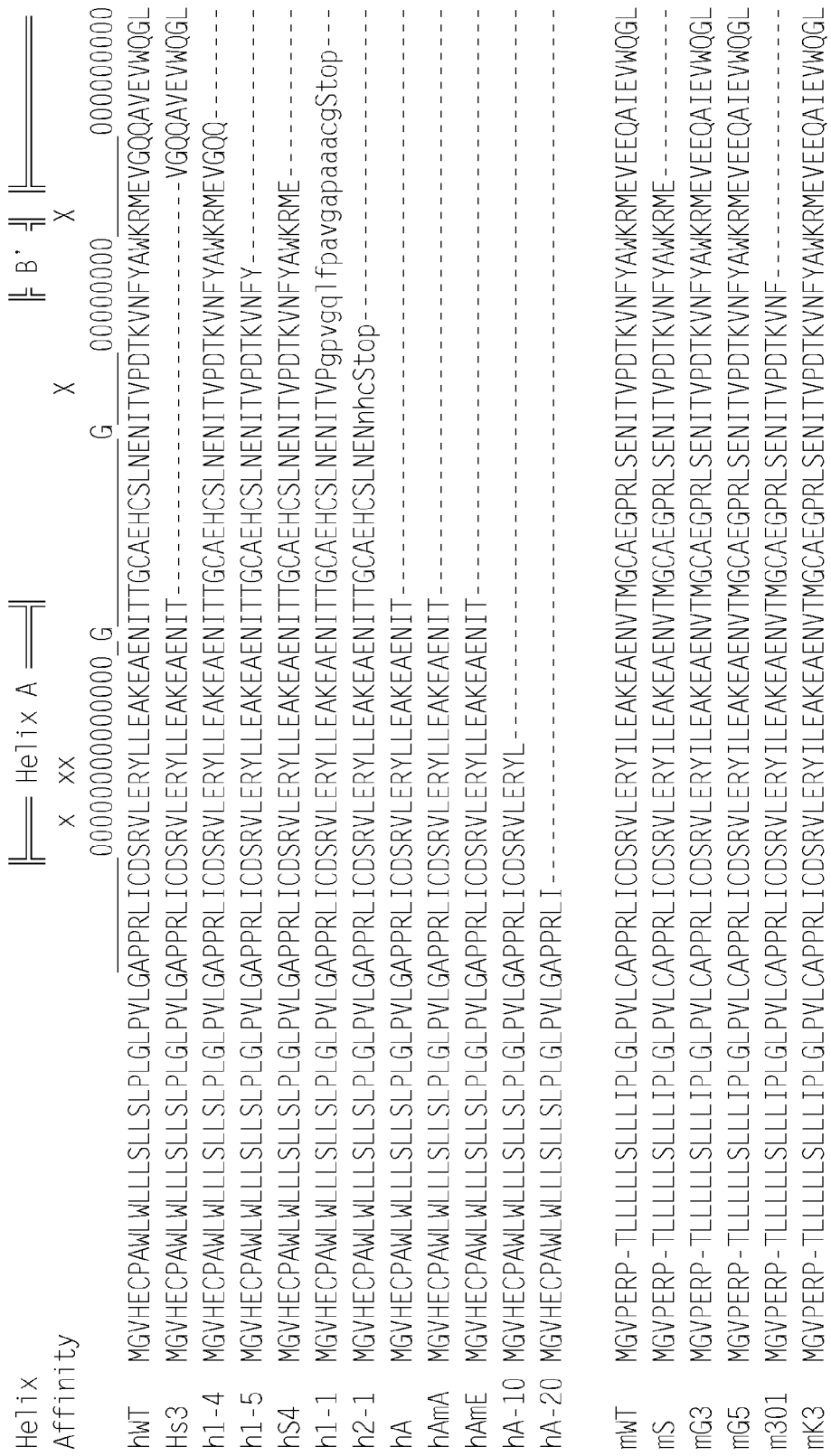

FIG. 10: Alignment of the amino acid sequences of the vEPO variants created recombinantly (alpha-helix mutants) and identified in vivo. Herein SEQ ID NO 50 is the human alpha helix wild type sequence; SEQ ID NO 51 is hAmA (point mutation Alanin); SEQ ID NO 52 is hAmE (point mutation glutamic acid); SEQ ID NO 53 is hA-10(deletion mutant) and SEQ ID NO 54 is hA-20 (deletion mutant). FIG. 10 also discloses 'hWT' as SEQ ID NO: 80, 'hS3' as SEQ ID NO: 2, 'h1-4' as SEQ ID NO: 4, 'h1-5' as SEQ ID NO: 6, 'hS4' as SEQ ID NO: 8, 'h1-1' as SEQ ID NO: 10, 'h2-1' as SEQ ID NO: 12, 'mWT' as SEQ ID NO: 81, 'mS' as SEQ ID NO: 14, 'mG3' as SEQ ID NO: 16, 'mG5' as SEQ ID NO: 18, 'm30l' as SEQ ID NO: 20, and 'mK3' as SEQ ID NO: 22.

Figure 11:
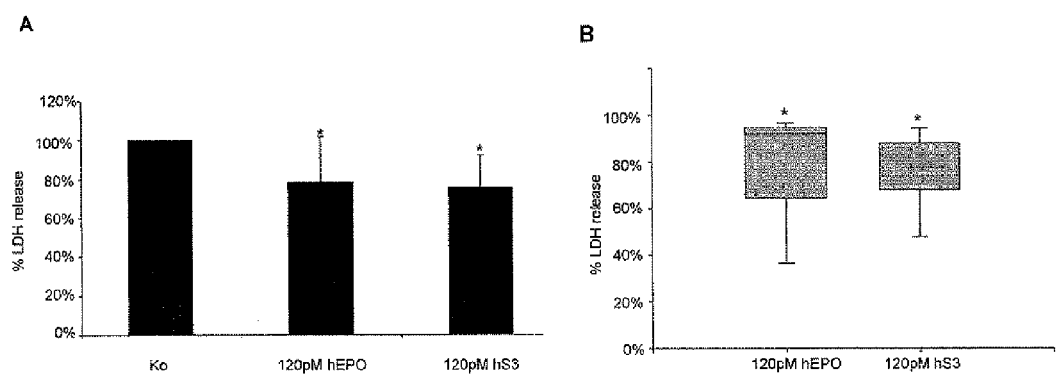

FIG. 11: hEPO- and hS3-mediated cytoprotection in an in vitro model of ischemia consisting of serum deprivation and hypoxia in H9c2 cardiac myoblasts. H9c2 cells were incubated in serum-deprived DMEM medium either under normoxic or hypoxic conditions for 24 h. Cell death was assessed 24 h later by LDH assay. Data were normalized by setting the delta LDH release of untreated cells under normoxic and hypoxic conditions to 100%. A: Column diagram representing the average values of normalized LDH release. hEPO (120 pM) and hS3 (comparable concentration) conferred significant cytoprotection. $P^* < 0.001$ (ANOVA1). B: Data are presented as box plot diagram showing the median (line across the box), the 25th percentile (lower hinge), the 75th percentile (upper hinge), the maximum and the minimum value. Number of experiments n=7.

Figure 12:
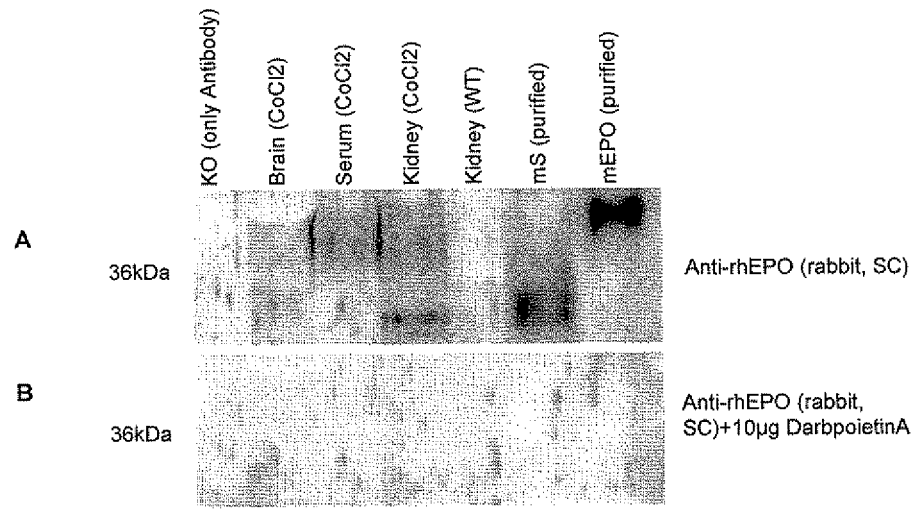

FIG. 12: Immunoprecipitation of vEPO variants using an anti-mEPO antibody from R&D (goat, biotin-labelled); A: Detection of a second EPO isoform (30 kDa) in protein extract from the kidney of cobalt chloride (CoCl2)-treated mice (129S6). B: Competitive blocking of the antibody-antigen interaction by DarbpoietinA.

Figure 13:
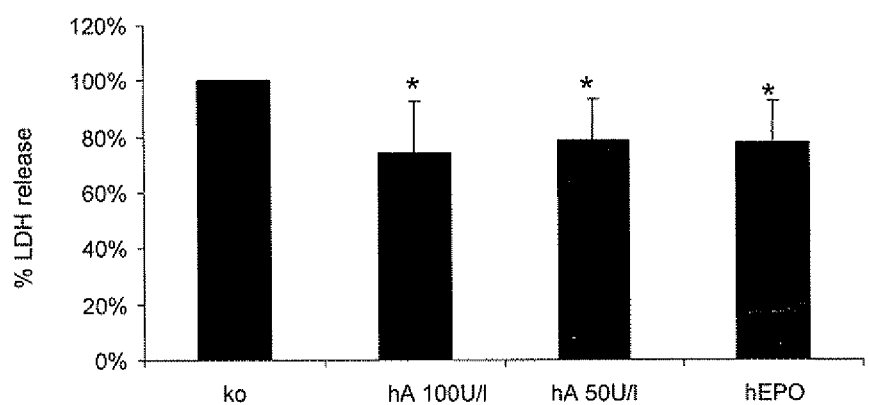

FIG. 13: Neuroprotection mediated by Erythropoietin Alpha-helix (hA; n=4). hA 100/Ul: 30 pM; hA 50 U/l: 15 pM; hEPO: 30 pM=100U/l: $P^* < 0.05$; ANOVA1 versus control.

Figure 14:
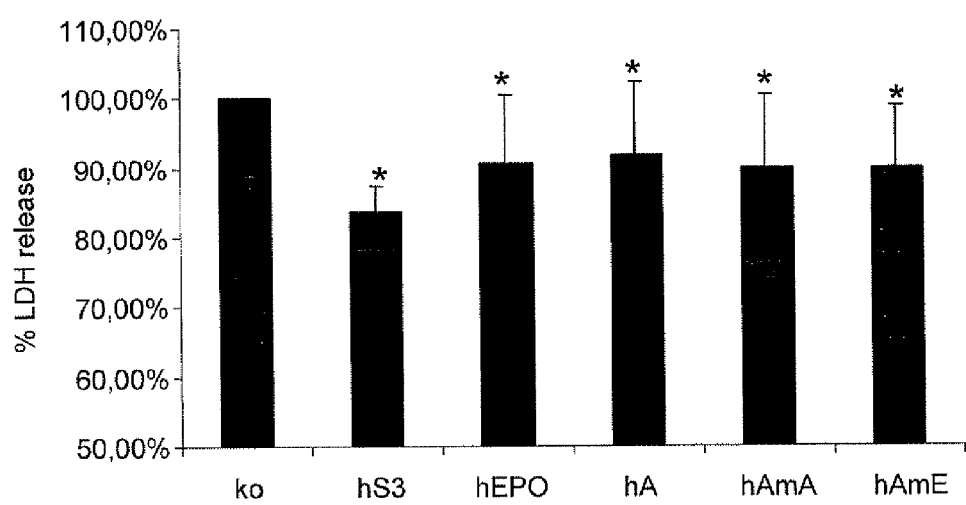

FIG. 14: Neuroprotection mediated by several human EPO-variants (n=6). $P^* < 0.05$, ANOVA1 versus control. hAmE (MutE), hAmA (MutA) and the human alpha helix wild type sequence conferred the same degree of neuroprotection as mature hEPO.

FIG. 15: Neuroprotection mediated by Erythropoietin Alpha-helix deletion variants (n=6). $P^* < 0,05$, ANOVA1 versus control. A: column diagram showing the average values of normalized LDH release. B: Box plot showing the medians and percentiles (25%, 75%) values of normalized LDH release. hA-10 was as potent as hS3 in conferring neuroprotection, whereas hA-20 was devoid of any neuroprotective activity.

Figure 16:
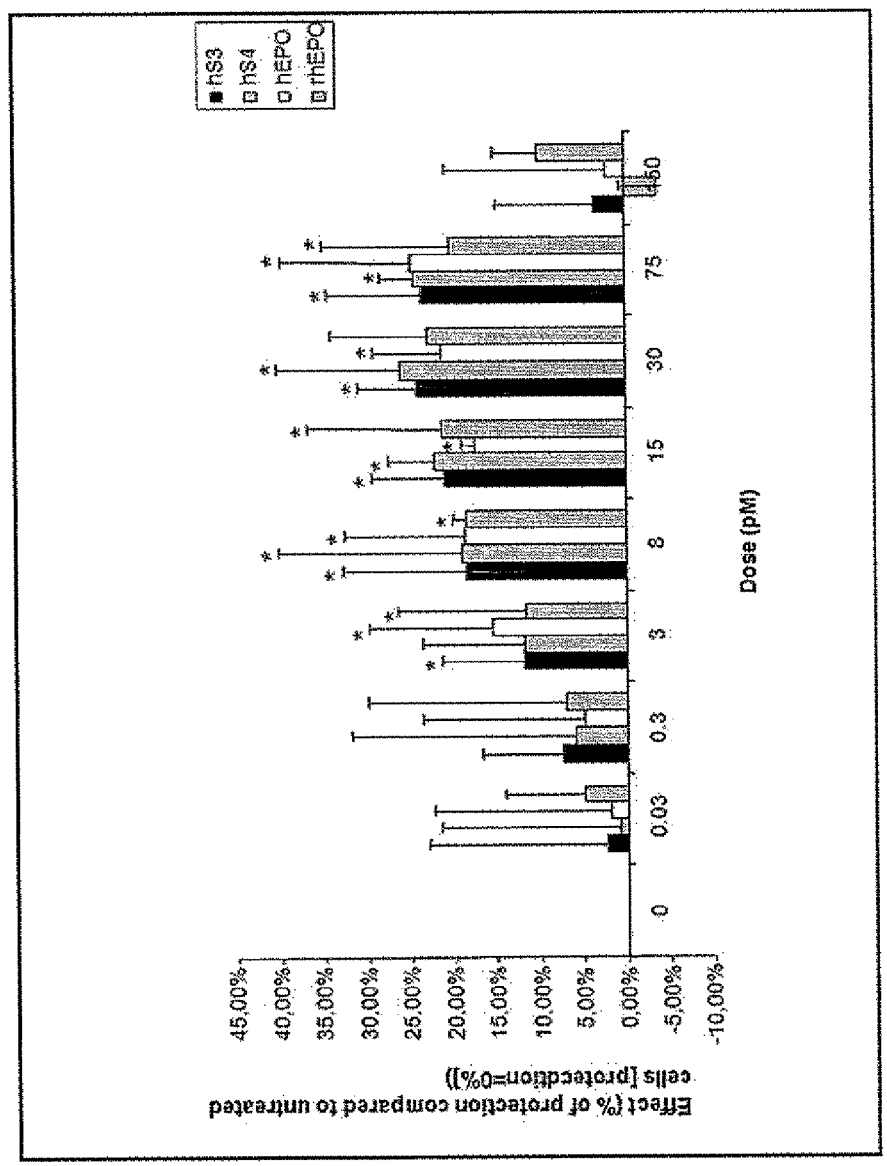

FIG. 16: Dose-response curves of human vEPO variants. Neuronal cultures were pretreated on DIV 8 with concentrations of 0, 0.03, 0.3, 3, 8, 15, 30, 75 and 150 pM vEPOs, whereas 30 pM corresponds to 100 U/l rhEPO from Roche. Neuroprotection is presented as delta LDH release in percent compared to control untreated cultures. Significant neuroprotective effects of more than 10% were achieved for hS3, hS4 and hEPO with concentrations between 3 and 75 pM. Concentrations of 150 pM were toxic in our model of oxygen-glucose deprivation.

FIG. 17: Alignment of nucleic acid sequences of vEPO deletion variants (SEQ ID NOS 79 and 55-59, respectively, in order of appearance).

FIG. 18: DNA sequences of mutants and deletion variants created recombinantly as well as wild type Helix A (hWT-EPO Helix A). Herein SEQ ID NO 55 is hA (Wild type Helix A), SEQ ID NO 56 is hAmA (deletion mutant with Alanin), SEQ ID NO 57 is hAmE (deletion mutant with glutamic acid), SEQ ID NO 58 is hA-10 (deletion mutant Helix A minus 10 aa) and SEQ ID NO 59 is hA-20 (deletion mutant Helix A minus 20 aa).

FIG. 19: A preferred embodiment, wherein the leader (transport or signal) sequences are deleted is depicted. A shows hA DNA (Helix A) without leader (SEQ ID NO. 65), as well as the respective leader DNA-sequence (SEQ ID NO 63). B shows the hA amino acid sequence without the leader (SEQ ID NO. 66). C shows the hA-10 DNA without leader (SEQ ID NO 60). D shows the hA-10 amino acid sequence without the leader sequence (SEQ ID NO 61). E shows the leader amino acid sequence (SEQ ID NO 62) alone.

FIG. 20: Experimental design of the neural stem and progenitor cell (NSC) experiments.

Figure 21:
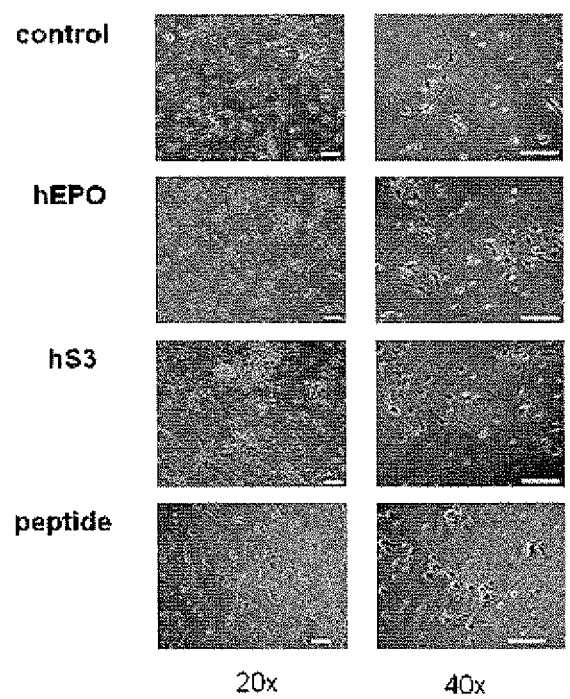

FIG. 21: Survival assay with murine neural stem and progenitor cells: Dissociated murine neural stem and progenitor cells (NSCs) were seeded at high densities in absence of b-FGF and EGF. Addition of 300 pM hEPO (100 ng/ml, 10 U/ml), 300 pM hS3 (100 ng/ml) or 1000 pM peptide hA-10 had a positive effect on the cultures. 24 hours after seeding, cultures differentiated in the presence of vEPOs contained more viable cells and singular cells had longer branches (40× objective).

Figure 22:
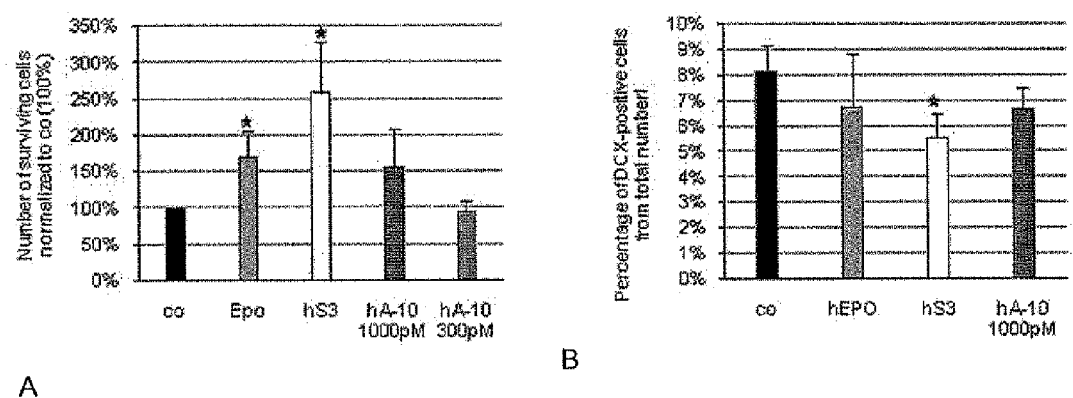

FIG. 22: Survival and differentiation assay of NSCs in the presence of vEPOs and the peptide hA-10: NSCs were differentiated in the absence of b-FGF and EGF, but in the presence of hEPO (300 pM), hS3 (300 pM) or peptide hA-10 (1000 pM). A: NSC cultures were evaluated 24 h after seeding for the numbers of surviving cells (n=6). The number of living cells counted in control cultures was defined as 100% survival. Percentages of surviving cells in treated cultures were calculated accordingly. *p<0.05; multiple comparisons versus control (co) using Dunn's Method.hEPO (300 pM) and hS3 (300 pM) significantly improved cell survival. B: NSC cultures were fixed seven days after seeding and stained for the early neuronal marker DCX. Percentages of DCX-positive cells among all cells were evaluated (n=5). Significantly lower percentage numbers of DCX-positive cells were observed in the hS3-treated cultures. *p<0.01, t-test compared to control (co).

Figure 23:
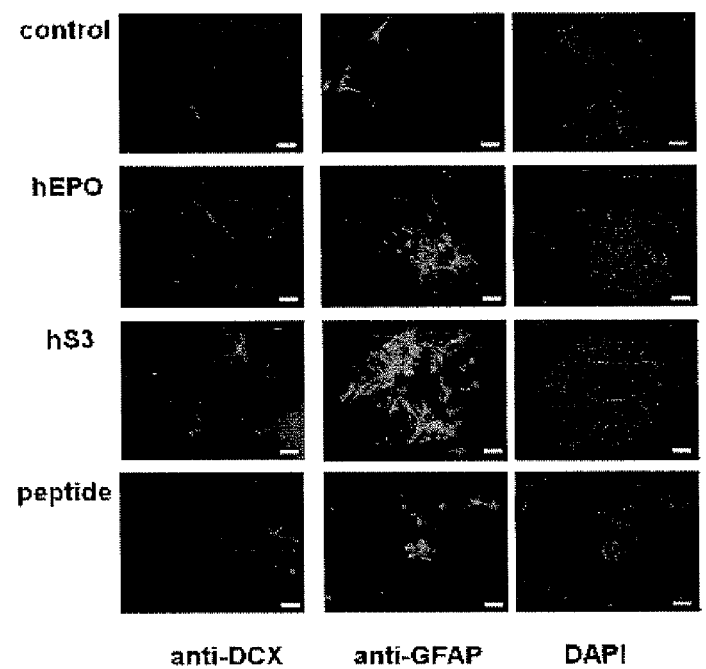

FIG. 23: Staining of NSC cultures differentiated in the presence of vEPOs and the peptide hA-10: NSCs were differentiated in the absence of b-FGF and EGF, but in the presence of hEPO (300 pM), hS3 (300 pM) or the peptide hA-10. At DIV7 after seeding, cultures were fixed and stained for the astroglial marker GFAP, the early neuronal marker DCX and for DAPI, which stains the nuclei of the cells. Addition of rhEPO and hS3 reduced the cell death resulting from growth factor removal. Administration of hS3 and rhEPO was associated with more extensive branching of differentiating neuronal cells and hS3 increased number of glial cells compared with controls. White scale bars in the lower right hand corner indicate the level of magnification (scale bar length=50 μm).

Figure 24:
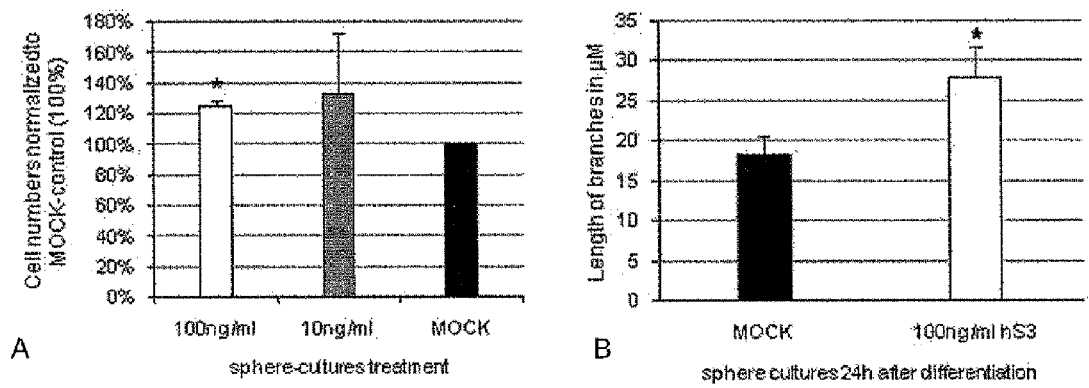

FIG. 24: Sphere cultures maintained in the presence of hS3: Neural stem and progenitor cells were grown as sphere cultures for seven days in medium containing 0, 10 or 100 ng/ml of the human splice variant hS3. A: Spheres were harvested, dissociated and cell numbers of total sphere cultures were evaluated. Four individual experiments were pooled. Absolute cell numbers determined in control cultures (MOCK) were defined as 100%, and cell numbers determined in hS3-treated cultures were calculated accordingly. In cultures grown in the presence of high concentrations of hS3, significantly higher cell numbers were observed. *p<0.05; multiple comparisons, Dunn's method. B: Single cells derived from spheres were differentiated in the absence of growth factors. 24 h after seeding, cultures derived from the spheres and grown in the presence of high concentrations of hS3 contained cells with significantly longer branches (mean of 27.86 μM in comparison to a mean of 18.23 μM in controls). *p<0.05, t-test.

Figure 25:
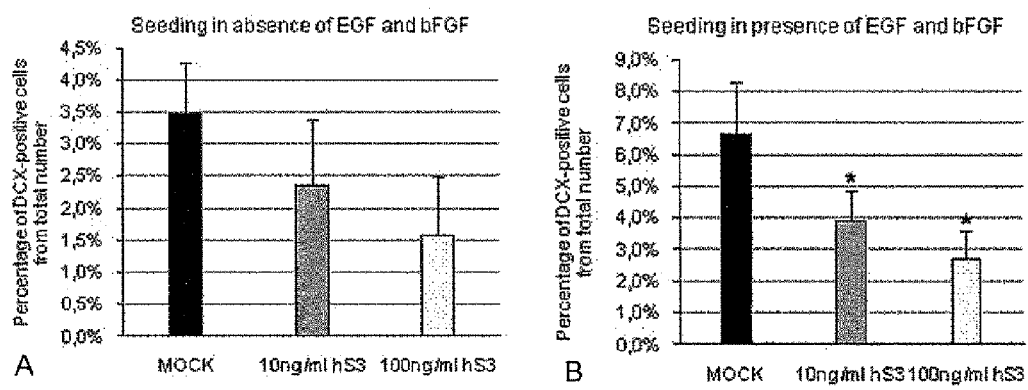

FIG. 25: Effects of hS3 on neuronal differentiation of NSCs. Neural stem and progenitor cells were grown as sphere cultures for seven days in medium containing 0, 10 or 100 ng/ml of the human splice variant hS3. Spheres were dissociated and single cells were differentiated in low concentrations or total absence of b-FGF and EGF. NSC cultures were fixed seven days after seeding and stained for astroglial markers (GFAP) and early neuronal markers (DCX). Percentages of DCX-positive cells among all cells were determined, Significantly lower percentage numbers of DCX-immunoreative cells were observed in the cultures treated with hS3. A: Differentiation of NSCs in medium depleted of growth factors. *p<0.01, t-test compared to control (MOCK). B: Differentiation of NSCs in medium containing small amounts of the growth factors EGF and b-FGF. *p<0.01, t-test compared to control (MOCK).

Figure 26:
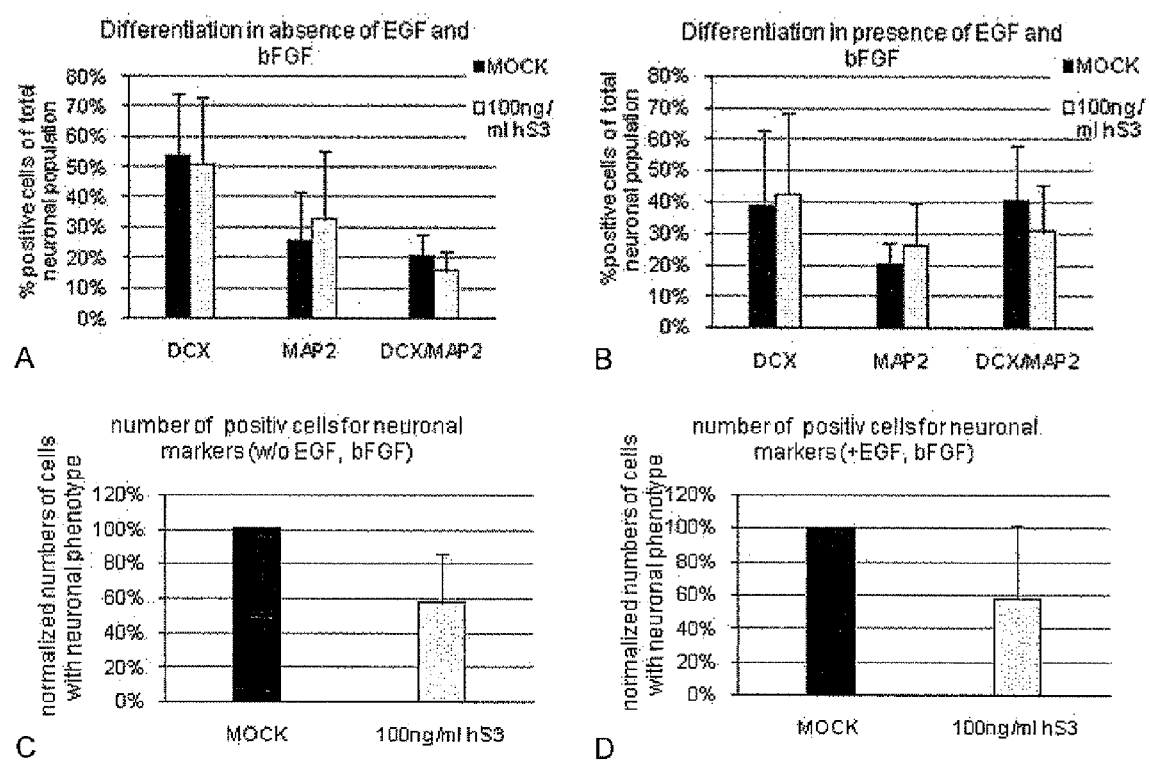

FIG. 26: MAP2 and DCX staining of cultures derived from hS3-treated spheres: Neural stem and progenitor cells were grown as sphere cultures for seven days in medium containing 0 (MOCK) or 100 ng/ml of the human splice variant hS3. Single cells derived from spheres were differentiated in low concentrations or total absence of b-FGF and EGF, and fixed after additional 7 days in culture. Slides were stained for the early neuronal marker DCX and the marker for more mature neurons MAP2. Numbers of DCX-positive (DCX), MAP2-positive (MAP2) and DCX/MAP2 double-positive cells were determined among all immunoreactive cells, i.e. not the entire cell population. A,B: No differences in neuronal maturation based on DCX and MAP2 staining were observed between control cultures (MOCK) and cultures treated with 100 ng/ml hS3. C,D: The overall number of cells differentiated along the neuronal lineage (DCX+MAP2+DCX/MAP2) was lower in cultures treated with 100 ng/ml hS3 compared to controls (MOCK), independent of the presence or absence of growth factors.

Figure 27:
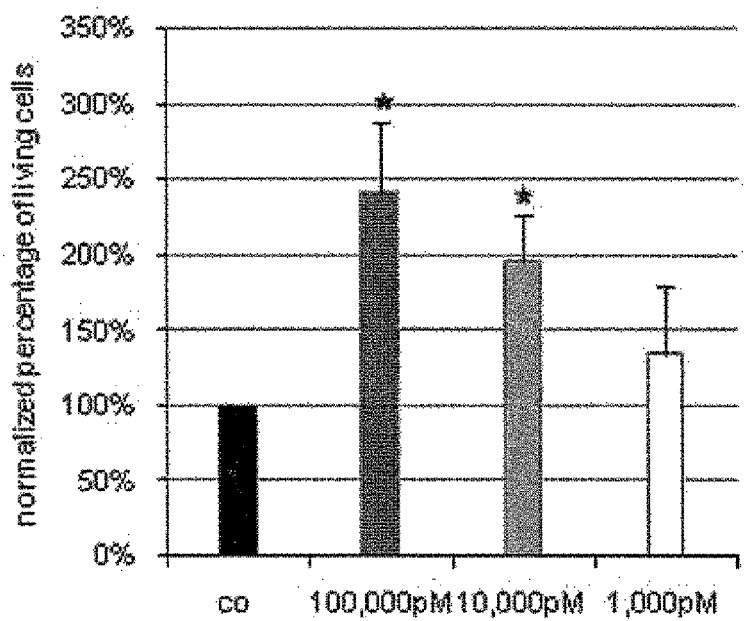

FIG. 27: Survival assay of NSCs in the presence of the peptide hA-10: NSCs were differentiated in the absence of b-FGF and EGF, but in presence of growing concentrations of the peptide hA-10 (1,000-100,000 pM). The numbers of surviving cells were determined in NSC cultures 24 h after seeding. The number of living cells in control cultures (co) was defined as 100% survival. High concentrations of hA-10 ($\geq$10,000 pM) significantly improved cell survival. *p<0.05; multiple comparisons versus control (co) using Dunn's Method.

Figure 28:
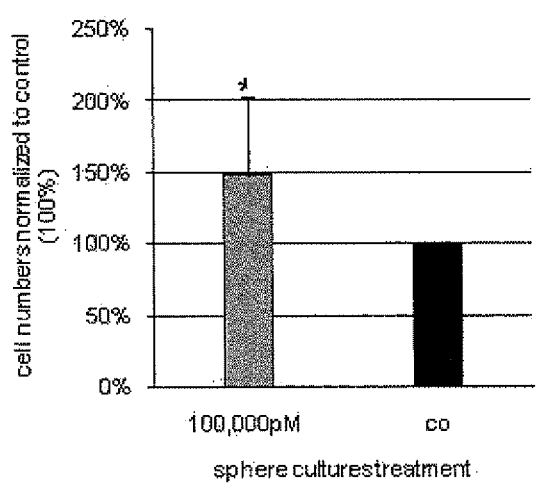

FIG. 28: Sphere cultures maintained in the presence of 100,000 pM peptide hA-10. Neural stem and progenitor cells were grown as sphere cultures for seven days in medium containing 100,000 pM of the alpha helix-derived peptide hA-10. Spheres were harvested, dissociated and the cell numbers determined. Four individual experiments were pooled. Absolute cell numbers in control cultures (co) were defined as 100%, and the cell numbers in cultures treated with hA-10 were calculated accordingly. High concentrations of hA-10 significantly increased cell numbers. *p<0.05; t-test.

Figure 29:
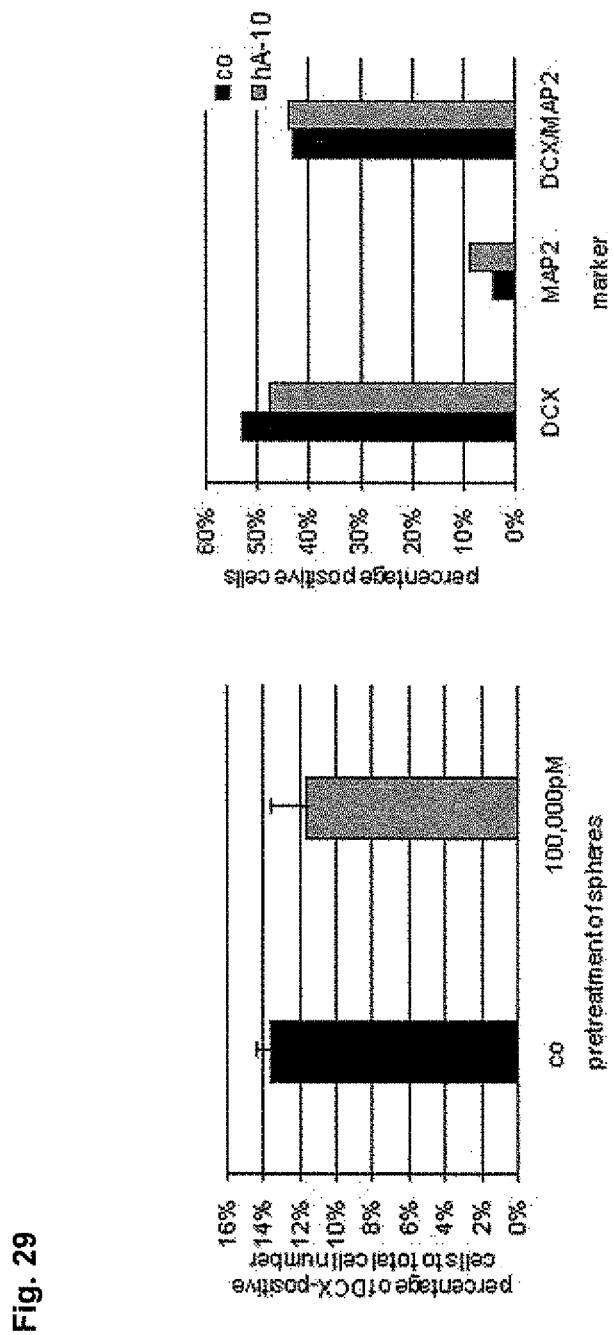

FIG. 29: MAP2 and DCX staining of cultures derived from hA-10-treated spheres: Neural stem and progenitor cells were grown as sphere cultures for seven days in medium containing 0 (co) or 100,000 pM peptide hA-10. Single cells derived from spheres were differentiated in low concentrations or total absence of b-FGF and EGF, and fixed after additional 7 days in culture. Slides were stained for the early neuronal marker DCX and the marker for more mature neurons MAP2. No effects of high concentrations of hA-10 on neuronal differentiation and maturation were observed. A: Percentage of DCX-positive cells among the entire cell population (DAPI positive cells) (n=3). B: Numbers of DCX-positive (DCX), MAP2-positive (MAP2) and DCX/MAP2 double-positive cells among all immunoreactive cells, i.e. not the entire cell population (n=1).

FIG. 30: Experimental design of the hematopoietic stem and progenitor cell (HSC) experiments. Top: Differentiation assay with hematopoietic stem and progenitor cells derived from murine bone marrow. Bottom: Survival paradigm for hematopoietic stem and progenitor cells derived from murine bone marrow.

Figure 31:
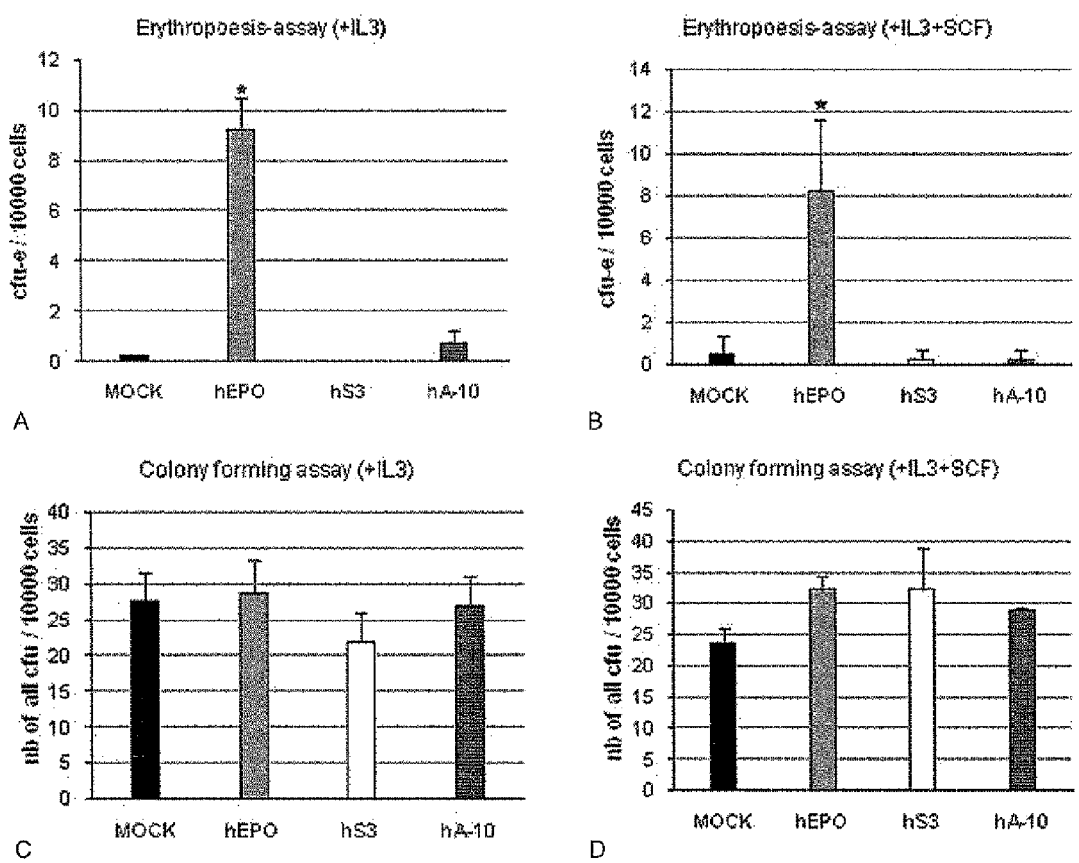

FIG. 31: Effects of vEPO variants on colony formation in clonogenic progenitor assays of murine bone marrow cells. Bone marrow cells were plated at a density of 10,000 cells/ml in serum-free methylcellulose supplemented with either 20 ng/ml IL-3 (A and C), or 20 ng/ml IL-3 and 50 ng/ml SCF (B and D), respectively. EPO and vEPO variants were added at concentrations of 100 ng/ml for hEPO and hS3, or 100 nM for the peptide hA-10. MOCK-medium was added as control (dialysed eluate from protein purifications of supernatants from HEK cells, which were not transfected). Top row: Erythropoiesis assay. Determination of the number of cfu-e after two days in culture revealed that only hEPO, but not hS3 or hA-10, increased erythropoiesis. Statistical significances were tested using ANOVA1. *p<0.05. Bottom row: Colony-forming assay. Determination of the number of all cfu after seven days in culture did not reveal any differences between treatment with hEPO, hS3 or hA-10 and control (MOCK).

Figure 32:
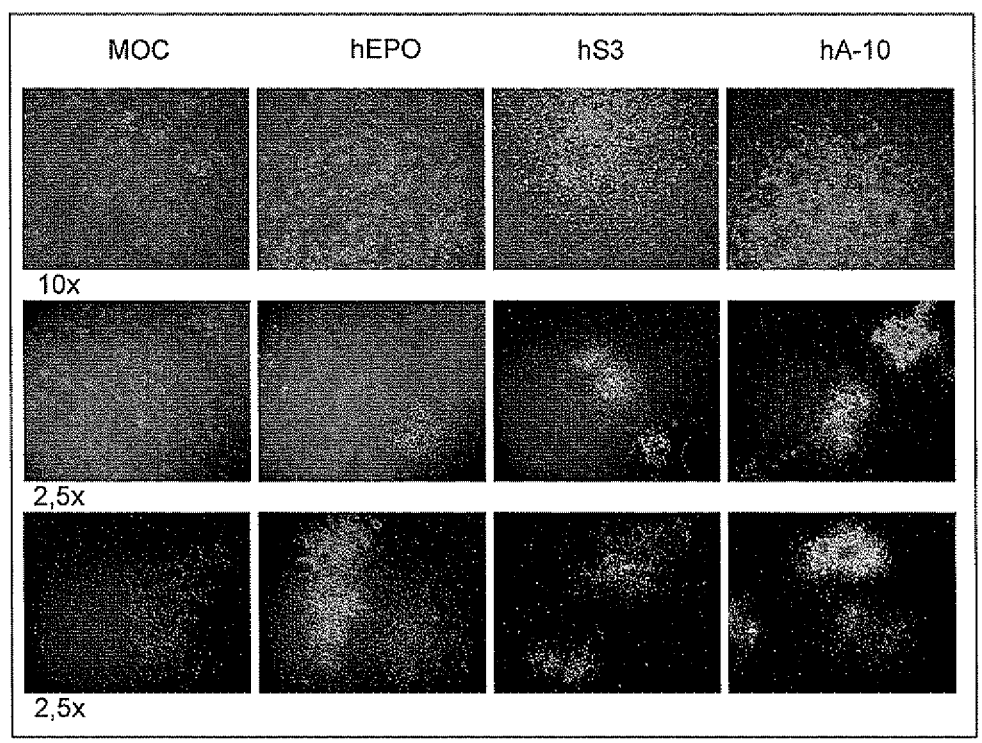

FIG. 32: Survival assay of hematopoietic stem and progenitor cells. Murine bone marrow cells were cultured in the absence of the cytokines IL-3, IL-6 and SCF, but in the presence of 100 ng/ml hEPO, 100 ng/mlhS3 or 100 nM peptide hA-10. After 48 h, non-adherent (floating) cells were harvested and seeded at a low density of 20,000 cells per well in methylcelluose containing IL-3, IL-6 and SCF. Colonies formed after 7DIV were evaluated. Treatment with hEPO, hS3 or hA-10 yielded bigger colonies compared with control (MOCK). At 25× magnification, bigger colonies could be observed in in plates seeded with vEPO-pretreated hematopoietic stem and progenitor cells. All colonies were of the same type, namely cfu-G or cfu-GM as determined by morphological criteria (2.5×=25× magnification; 10×=100× magnification).

Figure 33:
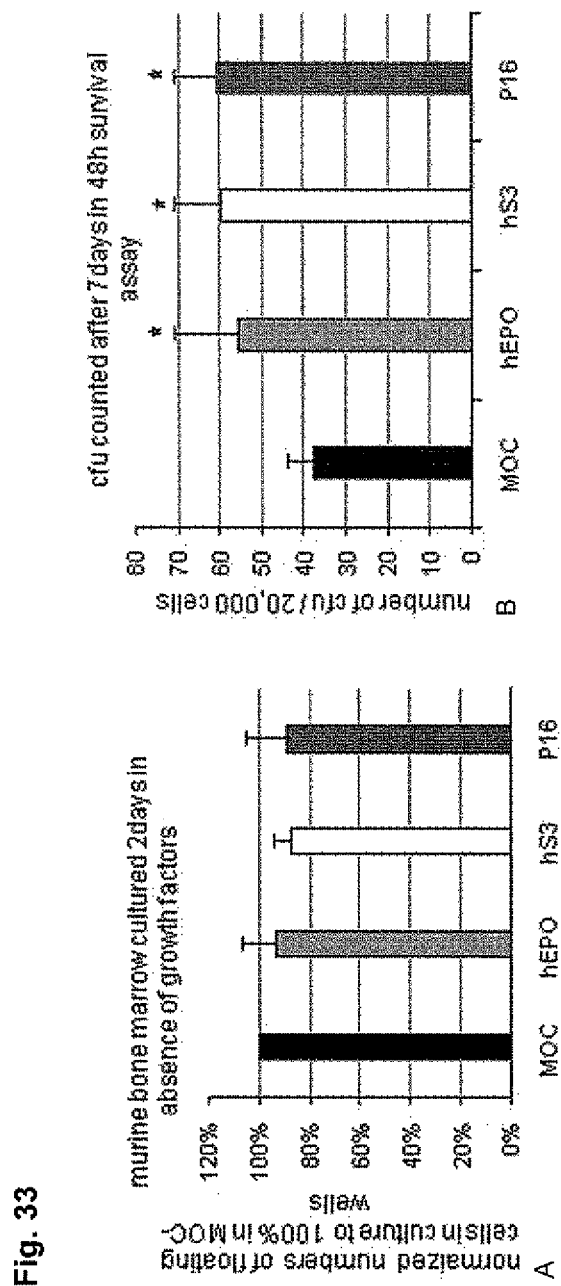

FIG. 33: Survival assay of hematopoietic stem and progenitor cells. Murine bone marrow cells were cultured in the absence of the cytokines IL-3, IL-6 and SCF, but in the presence of 100 ng/ml hEPO, 100 ng/ml hS3 or 100 nM peptide hA-10 at the density of 4×10$^6$ cells per well (4 cm$^2$). A: After 48 h, non-adherent (floating) cells were counted. Absolute cell numbers were normalized to the cell number of MOCK controls (=100%). Neither hEPO, nor hS3 or hA-10 had any effect on the absolute cell number; Student t-test. B: 20,000 non-adherent cells of the above treatment groups were then plated onto methylcelluose supplemented with IL-3, IL-6 and SCF. Colonies formed after 7DIV were counted, and the data from five individual experiments was pooled. The number of cfu was significantly increased in the presence of hEPO, hS3 and hA-10 compared with control, *p<0.05, ANOVA1, Bonferroni t-test.

Figure 34:
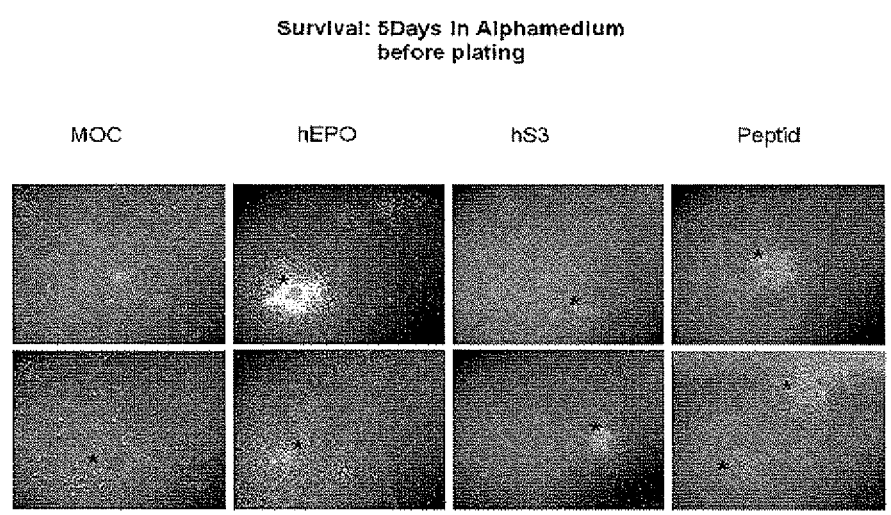

FIG. 34: Survival assay of hematopoietic stem and progenitor cells. Murine bone marrow cells were cultured in the absence of the cytokines IL-3, IL-6 and SCF, but in the presence of 100 ng/ml hEPO, 100 ng/mlhS3 or 100 nM peptide hA-10. After 5 days, non-adherent cells were harvested and plated at a low density of 20,000 cells per well onto methylcelluose containing IL-3, IL-6 and SCF. Colonies formed after 7DIV were evaluated. Treatment with hEPO, hS3 or hA-10 yielded bigger colonies compared with control (MOCK), but no differences in the types of colonies (Treatment with hEPO, hS3 and hA-10=Peptid) resulted in bigger colonies (cfu-G and cfu-GM).

Figure 35:
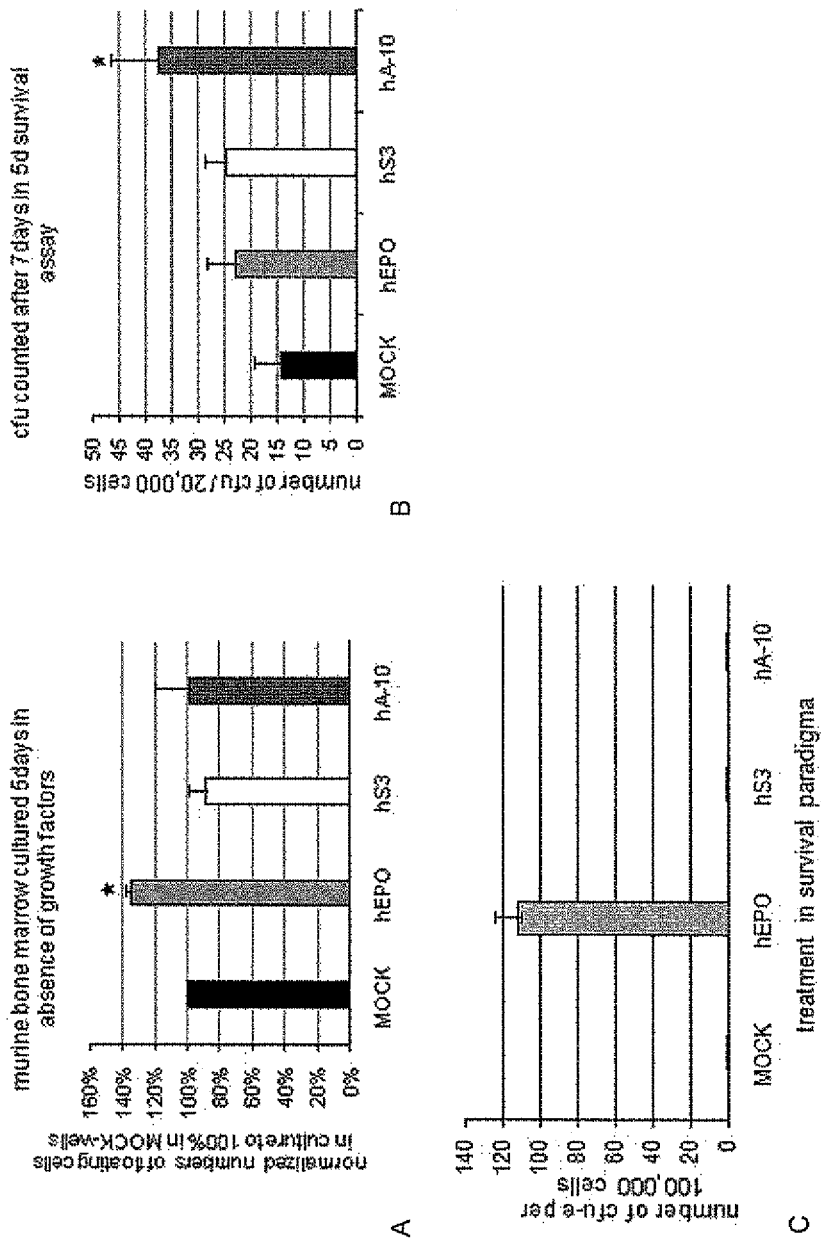
Figure 36:
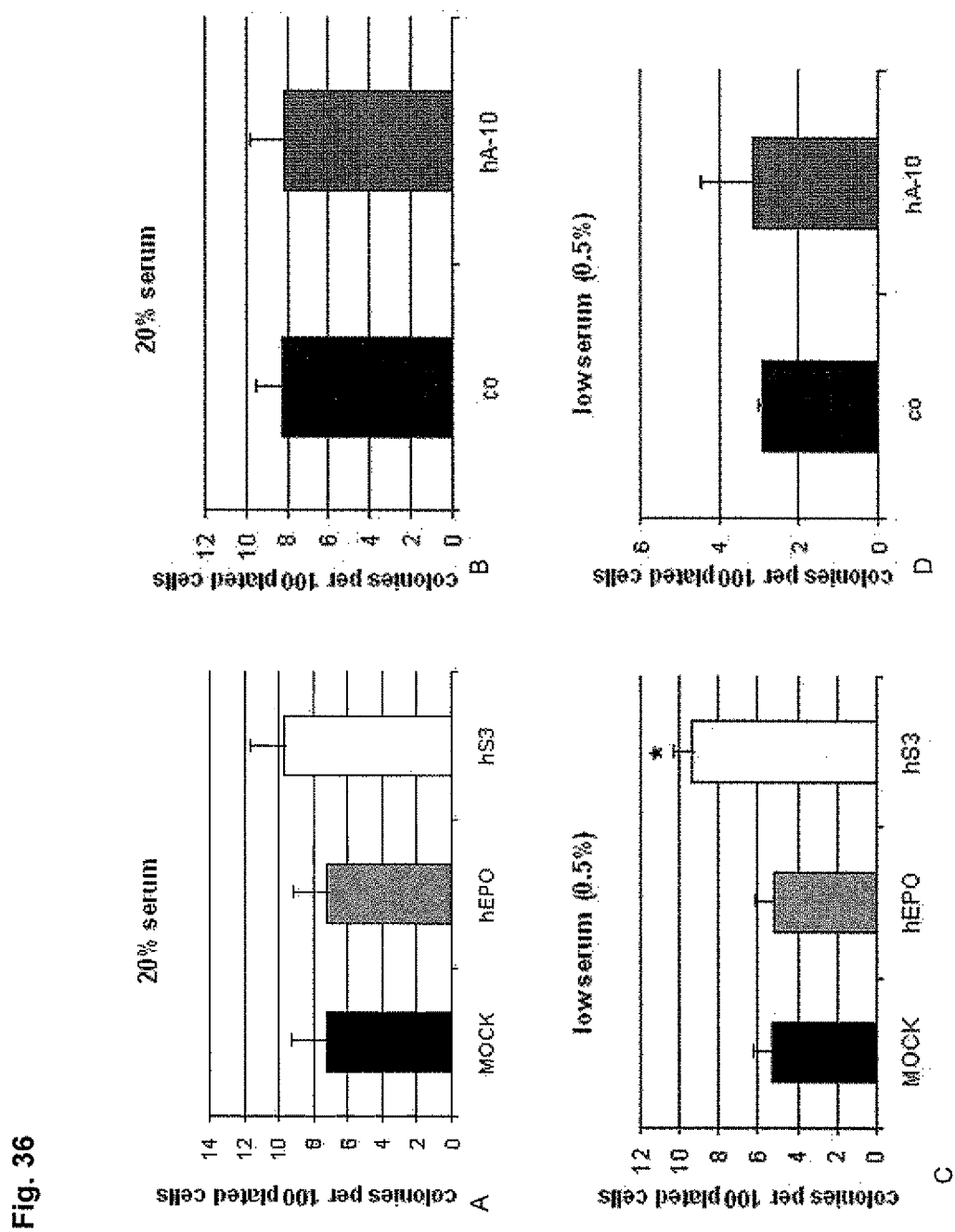

FIG. 35: Survival assay of hematopoietic stem and progenitor cells. Murine bone marrow cells were cultured in the absence of the cytokines IL-3, IL-6 and SCF, but in the presence of 100 ng/ml hEPO, 100 ng/ml hS3 or 100 nM peptide hA-10 at the density of 4×10$^6$ cells per well (4 cm$^2$). A: After 5 days, non-adherent (floating) cells were counted. Absolute cell numbers were normalized to the cell number of MOCK controls (=100%). Only hEPO treatment, but not hS3 or hA-10 increased the absolute cell number. *p<0.001; Student t-test. B: 20,000 non-adherent cells of the above treatment groups were then plated onto methylcelluose supplemented with IL-3, IL-6 and SCF. Colonies formed after 7DIV were counted, and the data from five individual experiments was pooled. The number of cfu was significantly increased in the presence of hA-10, but not by hEPO or hS3 compared with control (MOCK). *p<0.05, ANOVA1, Bonferroni t-test. C: 220,000 non-adhering bone marrow cells were plated onto serum-free methylcellulose containing 200 U/l rhEPO (Roche), 100 ng/ml hS3 or 100 nM peptide hA-10. (n=4). hEPO, but not hS3 or hA-10, increased the number of cfu-e compared to control (MOCK). *p<0.05; t-test. Thus, the hEPO-induced increase in absolute cell numbers observed in (A) results from effects on the erythroid lineage.

FIG. 36: Survival effects of hS3 on murine mesenchymal (stromal) stem and progenitor cells.

MSCs were cultured at a low density in high-serum medium (20% serum) or low-serum medium (0.5% serum). EPO and vEPO variants were added at final concentrations of 100 ng/ml for hEPO and hS3, and 100 nM for the peptide hA-10. After 6 days for high-serum plates or 8 days for low-serum plates, MSC colonies (≥1 mm$^2$ in diameter) were stained with crystal-violett and counted. The number of MSC colonies was unaffected by treatment with hEPO, hS3 or hA-10 (p16) in the high-serum medium condition. However, hS3 significantly increased the number of MSC colonies in the low-serum medium. *p<0.05, ANOVA1, Bonferroni t-test.

Figure 37:
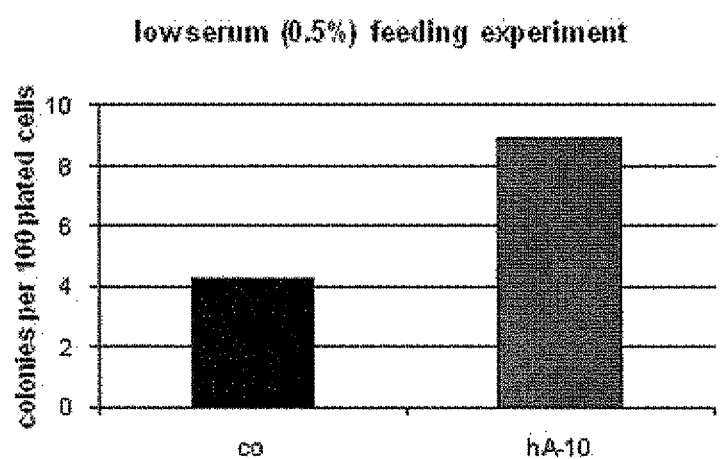

FIG. 37: Survival effects of hA-10 on murine MSCs in a feeding paradigm.

MSCs were seeded at low density in low-serum medium (0.5% serum). Peptide hA-10 was added at final concentrations of 100 nM. After 2 days, medium was replaced with fresh medium containing 0.5% serum and 100 nM peptide hA-10 in the peptide treatment group. Colonies were stained with crystal-violett. Only colonies were counted having a diameter of at least 1 mm$^2$ (n=1).

The peptide hA-10 was found to promote the survival of mMSCs. This effect was not observed in previous experiments without replacement of the medium due to the presumed instability of the peptide.

EXAMPLES

Isolation of Neural Stem and Progenitor Cells

Brains from male C57BL/6 mice aged 2-8months were rinsed twice in PBS before dissection of the subventricular region embodying the lateral ventricles from 2 mm thick acute slices. A thin layer surrounding the ventricles excluding striatum and corpus callosum was prepared, cut into small pieces and incubated for 30-60 min in a papain-DNase (47.2 mg papain, 9 mg cystein, 9 mg EDTA in 50 ml EBSS) solution at 37° C. Cells were pelleted by centrifugation at 110 g for 10 min. Supernatant was removed and tissue was dissociated in an ovomucoid solution (0.7 mg/ml ovomucoid in NBM-A, 1% B27 w/o Retinoic acid, 1% L-Glutamine). Single cells were pelleted by centrifugation at 110 g for 10 min, frozen in aliquots and resuspended in growth medium (NBM-A, 1% B27 w/o Retinoic acid, 1% L-Glutamine, 10 ng/ml EGF, 20 ng/ml bFGF) after thawing. Cells were seeded in 25 cm2 flasks at a density of 4,000 cells per cm2 in order to obtain neurospheres. Experiments were performed with cells from first passage up to passage 10.

Expression and Purification of His-Tagged Erythropoietin and vEPO Variants

His-tagged proteins were transiently expressed in HEK-cells (Freestyle, Invitrogen). Medium from HEK cells was harvested 2-6 days after transfection with pcDNA-3.1-HIS/V5 A—constructs. Cell debris was pelleted at 3500 rpm, 4° C. for 15 min. BD TALON™ Metal Affinity Resin (BD Biosciences) was used for purification of his-tag proteins. All steps (equilibration, washing and elution) were performed at pH 7.1. The provided protocol was modified to a prolonged over-night binding step at 4° C. Eluate was collected in 500 μl-fractions. Fractions were analysed by Western Blots using an anti-rhEPO antibody from Santa-Cruz or a murine EPO ELISA-Kit (R&D). Imidazole was removed from protein-containing fractions using dialysis (Roth) according to the manufactures protocol. This included a change of buffer to PBS supplemented with 0.1% BSA.

Differentiation and Survival Assay (FIG. 20, Experimental Design 1)

Neurosphere cultures were differentiated by removing growth factors from the culture medium and substituting with defined concentrations of vEPOs. Spheres were dissodated into single cells and plated onto poly-L-lysine-coated coverslips at a density of 65,000 or 130,000 cells per well in 24-well plates. After 24 hours, cultures were analyzed for survival rate and morphology of the differentiated cells. After 7 days of differentiation, coverslips were fixed with 4% paraformaldehyde in PBS, blocked with PBS supplemented with 10% normal donkey serum and 0.3% Triton X-100. Incubation with primary antibodies against doublecortin (polyclonal goat antibody, Santa Cruz, dilution: 1:1000) and GFAP (polyclonal rabbit antibody, Daco, dilution: 1:1000) was performed at 4° C. overnight. After washing with PBS and another blocking step with PBS supplemented with 0.1% BSA, secondary antibodies (Alexa594 donkey anti-goat and Alexa488 donkey anti-rabbit, Invitrogen) were added at a dilution of 1:500 for 1 hour. Coverslips were mounted using Vectashield mounting medium supplemented with DAPI (Vector Laboratories) or with Mowiol after an additional DAPI-staining step.

Synthesis of Murine EPO cDNA

RNA was isolated from kidneys of wild type C57BL/6 or SV129S6 mice or from two different mouse brains (1 hour after stroke)by trizol extraction. The RNA was precipitated with chloroform and isopropanol and finally dissolved in DEPC—$H_2O$. DNA was digested to the RQ1 RNase-free DNase protocol from Promega. The reaction was stopped by addition of 200 µl phenol/chloroform/isopropyl alcohol (25/24/1) to the reaction mix and centrifugation for 10 min at 10000 rpm and 10° C. The supernatant was mixed with 200 µl chloroform/isopropyl alcohol (24/1) and centrifuged for 10 min at 10000 rpm and 10° C. 20 µl 8 M lithium chloride and 550 µl absolute ethanol were added to the supernatant. This mix was then incubated for 1 h at −70° C. and subsequently precipitated for 30 min by centrifugation at 11000 rpm and 0° C. The resulting pellet was washed with 600 µl 75% ethanol, centrifuged at 8000 rpm (4° C., 10 min) and dried at room temperature. The RNA was dissolved in 20 µl DEPC—H2O.

Moloney murine leukemia virus reverse transcriptase (MuLV, RNase H minus, purchased from Promega) was employed in first strand cDNA synthesis in a 15 µl reaction volume with DEPC—$H_2O$ comprising 3 µg RNA and 3 µl random hexamer primer (10 µM). Reverse transcription was carried out with 6 µl M-MuLV reaction buffer (5×), 2 µl dNTP (2.5 mM each), 1 µl RNase inhibitor (1 U/µl), 1 µl M-MuLV reverse transcriptase and 5 µl DEPC—$H_2O$ in a PCR machine running the following program: 5 min at 21° C.; 1 h at 37° C.; 5 min at 95° C.

The resulting cDNA pool was used to amplify the complete EPO cDNA by a Nested PCR approach. The first step employed primers lying outside of the coding region of the EPO gene (genepo_sense (SEQ ID NO 39) gaa ctt cca agg atg aag act tgc agc and genepo_antisense; (SEQ ID NO 40): gtg gca gca gca tgt cac ctg tc). The second step used primers designed to amplify the gene from start to stop codon, with attached BamHI cleaving sites for the subsequent cloning (epo_sense (SEQ ID NO 41 tat gga toe atg ggg gtg ccc gaa cgt ccc ac and epo_antisense (SEQ ID NO 42 tat gga tcc tca cct gtc ccc tct cct gca gac). All primers were from MWG-Biotech AG. A nested PCR was performed in a Hybaid PCR machine in two steps, first PCR (3 min at 95° C.; 35 cycles: 30 sec at 65° C., 1 min at 72° C., 30 sec at 95° C.; 10 min at 72° C.; 4° C. hold) and second PCR (3 min at 95° C.; 5 cycles: 30 sec at 67° C., 1 min at 72° C., 30 sec at 95° C.; 15 cycles: 30sec at 70° C., 1 min at 72° C., 30 sec at 95° C.; 10 min at 72° C.; 4° C.).

In both PCRs, Pfu Turbo Hotstart DNA Polymerase (Stratagene) was used according to the manufacturer's protocol. The PCR product of the first step was diluted 1:50 for the second PCR. A second cDNA synthesis protocol was performed using the Access RT-PCR System (Invitrogen) with the following parameters: 48° C. 5 min; 94° C. 2 min; 40 cycles: 94° C. 30 sec, 65° C. 1 min, 70° C. 2 min; 70° C. 7 min; 4° C. The second PCR was performed as described above.

The amplified full-length EPO cDNA and the EPO variants were separated on a 1.2% TAE-agarose gel. A picture of the various PCR products is shown in FIG. 1a. The fragments were than purified using the Wizard SV-Gel Cleanup System (Promega) or the Gel Extraction Kit (Qiagen, Hilden, Germany). As Pfu Polymerase generates blunt end products, the cDNA was subcloned in the pCR-Blunt II-TOPO Vector using chemically competent Top10 One Shot Cells from (both Invitrogen).

Plasmid-DNA was isolated out of single colonies by usage of the Qiagen QIA prep Kit. Inserts were sequenced on an ALFexpress™ DNA Sequencer (Pharmacia Biotech) using the Thermo Sequenase™ Primer Cycle Sequencing Kit (Amersham Biosciences). The primers M13FWDCY (SEQ ID NO 43: gtc gtg act ggg aaa acc ctg gcg) and M13REVCY (SEQ ID NO 44 agc gga taa caa ttt cac aca gga) were labelled with Cy5. The parameters for sequencing were: t=900 min; T=55° C.; 800V; 55 mA and 30 W. The sequence analysis revealed the existence of a novel variant of EPO lacking exon 4 and three internally deleted variants. The nucleotide sequences are depicted in FIG. 2a and FIG. 2b and the encoded peptide sequences are depicted in FIG. 4. The nucleotide and peptide sequence of the EPO variant mS corresponds to SEQ ID NO 13 and SEQ ID NO 14, respectively. The nucleotide and peptide sequence of the EPO variant mG3 corresponds to SEQ ID NO 15 and SEQ ID NO 16, respectively. The nucleotide and peptide sequence of the EPO variant mG5 corresponds to SEQ ID NO 17 and SEQ ID NO 18, respectively. The nucleotide and peptide sequence of the EPO variant m301 corresponds to SEQ ID NO 19 and SEQ ID NO 20, respectively. The nucleotide and peptide sequence of the EPO variant mK3 corresponds to SEQ ID NO 21 and SEQ ID NO 22, respectively.

Synthesis of Human EPO cDNA

Human adult kidney (male) and fetal brain (male) poly A+ RNA was purchased from Stratagene. cDNA was generated from 250 ng kidney RNA or 200 ng brain RNA according to the Moloney murine leukaemia virus reverse transcriptase (MuLV, RNase H minus) as described above. The resulting cDNA pool was used to amplify the complete EPO cDNA using Pfu Polymerase (Stratagene) with the following primers: Hepo_sense (SEQ ID NO 45): gat ggg ggt gca cga atg tcc tgc and Hepo_antisense (SEQ ID NO 46): cac acc tgg tca tct gtc ccc tgt c.

The PCR was performed in a PCR machine from Invitrogen (3 min at 95° C.; 35 cycles: 30 sec at 67° C., 1 min at 72° C., 30 sec at 95° C.; 10 min at 72° C.). In the case of the fetal brain cDNA a Nested PCR approach was used, performing a second amplifying step on the PCR product of 20 cycles. The amplified PCR products were separated on a 1.2% TAE-agarose gel (FIG. 1 b) and purified using the Gel Extraction Kit (Qiagen, Hilden, Germany). The purified cDNA was subcloned in the pCR-Blunt II-TOPO Vector using chemically competent Top10 One Shot Cells (both from Invitrogen). Plasmid-DNA was isolated out of single colonies by usage of the QIA prep Kit (Qiagen, Hilden, Germany). Inserts were sequenced on an ALFexpress™ DNA sequencer (Pharmacia Biotech) using the Thermo Sequenase™ Primer Cycle Sequencing Kit (Amersham Biosciences). The primers M13FWDCY (SEQ ID NO 43) and M13REVCY (SEQ ID NO 44) were labelled with Cy5. The parameters for sequencing were: t=900 min; T=55° C.; 800 V; 55 mA and 30 W. The sequence analysis revealed the existence of two novel variants of human EPO missing exon 3 and the first half of exon 4, respectively, and a number of variants that follows the rule of repeated trimers or hexamers as detected in the mouse. The nucleotide sequences are depicted in FIG. 3a and FIG. 3b and the encoded peptide sequences are depicted in FIG. 4. The nucleotide and peptide sequence of the EPO variant hS3 corresponds to SEQ ID NO 1 and SEQ ID NO 2, respectively. The nucleotide and peptide sequence of the EPO variant h1-4 corresponds to SEQ ID NO 3 and SEQ ID NO 4, respectively. The nucleotide and peptide sequence of the EPO variant h1-5 corresponds to SEQ ID NO 5 and SEQ ID NO 6, respectively. The nucleotide and peptide sequence of the EPO variant hS4 corresponds to SEQ ID NO 7 and SEQ ID NO 8, respectively. The nucleotide and peptide sequence of the EPO variant h1-1 corresponds to SEQ ID NO 9 and SEQ ID NO 10, respectively. The nucleotide and peptide sequence of the EPO variant h2-1 corresponds to SEQ ID NO 11 and SEQ ID NO 12, respectively.

Expression of His-Tagged Proteins in HEK Cells

BamHI and EcoRI restriction sites for cloning were added to both the mouse and the human EPO variants by using overhang sense primers and overhang antisense primers without stop codon (for mouse variants: epo_sense (SEQ ID NO 41) and epoeco_antisense (SEQ ID NO 47): aaa gaa ttc cct gtc ccc tct cct gca gac ctc; for human variants; hepobam_se (SEQ ID NO 48): tat gga tcc atg ggg gtg cac gaa tgt cc, hepoeco_as [SEQ ID NO 49]: aga gaa ttc tct gtc ccc tgt cct gca g). The PCR products were cloned into pcDNA-3.1-HIS/V5 A (Invitrogen) using BamHI and EcoRI restriction sites. Plasmids were amplified in XL-1 Blue Competent Cells (recA1 endA1 gyrA96 thi1 hsdR17 supE44 relA1 lac [F' proAB lacl$^q$ZΔM15 Tn10 (Tet$^R$)]) (Stratagene). The XL-1 Blue Competent Cells transformation protocol was performed without β-mercaptoethanol and with a prolonged heat pulse of 60 seconds. Plasmid DNA was extracted using the QIAprep Spin Miniprep Kit (Qiagen, Hilden, Germany). For transfection into mammalian cells DNA was extracted using the EndoFree Plasmid Maxi Kit (Qiagen, Hilden, Germany). HEK 293 cells (BD biosciences) were grown for 18 days in Dulbecco's modified Eagle's medium (DMEM; Biochrom, Berlin, 1 g/l glucose, 3.7 g/l NaHCO$_3$; supplemented with 10% fetal calf serum GOLD, 1% penicillin/streptavidine and 1% L-glutamine) in tissue culture flasks (25 cm$^2$) at 37° C. and 5% CO$_2$. Cells were split every 2-3 days after reaching 80-90% confluence. At DIV18 120,000 cells were plated per well in a 12 well plate containing Dulbecco's modified Eagle's medium without antibiotics. Cells were grown for approximately 48 h till 50% confluence. Transfection was performed with Lipofectamine 2000 (Invitrogen) adapting the provided protocol for HEK cells.

Plating medium of HEK-cells was replaced 10 min before transfection by serum-free DMEM without antibiotics. Cells were incubated 5 h at 37° C. with DNA-Lipofectamine complexes. Medium was then changed to fresh serum-containing DMEM without antibiotics. At DIV2 cells were split and plated in Dulbecco's modified Eagle's with antibiotics.

Expression and Purification of His-Tagged EPO Variants

His-tagged proteins were transiently expressed in HEK-cells. Medium from HEK293 cells was harvested 2-6 days after transfection with pcDNA-3.1-HIS/V5 A—constructs. Cell debris was pelleted at 3500 rpm, 4° C. for 15 min. BD TALON™ Metal Affinity Resin (BD Biosciences) was used for purification of his-tag proteins. All steps (equilibration, washing and elution) were performed at pH 7.1. The provided protocol was modified to a prolonged over-night binding step at 4° C. Eluate was collected in 500 µl-fractions. Fractions were analysed by Western Blots using an anti-rhEPO antibody from Santa-Cruz or a murine EPO ELISA-Kit (R&D).

Imidazole was removed from protein-containing fractions using HiTrap™ Desalting columns (5 ml) from Amersham Biosciences according to the manufactures protocol. This included a change of buffer to PBS.

Western Blot

A 16% SDS-Gel was prepared using standard-protocols and run at 110 V. Blotting was done on nitrocellulose-membranes for 45 min at 200 mA. The blot was blocked for at least one hour in blocking buffer containing 5% non-fat dry milk powder in 0.1% Tween-20. Incubation with the first antibody (EPO (H-162) sc-7956 rabbit polyclonal IgG, Santa Cruz, 1:500) was performed over-night at 4° C. The secondary antibody (goat anti-rabbit HRP; 1:1000) was added for 2 hours at room-temperature. The blot was revealed by use of Luminol; photos were exposed for 2 minutes. Membranes were stained with Ponceau Red. The EPO specific antibody was capable of detection all EPO variants.

Erythroid Colony Formation Assay

Bone marrow cells were harvested from tibia and femur of male C57BL16 mice (8-11 weeks) and resuspended in α-medium (supplemented with 10% fetal calf serum GOLD, 1% penicillium/streptavidine and 1% L-glutamine). Cells were seeded in 35 mm$^2$ Petri dishes (225.000 cells/dish) containing 8 parts Metho Cult SF 3236 methyl cellulose (StemCell Technologie Inc), 1 part cells and 2 parts a-medium mixed with HEK-cell preconditioned medium containing the EPO derivates (150 U/l in the case of murine EPO). 150 U/l of rhEPO (Roche) was used as positive control. Plates were incubated at 37° C. in a humidified atmosphere containing 5% CO$_2$ for 48 hours. For evaluation only reddish colonies containing at least 6 hemoglobinised cells were taken into account.

Hematopoletic Potential of the EPO Variants

Metho Cult SF 3236 triggers the formation of colonies (CFU-M, CFU-G or CFU-E) only after addition of the appropriate cytokines. Formation of CFU-E (Colony forming unit-erythroblast) can be observed, after addition of erythropoietin, after 2 days. The small irregular reddish colonies disappear by day 3.

In this assay, the hematopoietic potential of the variants was tested and compared to wild type form of EPO as well as rhEPO. The following conditions were prepared for comparison: medium from HEK cells transfected with pZ/EG as negative control, medium from HEK cells transfected with pZ/EG cells plus 150U/l rhEPO (Roche) as a positive control, and medium from HEK cells transfected with either pZ/EG-EPO-IRES (150 U/l murine EPO), pZ/EG-Splice-IRES (variant S; mS) or pZ/EG-G3-IRES (variant G3; mG3). At DIV2 only reddish colonies were counted containing at least 6 hemoglobinised cells. The results of three independent experiments are depicted in FIG. 5.

In comparison to murine EPO and rhEPO, the murine EPO variants (mS and mG3-variant) lacked hematopoietic potential.

Primary Neuronal Cultures

Rat primary neuronal cultures were obtained from E16 to early E19 embryos of Wistar rats (Bundesinstitut für gesundheitlichen Verbraucherschutz and Veterinärmedizin, Berlin, Germany). Cre-expressing mouse neurons were obtained from E16 embryos of heterozygous transgenic mice expressing Cre-recombinase under the control of the tubulin α-1 promoter (provided by Dr. U. Schweitzer; Experimental Endocrinology, Charité). Murine and rat cultures were prepared according to a modified protocol from Brewer (1995) *J Neurosci Res*. 42: 674-83. Cerebral cortex was isolated after removal of meninges and rinsed twice in PBS (Biochrom, Berlin, Germany). After 15 min incubation in trypsin/EDTA (0.05/0.02% w/v in PBS) at 37° C., tissues were rinsed twice in N-Med (modified Eagle's medium from Gibco with 10% fetal calf serum, 100 U penicillin plus streptomycin from Biochrom, 2 mM L-glutamine, 100 IE insulin/l, 10 mM HEPES and 44 mM glucose) and dissociated carefully in a small volume of N-Med using a Pasteur pipette. Cells were pelleted at room temperature by 2 min centrifugation at 210 g and resuspended in NBM starter medium (Neurobasal medium from Gibco with 2% B27 supplement from Gibco, 1% Pen/Strep, 0.5 mM L-glutamine and 25 µM glutamate).

Preparation of Culture Plates 24-well plates and 6-well plates were pretreated by overnight incubation at 4° C. with poly-L-lysin from Biochrom (2.5 µg/ml in PBS). Rinsing of the wells with PBS was followed by 1 h incubation at 37° C. with coating medium (modified Eagle's medium with 5% FCS Gold from PAA, 1% Pen/Strep, 10 mM HEPES and 0.03 w/v collagen G from Biochrom), then the wells were carefully rinced twice with PBS. Volume and type of plating medium was chosen depending on experimental procedure.

Oxygen Glucose Deprivation in Rat Primary Cortical Neurons—a Cell Culture Model of Cerebral Ischemia For OGD, the culture medium was washed out by rinsing once with PBS. OGD was induced with 500 µl of a deoxygenated aglycemic solution ($BSS_0$—$O_2$; 143.8 mM $Na^+$, 5.5 mM $K^+$, 1.8 mM $Ca^{2+}$, 0.8 mM $Mg^{2+}$, 125.3 mM $Cl^-$, 26.2 mM $HCO_3^-$ and 0.8 mM $SO_4^{2-}$, pH 7.4) in a hypoxic atmosphere generated by a dedicated, humidified gas-tight incubator (Concept 400, Ruskinn Technologies, Bridgend, UK) flushed with a gas mix containing 5% $CO_2$, 85% $N_2$ and 10% $H_2$. OGD-time depended on the density and the age of the culture and varied between 2 h 30 min and 2 h 40 min. In control experiments the wells were treated with 500 µl of the oxygenated glycemic $BSS_0$ solution ($BSS_0+O_2$; 143.8 mM $Na^+$, 5.5 mM $K^+$, 1.8 mM $Ca^{2+}$, 0.8 mM $Mg^{2+}$, 125.3 mM $Cl^-$, 26.2 mM $HCO_3^-$, 0.8 mM $SO_4^{2-}$, and 20 mM glucose, pH 7.4) and incubated at 37° C. in a normoxic atmosphere containing 5% $CO_2$. Immediately after OGD, treated cells and controls were changed from BSS solution to 500 µl of medium containing 40% conditioned NBM plus 60% fresh NBM. After 24 h, lactate dehydrogenase (LDH) activity was measured in the supernatants as an indicator of cell death.

For LDH measurement 25 µl of medium was mixed with 100 µl fresh β-NADH solution (0.15 mg/ml in 1×LDH-buffer; Sigma, reduced form) in a 96 wells plate (Greiner). 25 µl of 22.7 mM pyruvate (Sigma) was added immediately before placing the plate into the Reader (Thermo Labsystems; MRX$^{TC}$ Revelation). Parameters were chosen as follows: filter: 340 nm, shake time: 5 sec, interval: 30 sec, counts: 10. LDH-concentration was calculated proportionally to the LDH-standard (Greiner, system calibrator).

Induction of Neuroprotection by Conditioned Medium from Transfected HEK293 Cells Expressing EPO Variants In the following experiments rhEPO (recombinant human EPO from Sigma Aldrich, Deisenhofen, Germany) was used as a positive control. Neuroprotection assays are schematically depicted in FIG. 6. Neurons were plated in 24-well plates at a density of 300,000 cells in a final volume of 600 µl NBM starter medium. After 4 days, 200 µl of the medium was replaced by 250 µl fresh NBM (same as NBM starter without glutamate).

For pretreatment with rhEPO, wild type mEPO, wild type hEPO or EPO variants the medium was removed to an end volume of 200 µl and filled up with 200 µl fresh NBM+B27 containing equimolar amounts (corresponding to 200 U/l rhEpo) of EPO or EPO variants, respectively. Equivalent concentrations of the various EPO variants (as well as mEPO and hEPO) in the conditioned medium from HEK293 cells were estimated by Western blot and EPO-Elisa. Thereafter neurons were grown for 48 h under normoxic, humified conditions at 37° C. before oxygen glucose deprivation (OGD) was performed (OGD interval as indicated). Cell death was assessed 24 h after OGD by measurement of LDH release. Reduction in LDH release, compared to mock-treated neurons (medium from HEK293 cells transfected with the backbone plasmid; =ko; 100%), is a quantitative measure of neuroprotection. In all experiments we observed a more robust neuroprotective effect provided by the EPO variants, if compared to wt EPO (see FIG. 7 Panel A and B for murine EPO and variants thereof and FIG. 8 Panel A and B for human EPO and variants thereof).

The neuroprotection induced by the murine EPO variants is more robust than that induced by EPO (rhEPO as well as wild type mouse EPO). For example, neuroprotection mediated by EPO can only be observed in a clearly defined window of OGD length (corresponding to a clearly defined damage level). At low concentration the neuroprotection by hS3 and hS4 was equal or better than the neuroprotection of wt hEPO. Overall, neuroprotection induced by the variants is stronger than that induced by rhEPO. In addition, variants have an higher neuroprotective potential than both wild type forms mEPO and hEPO, which were produced by the same procedure as the EPO variants.

H9c2—Model of Ischemia

The rat BDIX heart myoblast cell line (obtained from European Collection of Cell Cultures) was cultured in DMEM (Biochrom) containing 4.5 g/l glucose supplemented with 2 mM L-glutamine, 10% inactivated fetal calf serum and 1% penicillin-streptavidin. Subconfluent cultures (70%) were subcultured 1:4. Cells were plated in 400 µl medium containing 120 pM hEPO or hS3 respectively in a density of 15,000 cells per well in 24-well plates and cultured for 48 hours. Hypoxia was achieved by culturing the cells in 400 µl serum-deficient DMEM containing 4.5 g/l glucose supplemented with 2 mM L-glutamine and 1% penicillin-streptavidin and leaving them for 24 h in an anaerobic workstation (Concept 400, Ruskinn Technologies, Bridgend, UK) saturated with a gas mix containing 5% $CO_2$, 85% $N_2$ and 10% $H_2$ at 37° C. Control cells were left in serum-deficient DMEM in a normoxic incubator. At the end of the experiment medium was replaced to 400 µl fresh serum-deficient DMEM and LDH was measured according to standard protocols 24 h later.

Immunoprecipitation

Male 129S6 mice or male C57B16 mice (8-10 weeks, Bundesinstituts für Risikobewertung, Berlin) having free access to food and water were used for the experiments. CoCl2 was injected subcutaneously in a dose of 60 mg/kg and animals were killed 18 hours later. Protein expression was measured in serum, kidney and brain protein extracts by a commercial available ELISA (R&D, mEPO).

Antibodies for immunoprecipitation were purchased from R&D (anti-mEPO antibody, goat, biotin-labelled) and Santa-Cruz (anti-rhEPO, rabbit). Immunoprecipitation was perfomed according to standard protocols and evaluated by western blot.

Blocking of the western blot detection antibody was achieved by two hours incubation with 10 µg DarbpoietinA at room temperature prior to blot incubation.

Generation of Alpha-Helix-Mutants (FIG. 10)

Human alpha-helix-mutants were all generated by PCR based approaches using standard protocols.

Mutant A (hAmA) and mutant E (hAmE) are variants of the alpha-helix with amino acid exchange at position 41 (arginine). cDNA sequence was changed from AGG to GCG for mutant A (alanine) or to GAG for mutant E (glutamate). -20aa and -10aa are deletion variants of the alpha-helix missing 20 amino acids or 10 amino acids respectively at the c-terminus. All mutants were generated without V5 and His-tag and expressed in HEK 293 cells. Neuroprotection experiments were performed as described previously using medium of transfected HEK cells expressing the different variants.

hEPO and hS3 Mediated Cytoprotection in a Model of Ischemia in H9c2 Cells (FIG. 11)

The cytoprotective potential of the EPO variants was shown exemplarily for purified hEPO and hS3 in a model of ischemia consisting of serum deprivation and hypoxia in H9c2 cardiac myoblasts (FIG. 11). LDH release was assessed as a marker of apoptotic cell death. We found significant cytoprotective capacities for both variants (approximately 20% and 25% for hEPO and hS3).

Immunoprecipitation Reveals EPO Splicing Variant in Kidney Protein Extracts of CoCl2-Treated Mice (FIG. 12)

To strengthen our finding of EPO splicing variants in human and murine tissues by a PCR-based approach we performed immunoprecipitations on murine serum, brain and kidney protein extracts of CoCl2 treated mice using antibodies tested to recognize both variants. Subcutaneous injection of CoCl2 is known to increase erythropoietin levels in several mouse tissues, namely blood, brain, liver and kidney.

We were able to precipitate erythropoietin (approximately 40 kDa) from serum, brain and kidney protein extracts of CoCl2 treated mice (FIG. 12); precipitation of erythropoietin from a kidney protein extract of an untreated mouse failed due to the low expression level. Furthermore we were able to prove the existence of a second smaller protein (approximately 30 kDa) in the kidney protein extract of CoCl2 treated mice. This protein is specifically recognized by the anti-rhEPO antibody as shown by complete blocking of the antibody-antigene interaction with Darbpoietin A. These findings strongly support the existence of a murine erythropoietin splicing isoform. These results were reproduced in a second mouse strain, namely C57Bl6.

Neuroprotection Mediated by Different Variants of the Erythropoietin Alpha-Helix (FIGS. 13-16)

Analysing the neuroprotective potentials of the so far identified erythropoietin variants we suggested the alpha helix to be the functionally important domain for the neuroprotective character of erythropoietin. In order to test this hypothesis we expressed a shortened form of human erythropoietin, namely the alpha-helix domain, in HEK 293 cells and tested this peptide in our OGD-model. We found an equivalent protective potential with 30 pM and 15 pM of this peptide to 30 pM of hEPO as shown in FIG. 13.

In order to identify the functional important residues in the alpha helix domains of human erythropoietin we generated different erythropoietin mutants containing either amino acid exchanges (hAmA and hAmE) or complete domain deletions (hA-10 and hA-20).

Neither the neutral nor the acidic amino acid exchange at position 41 was able to destroy the neuroprotective potential of the alpha-helix in our OGD model (FIG. 14).

Neuroprotection mediated by several human EPO-isoforms (n=6) P*<0,05; ANOVA1 versus control (FIG. 1)

Deletion variants missing 10 or 20 amino acids at the c-terminus of the alpha-helix were expressed in HEK293 cells and also tested in the OGD-model. The deletion variant hA-10 had still neuroprotective properties comparable to the hS3 splice isoform. Deletion of 20 amino acids (hA-20) led to a peptide that was not protective anymore (FIG. 15).

Dose-response curves of neuroprotection by human vEPO variants. Neuronal cultures were pretreated on DIV 8 with concentrations of 0, 0.03, 0.3, 3, 8, 15, 30, 75 and 150 pM vEPOs, whereas 30 pM corresponds to 100U/l rhEPO from Roche. Significant neuroprotective effects of more than 10% were achieved for hS3, hS4 and hEPO with concentrations between 3 and 75 pM. Concentrations of 150 pM were not neuroprotective in our model of oxygen-glucose deprivation (FIG. 16).

vEPO Treatment of Neurosphere Cultures (FIG. 20, Experimental Design 2)

Cells were seeded in 25 cm flasks at a density of 4,000 cells per cm2 in presence of 4 ml vEPO containing medium. 48 h after seeding cultures were fed with 2 ml vEPO containing medium and grown for 5 more days. At the day of experiment spheres were harvested at 110 g for 10 min, washed once in growth-factor-free NSC-medium and dissociated to single cell suspensions.

For differentiation, cells were plated onto poly-L-lysine-coated coverslips in 24-well plates at a density of 65,000 cells per well in medium containing low concentrations of b-FGF and EGF (8.6% of growth medium) or at a density of 100,000 cells per well in growth-factor-free NSC-medium. After 24 hours, cultures were analyzed for morphology of the differentiated cells. Two days after seeding NSCs were fed with 200 µl growth-factor-free NSC-medium per well. After 7 days of differentiation, coverslips were fixed with 4% paraformaldehyde in PBS and stained as described previously for doublecortin (polyclonal goat antibody, Santa Cruz, dilution: 1:1000), GFAP (polyclonal rabbit antibody, Daco, dilution: 1:1000) and MAP2 (mouse antibody clone HM-2, Sigma-Aldrich, dilution: 1:1000). Primary antibodies were detected with secondary antibodies Alexa594 donkey anti-goat, Alexa488 donkey anti-rabbit and Alexa488 donkey anti-mouse from Invitrogen at a dilution of 1:1000.

vEPO Variants Enhance Survival of NSCs During Differentiation

In a first approach (Experimental Design 1) cells were grown as sphere cultures in medium containing the growth factors EGF (epidermal growth factor) and b-FGF (fibroblast growth factor). On the day of the experiment cells were washed with growth-factor free medium and seeded as single cell suspension at high density on PLL coated coverslips either in presence or absence of 300 pM hEPO (100 ng/ml, 10 U/ml), 300 pM hS3 (100 ng/ml) or 1000 pM peptide hA-10. Controls were seeded in equal volumes MOCK-medium (dialysed eluate from protein purifications of supernatants of non-transfected HEK cells).

24 h hours after seeding we observed healthier cultures in presence of vEPOs. Cultures contained more living cells than control cultures and the surviving cells seemed to be better developed having longer branches (FIG. 21). This effect seemed to be most pronounced in hS3 treated cultures. In order to quantify this observation, surviving cells on three randomly chosen surface areas at 200× magnification were counted. The numbers of surviving cells in control cultures were set to 100% and the numbers of cells in treated cultures were calculated accordingly. In six independent experiments we observed 1.7 to 2.6 higher surviving rates in presence of hEPO and hS3 24 hours after seeding. Small effects were also detected for higher concentrations of the hA-10 peptide (p=0.002 in Mann-Whitney rank sum test compared to co) (FIG. 22A).

After 7 days, cultures were fixed with 4% paraformaldehyde and double-stained for the early neuronal marker doublecortin (DCX) and the glial marker GFAP. Double-cortin positive cells and total cell numbers were determined on minimum four randomly chosen surface areas at 200× magnification. We found a trend for diminished proportions of doublecortin-positive cells on total cell numbers in presence of hS3 compared to control and the other vEPOs hEPO and hA-10. In control-, hA-10- and hEPO cultures, 7 to 8% of the cells were found to express DCX whereas after hS3 treatment only 5.5% of the cells were positive for this early neuronal marker (FIG. 22B).

Staining of the different treatment groups showed also more cells in DAPI stainings and higher numbers of GFAP positive cells in hS3-treated cultures analogue to the finding of higher surviving rates 24 h after seeding (FIG. 23).

hS3 Pre-Treatment of NSCs has Positive Effects on Survival During Differentiation In a second experimental approach (Experimental Design 2) neural stem cells were grown to spheres in presence of hS3, b-FGF and EGF or in presence of b-FGF and EGF alone (control). After 7 days in culture spheres were dissociated to single cells and numbers of living cells were evaluated. Cultures grown in presence of 100 ng/ml hS3 showed 20% higher cell numbers than MOCK cultures (FIG. 24A).

For differentiation experiments spheres were washed with growth-factor free medium and seeded as single cell suspensions on PLL coated coverslips either in presence of small amounts of the growth factors EGF and b-FGF (65,000 cells per well) or in complete absence of growth factors (130,000 cells per well). In the highly damaging approach of seeding cells in complete absence of growth factors we observed a faster outgrowth of the differentiating cells derived from spheres cultivated in presence of hS3. Cells of hS3-treated spheres had in average 1.5 times longer branches than cells from untreated spheres (FIG. 24B).

Differentiated cultures derived from pre-treated sphere cultures were fixed with 4% paraformaldehyde at DIV7 and stained for the early neuronal marker doublecortin (DCX) and the glial marker GFAP. Doublecortin positive cells were determined proportionally to total cell numbers (DCX and GFAP positive cells). Cultures derived from untreated spheres contained on a percentage basis more DCX-positive cells than cells derived from hS3-treated spheres (FIG. 25). In both differentiation conditions low concentration or complete absence of EGF and bFGF pretreatment with 10 ng/ml hS3 led to a reduction of 30% DCX-positive cells compared to control and after pretreatment with 100 ng/ml hS3 even to a reduction of 60% compared to control.

Double staining for the early neuronal marker doublecortin (DCX) and the more mature neuronal marker MAP2 showed that cells derived from hS3-treated spheres tended to develop faster in more mature cells but not to statistically significances (FIGS. 26A+B). More MAP2 stained cells were detected in the neuronal cell population (population of DCX, MAP2 or DCX/MAP2-stained cells) after hS3 treatment than in control cultures. But slides from MOCK-treated cultures contained overall more cells of neuronal phenotypes (DCX, MAP2 or DCX/MAP2-stained cells) than hS3-treated cultures (C+D). These results suggest that hS3 is a differentiation factor for the astroglial lineage, but its cytoprotective properties favors also slightly faster maturation.

The Erythropoietin-Derived Peptide hA-10 is a Survival Factor for NSCs

As the peptide hA-10 seemed to have a weak effect on cell survival in the first experiments we repeated this survival setup (Experimental Design 1) with growing concentrations of peptide hA-10 from 0 pM to 100,000 pM. As for hS3 and hEPO we observed significantly enhanced numbers of surviving cells in cultures treated with high concentrations of the peptide hA-10. Surviving rates were more than doubled for 10,000 pM and 100,000 pM hA-10 compared to control cultures (FIG. 27).

We repeated the sphere experiments (Experimental Design 2) with high concentrations hA-10 to answer the question if the peptide would additionally have differentiation properties besides of its cytoprotective effects as hS3. Spheres were grown for 7 days in medium containing 0 pM (co) or 100,000 pM peptide hA-10 before being dissociated into single cell suspensions and differentiation in medium containing low growth factor concentrations. Similar to the hS3-experiments we counted higher cell numbers in cultures treated with hA-10. hA-10 treated sphere cultures contained nearly 50% more cells than control cultures (FIG. 28).

Differentiated cells were fixed after 6 days with 4% paraformaldehyde and stained according to previous experiments for the markers DCX, GFAP and MAP2. In contrast to the hS3 experiments we observed no significant differences in percentages of DCX positive cells between cultures derived from hA-10-treated or untreated spheres. Also in the proportion of DCX-positive, MAP2-positive or DCX-MAP2-doublepositive cells no differenced were detected (FIGS. 29A and B).

Bone Marrow Cell Assays (FIG. 30A and FIG. 30B)

Bone marrow cells were harvested from tibia and femur of male C57BL/6 mice (8-11 weeks) and resuspended in a-medium (supplemented with 10% fetal calf serum GOLD, 1% penicillium/streptavidine and 1% L-glutamine). Effects of erythropoietin variants on murine bone marrow cells were tested using two different approaches. We tested on one hand the differentiation capacities of vEPOs in combination with IL-6 or IL-6 and SCF (FIG. 30A) and on the other hand the ability of vEPOs as survival factor in growth factor deprived bone marrow cultures (FIG. 30B).

To test for survival capacities of EPO variants, primary bone marrow cells were cultivated in presence of 100 ng/ml or 10 U/ml vEPOs but absence of additional cytokines at a density of 1 Mio cells/ml in Alphamedium. After 48 h floating cells were harvested and seeded in growth-factor-containing Methocult 03534 methylcellulose (mSCF, mIL-3, hIL-6) at a density of 20,000 cells per assay for the 2 days survival assay. For the five days survival assay cells were fed at DIV2 and harvested at DIV5 for seeding in methylcellulose. In both experimental setups colonies were evaluated after 7 days using an inverted microscope at 2.5× magnification. For the post-survival cfu-e assay floating cells were harvested and seeded at a density of 220,000 cells in methylcellulose containing 200 U/l rhEPO (Roche).

For the differentiation assay we evaluated the erythroid colony forming units (cfu-e) after 48 h, the other colony forming units including cfu-M, cfu-G and cfu-GM were quantified after 7 days.

In this set of experiments freshly prepared bone marrow cells were seeded in 12 well plates (10,000 cells/dish) containing 8 parts Metho Cult SF 3236 methyl cellulose (StemCell Technologie Inc) 1 part cells and 2 parts a-medium containing 100 ng/ml vEPOs (or 10 U/ml hEPO) and 20 ng/ml IL-3 or 20 ng/ml IL-3 and 50 ng/ml SCF respectively. Erythroid Colony forming units were evaluated after 48 h; other colony forming units were evaluated after 7 days.

vEPO Effects on Hematopoietic Stem and Progenitor Cells from Murine Bone Marrow (HSCs)

In analogy to the neural stem cells, we wanted to test two different aspects on the bone-marrow-derived hematopoietic stem cells: differentiation capacities and pro-survival effects of the vEPOs on this diverse cell population (FIG. 30).

In the erythropoiesis experiments we had not observed any differentiation effects of the vEPOs alone apart from the formation of cfu-e in the presence of mEPO and hEPO. These assays were performed in complete absence of additional cytokines therefore we wanted to repeat these experiments in presence of IL-3 or IL-3 and SCF, as many cytokines are unable to mediate effects independently.

Freshly prepared murine bone marrow was plated at low density in presence of vEPOs and additional cytokines. Plates were evaluated after 48 h for cfu-e formation and after 7 days for general colony formation including mainly cfu-Gs, cfu-GMs and cfu-Ms.

As expected from erythropoiesis experiments we observed significant formation of cfu-e only in hEPO containing conditions. We counted formation of approximately 10 colonies per 10,000 plated cells in presence of IL3 and approximately 8 colonies per 10,000 cells in presence of IL-3 and SCF (stem cell factor). Very few cfu-es were observed in presence of high concentrations of hA-10 plates reaching not statistically significance (FIGS. 31A+B).

In respect to numbers and types of colonies evaluated at day 7 after plating we observed no differences in the tested conditions (FIGS. 31C+D). Colonies were mainly identified as cfu-GM (granulocyte-macrophage colonies) or cfu-G (granulocyte colonies) from shape and size of the single cells. Additional identification strategies were not performed. From these experiments we conclude the vEPOs not to have differentiation effects in combination with IL-3 or Il-3 and SCF apart from the erythropoiesis-stimulating activity of hEPO.

To test for cytoprotective or pro-survival features on the heterogeneous hematopoietic cell population we cultivated freshly prepared bone marrow cells in absence of cytokines but in presence of 100 ng/ml hEPO, 100 ng/ml hS3 or 100 nM hA-10 peptide. Hematopoietic stem cells are cytokine-dependent, a shortage of cytokines results in death of these cells.

After two days in culture the floating cells containing the hematopoietic stem cell population were harvested and seeded at low density on methylcellulose containing Il-3, IL-6 and SCF, factors needed for the formation of cfu-G, cfu-M and cfu-GM. Cell o numbers of harvested cells did not differentiate significantly between the treatment conditions. (FIG. 33A)

After 7 days we evaluated the number of formed colonies that we identified mainly as cfu-G and some cfu-GM. We observed significant higher numbers of colonies in dishes seeded with hematopoietic progenitor cells grown for two days in vEPO containing medium. In plates containing untreated bone marrow (MOCK) we observed the formation of 38 colonies in the mean, whereas in plates seeded with vEPO-pretreated bone marrow we observed the formation of approximately 55 colonies. In between the different vEPO conditions hEPO, hS3 and peptide hA-10 we did not observe significant differences concerning colony numbers; hEPO treatment was eventually slightly less effective than treatment with the smaller vEPOs (FIG. 33B). Concerning the type of colonies we observed no differences between the treatment groups. Colonies were mainly identified as cfu-GM (granulocyte-macrophage colonies) or cfu-G (granulocyte colonies) from shape and size of the single cells. Additional identification strategies were also not performed.

For the size of the colonies we observed indeed differences. In general colonies formed in plates seeded with hEPO, hS3 or hA-10 pretreated cells grew larger in size than on control plates (FIG. 32). This finding correlates with the finding of higher colony numbers after vEPO treatment and can be interpreted as an improved conservation of colony forming capacities of hematopoietic stem cells grown in absence of cytokines but in presence of vEPOs.

Having found cytoprotective features of the vEPOs in this surviving model we wanted to test how pronounced these features were and repeated the same experimental setup with a starving period of 5 days. After 5 days in medium free from SCF, IL-3 and IL-6 floating cells in the different conditions were harvested and cell numbers were evaluated as normalized numbers towards the control condition MOCK. We found significantly more cells in hEPO-treated cultures, that we supposed to be erythroblasts surviving in presence of hEPO but not in the non-erythropoietic hS3-, hA-10- and MOCK-environments (FIG. 35A).

Again 20.000 cells were plated per 2 ml methylcellulose and formed colonies were evaluated after 7 days. As in the former experiments we found higher colony-forming rates for cultures grown in vEPOs compared to MOCK-treated cultures. Interestingly the peptide hA-10 performed much better in this setup than hS3 and hEPO. We counted nearly 50% more colonies in the hA-10-dishes than in hS3-dishes and hEPO-dishes and more than the double of colonies compared to control dishes (FIG. 35B). Again no differences in the type of colonies were observed between the conditions whereas colonies grown from hA-10-cultures were in average greater in size and density. The colonies identified in MOCK conditions were comparably much smaller and less dense than in the vEPO conditions (FIG. 34).

When plating cells after the starving period on growthfactor-free methylcellulose supplemented with 200 U/l rhEPO we observed emergence of colony-forming units only on plates seeded with cells previously grown in hEPO-containing medium. This finding supports the previous hypothesis that higher cell numbers counted after the starving period in hEPO-conditions are due to survival of erythroblasts (FIG. 35C).

Murine Mesenchymal (Stromal) Stem and Progenitor Cells (mMSCs)

Murine MSCs were obtained from Tulane University (T-mMSC). Stem cells were cultivated as low density cultures (50 cells/cm$^2$) in Alphamedium supplemented with 10% Serum Supreme, 10% horse serum (HS) and 1% L-glutamine.

For experiments, cells were lifted by trypsination and seeded at low density (50 cells/cm$^2$) in medium containing 20% serum (serum-containing condition) or 0.5% serum (low serum-condition) in presence or absence (MOCK) of vEPOs. Colonies were stained at day 6 for serum-containing conditions and at day 8 for low-serum conditions with crystalviolett (3% in methanol) for 10 min at RT. For evaluation only colonies of defined size (equal or >1 mm$^2$ diameter) were taken into account.

For the feeding experiment, cells were lifted and seeded as described previously in medium containing 0.5% serum in presence or absence of 100 nM hA-10. Medium was completely exchanged after 2 days to fresh medium containing 0.5% serum with or without 100 nM hA-10. Colonies were stained at day 8 with crystalviolett (3% in methanol) for 10 min at RT. For evaluation only colonies of defined size (equal or >1 mm$^2$ diameter) were taken into account.

vEPO Effects on mMSCs

Murine MSCs were grown either in high (20% serum) or in low (0.05% serum) serum conditions in presence or absence of vEPOs at low cell densities. When colonies reached confluence, dishes were stained with crystal violet and numbers of colonies of defined minimal sizes were evaluated in each condition (FIG. 36).

In low-serum conditions we observed significantly higher numbers of colonies when cells were grown in presence of 100 ng/ml hS3. Number of colonies was nearly doubled compared to control cultures (MOCK-medium). HEPO and hA-10 treatment showed no effect. In conditions containing 20% serum, no differences were observed between treatment groups.

In feeding experiments, we observed also survival effects of the peptide hA-10. Numbers of colonies in treated wells (hA-10) were doubled compared to control wells (co) (FIG. 37).

The invention claimed is:

1. A method of cell culture, comprising the steps of
(i) obtaining a stem or progenitor cell sample,
(ii) culturing the stem or progenitor cell sample in media and under closed conditions appropriate to cause proliferation or differentiation of the stem or progenitor cells, and
(iii) optionally purifying the stem or progenitor cells ex vivo, wherein the media comprises a vEPO protein variant selected from the group consisting of:
(a) proteins termed hs3, h1-4, h1-5, hs4, h1-I, h2-1, mS, mG3, mG5, m301 and mK3 having the deduced amino acid sequence of SEQ ID NOs 2, 4, 6, 8, 10, 12, 14, 16, 18, 20, and 22, respectively;
(b) proteins encoded by polynucleotides having the coding sequence as of SEQ ID NOs: 1, 3, 5, 7, 9, 11, 13, 15, 17, 19, and 21 encoding at least the mature form of the protein;
(c) proteins encoded by a polynucleotide encoding a humanized version of the proteins mS, mG3, mG5, m301 and mK3 having the deduced amino acid sequence of SEQ ID NOs 14, 16, 18, 20, and 22;
(d) a protein comprising a fusion of an amino acid sequence selected from the group of amino acid sequences of SEQ ID NO 24, 26, 28, and 30, at the N-terminus of an amino acid sequence selected from the group of amino acid sequences of SEQ ID NO 32, 34, 36, and 38;
(e) a protein encoded by a polynucleotide comprising a fusion of polynucleotide sequences selected from the group of polynucleotide sequences of SEQ ID NO 23, 25, 27, and 29, 5' of a polynucleotide sequence selected from the group of polynucleotide sequences of SEQ ID NO 31, 33, 35, and 37;
(f) a derivative of a protein or a peptide encoded by a polynucleotide of anyone of (a) to (e), wherein in said derivative between 1 and 10 amino acid residues are conservatively substituted compared to said protein, and said derivative has neuroprotective activity, but essentially no hematopoietic activity;
(g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has neuroprotective activity, but essentially no hematopoietic activity;
(h) a protein termed ha, hAmA, hAmE, hA-10 and hA-10-transport, hA-transport sequence, having the deduced amino acid sequence of SEQ ID NOs 50, 51, 52, 53, 61 and 66 respectively;
(i) a protein encoded by a polynucleotide having the coding sequence of SEQ ID NOs: 55, 56, 57, 58, 60 and 65 encoding at least the mature form of the protein;
(j) a derivative of a protein termed ha, hAmA, hAmE and hA-10, or a protein encoded by a polynucleotide having the coding sequence of SEQ ID NOs: 55, 56, 57 and 58 encoding at least the mature form of the protein, wherein in said derivative between 1 and 10 amino acid residues are conservatively substituted compared to said protein, and said derivative has neuroprotective activity, but essentially no hematopoietic activity;
(k) a fragment of a protein termed ha, hAmA, hAmE and hA-10, or a protein encoded by a polynucleotide having the coding sequence of SEQ ID NOs: 55, 56, 57 and 58 encoding at least the mature form of the protein, wherein in said fragment between 1 and 10 amino acid residues are N- and/or C-terminally deleted and/or between 1 and 10 amino acids are deleted N- and or C-terminally of the junction compared to said protein, and said fragment has neuroprotective activity, but essentially no hematopoietic activity;
(l) an erythropoietin (EPO) variant encoded by a polynucleotide selected from the group consisting of:
 (1) polynucleotides encoding the N-terminal part of full length EPO including helix A and which lack at least one of the following:
  (i) a fragment of at least 10 amino acids between helix A and helix B,
  (ii) a fragment of at least 10 amino acids of helix B,
  (iii) a fragment of at least 2 amino acids between helix B and helix C,
  (iv) a fragment of at least 10 amino acids of helix C,
  (v) a fragment of at least 10 amino acids between helix C and D, and/or
  (vi) a fragment of at least 10 amino acids of helix D, wherein said variant has neuroprotective activity, but essentially no hematopoietic activity,
 (2) polynucleotides encoding a derivative of a protein encoded by a polynucleotide of anyone of (a), wherein in said derivative between 1 and 10 amino acid residues are conservatively substituted compared to said protein, and said derivative has neuroprotective activity, but essentially no hematopoietic activity and,
 (3) polynucleotides, the complementary strand of which hybridizes under stringent conditions to a polynucleotide as defined in (1) and which code for a protein having neuroprotective activity, but essentially no hematopoietic activity; or the complementary strand of such a polynucleotide;
(m) a derivative of a protein of anyone of (a) to (l), wherein in said derivative amino acid residues are truncated from the transport sequence (SEQ ID NO 62 for amino acid sequence and SEQ ID NO 63 for polynucleotide sequence), and said derivative has neuroprotective activity, but essentially no hematopoietic activity.

2. Method according to claim 1, wherein the stem cell is an embryonic, fetal or adult (postnatal-derived) stem cell selected from the group of totipotent stem cells, pluripotent stem cells, multipotent stem cells, unipotent stem cells and reprogrammed somatic cells with the capacity to self-renew and to give rise to various differentiated progeny.

3. Method according to claim 2, wherein the totipotent and the pluripotent stem cell is selected from the group of embryonic stem cells, embryonic germ cells and embryonal carcinoma cells, germline stem cells, including spermatogonial stem cells, or from cloned cells or from fused or in vitro reprogrammed cells.

4. Method according to claim 2, wherein the multipotent stem cell and progenitor cell is selected from the group of fetal or adult stem and progenitor cells derived from any tissue or from cloned cells or from fused or reprogrammed cells, including but not restricted to hematopoietic stem and progenitor cells, peripheral blood stem and progenitor cells, umbilical cord stem and progenitor cells, endothelial precursor cells, mesenchymal stem and progenitor cells, multipotent adult progenitor cells, neural stem and progenitor cells, glomus cells, epidermal stem and progenitor cells, intestinal stem and progenitor cells, hair follicle stem and progenitor cells, cardiac and skeletal muscle stem and progenitor cells, adipose-derived stem and progenitor cells, hepatic stem and progenitor cells, pancreatic stem and progenitor cells, neoplastic cells.

5. Method according to claim 1, wherein the vEPO protein is an erythropoietin (EPO) variant, which is a homologue of an erythropoietin (EPO) variant from another eukaryotic species.

6. Method according to claim 1, wherein the differentiated cells are segregated from the undifferentiated or less differentiated stem and progenitor cells.

7. Method according to claim 6, wherein the cells are segregated by immunoaffinity separation or dye exclusion.

8. Method according to claims 7, wherein the immunoaffinity separation is performed using a selection element having an antibody or fragment thereof selected from the group of (or homologues): Oct3/4, Nanog, Sox2, Utf1, Esg1, Rex1, FoxD3, Utf1, Tdgf1, LeftB, Lef1, Tcf4, Dsh, Lin28, Dnmt3B, Smoothened, SMO, Gdf3, Gja1, Notch1, Manic Fringe, Tal1, Lmo2, Hox A9, Meis-1, Gcn5, Sirt2, Atrx, TGIF, Enx1, Tal1, Lmo2, Bmi1, Bmp4, Meis1, Lhx2, CyclinD1, CyclinG2, MDR1, Osteopontin, LIFR, AA4.1, CLQR1, IFI16, JAK3, FZD6, StraB, Islet-1, Gata4, Nkx2.5, Mef2c, alpha-MHC, Mlc2v, MyoD, SM alpha-actin, VSM-MHC, Pecam1, Flk1, Flt1, VWF, Nestin, GFAP, Synaptophysin, GAD, Calbindin, TH, TPH, ChAT, VGLUT1, VGLUT2, Drd2, Afp, Krt1-18, Krt1-10, CD45, Ly6C/G, Mac-1, CD19, CD3, CD4, CD8, CD17, CD25, FoxP3, CD11c, CD13, c-Kit, CD34, Sca-1, MHCI, MHCII, CD44, SSEA-1, Ter119, Thy1, CD31, CD62E, CD133, Otx1, Otx2, Pax2, Pax5, Pax6, Doublecortin, class III beta-Tubulin, MAP2, Neurofilament, NeuN, Calretinin, GalC, NG2, Iba1, CD11b, F4/80, CCR2, MBP, MOG.

9. A method of treating an individual with an acute or chronic degenerative, inflammatory or other disorder leading to cell loss and/or tissue dysfunction, wherein the individual is treated with vEPO or cells expressing the vEPO variant from an exogenous nucleic acid encoding a vEPO protein in order to support and enhance regeneration by endogenous stem and progenitor cells populations, wherein the vEPO is selected from the group of:

(a) proteins termed hs3, h1-4, h1-S, hs4, hI-I, h2-1, mS, mG3, mGS, m301 and mK3 having the deduced amino acid sequence of SEQ ID NOs 2, 4, 6, 8, 10, 12, 14, 16, 18, 20, and 22, respectively;
(b) proteins encoded by polynucleotides having the coding sequence of SEQ ID NOs: 1, 3, 5, 7, 9, 11, 13, 15, 17, 19, and 21 encoding at least the mature form of the protein;
(c) proteins encoded by a polynucleotide encoding a humanized version of the proteins mS, mG3, mG5, m301 and mK3 having the deduced amino acid sequence of SEQ ID NOs 14, 16, 18, 20, and 22;
(d) a protein comprising a fusion of an amino acid sequence selected from the group of amino acid sequences as shown in SEQ ID NO 24, 26, 28, and 30, at the N-terminus of an amino acid sequence selected from the group of amino acid sequences of SEQ ID NO 32, 34, 36, and 38;
(e) a protein encoded by a polynucleotide comprising a fusion of polynucleotide sequences selected from the group of polynucleotide sequences of SEQ ID NO 23, 25, 27, and 29, 5' of a polynucleotide sequence selected from the group of polynucleotide sequences of SEQ ID NO 31, 33, 35, and 37;
(f) a derivative of a protein or a peptide encoded by a polynucleotide of anyone of (a) to (e), wherein in said derivative between 1 and 10 amino acid residues are conservatively substituted compared to said protein, and said derivative has neuroprotective activity, but essentially no hematopoietic activity;
(g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has neuroprotective activity, but essentially no hematopoietic activity;
(h) a protein termed ha, hAmA, hAmE, hA-10 and hA-10-transport, hA-transport sequence, having the deduced amino acid sequence of SEQ ID NOs 50, 51, 52, 53, 61 and 66 respectively;
(i) a protein encoded by a polynucleotide having the coding sequence of SEQ ID NOs: 55, 56, 57, 58, 60 and 65 encoding at least the mature form of the protein;
(j) a derivative of a protein termed ha, hAmA, hAmE and hA-10, or a protein encoded by a polynucleotide having the coding sequence of SEQ ID NOs: 55, 56, 57 and 58 encoding at least the mature form of the protein, wherein in said derivative between 1 and 10 amino acid residues are conservatively substituted compared to said protein, and said derivative has neuroprotective activity, but essentially no hematopoietic activity;
(k) a fragment of a protein termed ha, hAmA, hAmE and hA-10, or a protein encoded by a polynucleotide having the coding sequence of SEQ ID NOs: 55, 56, 57 and 58 encoding at least the mature form of the protein, wherein in said fragment between 1 and 10 amino acid residues are N- and/or C-terminally deleted and/or between 1 and 10 amino acids are deleted N- and or C-terminally of the junction compared to said protein, and said fragment has neuroprotective activity, but essentially no hematopoietic activity;
(l) an erythropoietin (EPO) variant encoded by a polynucleotide selected from the group consisting of:
(1) polynucleotides encoding the N-terminal part of full length EPO including helix A and which lack at least one of the following:
(i) a fragment of at least 10 amino acids between helix A and helix B,
(ii) a fragment of at least 10 amino acids of helix B,
(iii) a fragment of at least 2 amino acids between helix B and helix C,
(iv) a fragment of at least 10 amino acids of helix C,
(v) a fragment of at least 10 amino acids between helix C and D, and/or
(vi) a fragment of at least 10 amino acids of helix D, wherein said variant has neuroprotective activity, but essentially no hematopoietic activity,
(2) polynucleotides encoding a derivative of a protein encoded by a polynucleotide of any one of (a), wherein in said derivative between 1 and 10 amino acid residues are conservatively substituted compared to said protein, and said derivative has neuroprotective activity, but essentially no hematopoietic activity and, (3) polynucleotides, the complementary strand of which hybridizes under stringent conditions to a polynucleotide as defined in (1) and which code for a protein having neuroprotective activity, but essentially no hematopoietic activity; or the complementary strand of such a polynucleotide;

(m) a derivative of a protein of anyone of (a) to (l), wherein in said derivative amino acid residues are truncated from the transport sequence, SEQ ID NO 62 for amino acid sequence and SEQ ID NO 63 for polynucleotide sequence, and said derivative has neuroprotective activity, but essentially no hematopoietic activity.

10. A method of treating an individual with an acute or chronic degenerative, inflammatory or other disorder leading to cell loss or tissue dysfunction, wherein the individual is treated by transplanting stem or progenitor cells, wherein i) the stem or progenitor cells are pre-incubated in a cell culture comprising a vEPO protein variant prior to transplantation and/or, ii) the stem or progenitor cells express the vEPO protein variant due to the presence of an exogenous copy of a nucleic acid encoding a vEPO protein and/or, iii) the stem or progenitor cells are transplanted and the vEPO protein variant is administered shortly before the transplant, shortly after the transplant or together with the transplant, wherein the vEPO protein variant is selected from the group consisting of:

(a) proteins termed hs3, h1-4, h1-5, hs4, h1-1, h2-1, mS, mG3, mG5, m301 and mK3 having the deduced amino acid sequence of SEQ ID NOs 2, 4, 6, 8, 10, 12, 14, 16, 18, 20, and 22, respectively;

(b) proteins encoded by polynucleotides having the coding sequence of SEQ ID NOs: 1, 3, 5, 7, 9, 11, 13, 15, 17, 19, and 21 encoding at least the mature form of the protein;

(c) proteins encoded by a polynucleotide encoding a humanized version of the proteins mS, mG3, mG5, m301 and mK3 having the deduced amino acid sequence of SEQ ID NOs 4, 16, 18, 20, and 22;

(d) a protein comprising a fusion of an amino acid sequence selected from the group of amino acid sequences of SEQ ID NO 24, 26, 28, and 30, at the N-terminus of an amino acid sequence selected from the group of amino acid sequences of SEQ ID NO 32, 34, 36, and 38;

(e) a protein encoded by a polynucleotide comprising a fusion of polynucleotide sequences selected from the group of polynucleotide sequences of SEQ ID NO 23, 25, 27, and 29, 5' of a polynucleotide sequence selected from the group of polynucleotide sequences of SEQ ID NO 31, 33, 35, and 37;

(f) a derivative of a protein or a peptide encoded by a polynucleotide of anyone of (a) to (e), wherein in said derivative between 1 and 10 amino acid residues are conservatively substituted compared to said protein, and said derivative has neuroprotective activity, but essentially no hematopoietic activity;

(g) the protein of (a) to (f), wherein in said fragment between 1 and 10 amino acid residues are N- and/or C-terminally deleted and/or between 1 and 10 amino acids are deleted N- and or C-terminally of the junction compared to said protein, and said fragment has neuroprotective activity, but essentially no hematopoietic activity;

(h) a protein termed ha, hAmA, hArnE, hA-10 and hA-10-transport, hA-transport sequence, having the deduced amino acid sequence of SEQ ID NOs 50, 51, 52, 53, 61 and 66 respectively;

(i) a protein encoded by a polynucleotide having the coding sequence, as shown in SEQ ID NOs: 55, 56, 57, 58, 60 and 65 encoding at least the mature form of the protein;

(j) a derivative of a protein termed ha, hAmA, hAmE and hA-10, or a protein encoded by a polynucleotide having the coding sequence of SEQ ID NOs: 55, 56, 57 and 58 encoding at least the mature form of the protein, wherein in said derivative between 1 and 10 amino acid residues are conservatively substituted compared to said protein, and said derivative has neuroprotective activity, but essentially no hematopoietic activity;

(k) a fragment of a protein termed ha, hAmA, hAmE and hA-10, or a protein encoded by a polynucleotide having the coding sequence of SEQ ID NOs: 55, 56, 57 and 58 encoding at least the mature form of the protein, wherein in said fragment between 1 and 10 amino acid residues are N- and/or C-terminally deleted and/or between 1 and 10 amino acids are deleted N- and or C-terminally of the junction compared to said protein, and said fragment has neuroprotective activity, but essentially no hematopoietic activity;

(l) an erythropoietin (EPO) variant encoded by a polynucleotide selected from the group consisting of:

(1) polynucleotides encoding the N-terminal part of full length EPO including helix A and which lack at least one of the following:

(i) a fragment of at least 10 amino acids between helix A and helix B, (ii) a fragment of at least 10 amino acids of helix B, (iii) a fragment of at least 2 amino acids between helix B and helix C, (iv) a fragment of at least 10 amino acids of helix C, (v) a fragment of at least 10 amino acids between helix C and D, and/or (vi) a fragment of at least 10 amino acids of helix D, wherein said variant has neuroprotective activity, but essentially no hematopoietic activity, (2) polynucleotides encoding a derivative of a protein encoded by a polynucleotide of anyone of (a), wherein in said derivative between 1 and 10 amino acid residues are conservatively substituted compared to said protein, and said derivative has neuroprotective activity, but essentially no hematopoietic activity and, (3) polynucleotides, the complementary strand of which hybridizes under stringent conditions to a polynucleotide as defined in (1) and which code for a protein having neuroprotective activity, but essentially no hematopoietic activity; or the complementary strand of such a polynucleotide;

(m) a derivative of a protein of anyone of (a) to (l), wherein in said derivative amino acid residues are truncated from the transport sequence, SEQ ID NO 62 for amino acid sequence and SEQ ID NO 63 for polynucleotide sequence, and said derivative has neuroprotective activity, but essentially no hematopoietic activity.

11. Method according to claim 10, wherein said acute or chronic degenerative disorder, inflammatory or other disorder leading to cell loss or tissue dysfunction, is an acute or chronic disorder of the central and peripheral nervous system, sensory organs, skeletal and cardiac muscle, smooth muscle, vasculature, lung, liver, pancreas, upper and lower GI tract, kidneys and urinary tract, prostate, hematopoietic system, immune system, reproductive organs, bone and joints or said condition is associated with an organ or cell transplantation or neoplasia.

* * * * *

SEQUENCE LISTING

<160> NUMBER OF SEQ ID NOS: 81

<210> SEQ ID NO 1
<211> LENGTH: 495
<212> TYPE: DNA
<213> ORGANISM: Homo sapiens

<400> SEQUENCE: 1

```
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacgg tcgggcagca ggccgtagaa     180
gtctggcagg gcctggccct gctgtcggaa gctgtcctgc ggggccaggc cctgttggtc     240
aactcttccc agccgtggga gccctgcag ctgcatgtgg ataaagccgt cagtggcctt      300
cgcagcctca ccactctgct tcgggctctg cgagcccaga aggaagccat ctcccctcca     360
gatgcggcct cagctgctcc actccgaaca atcactgctg cactttccg caaactcttc      420 cgagtctact ccaatttcct ccggggaaag ctgaagctgt acacagggga ggcctgcagg     480
acaggggaca gatga                                                      495
```

<210> SEQ ID NO 2
<211> LENGTH: 164
<212> TYPE: PRT
<213> ORGANISM: Homo sapiens

<400> SEQUENCE: 2

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Val Gly Gln Gln Ala Val Glu Val Trp Gln Gly
    50                  55                  60

Leu Ala Leu Leu Ser Glu Ala Val Leu Arg Gly Gln Ala Leu Leu Val
65                  70                  75                  80

Asn Ser Ser Gln Pro Trp Glu Pro Leu Gln Leu His Val Asp Lys Ala
                85                  90                  95

Val Ser Gly Leu Arg Ser Leu Thr Thr Leu Leu Arg Ala Leu Gly Ala
            100                 105                 110

Gln Lys Glu Ala Ile Ser Pro Pro Asp Ala Ala Ser Ala Ala Pro Leu
        115                 120                 125

Arg Thr Ile Thr Ala Asp Thr Phe Arg Lys Leu Phe Arg Val Tyr Ser
    130                 135                 140

Asn Phe Leu Arg Gly Lys Leu Lys Leu Tyr Thr Gly Glu Ala Cys Arg
145                 150                 155                 160

Thr Gly Asp Arg
```

<210> SEQ ID NO 3
<211> LENGTH: 525
<212> TYPE: DNA
<213> ORGANISM: Homo sapiens

<400> SEQUENCE: 3

```
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
```

| | |
|---|---|
| aggtacctct tggaggccaa ggaggccgag aatatcacga cgggctgtgc tgaacactgc | 180 |
| agcttgaatg agaatatcac tgtcccagac accaaagtta atttctatgc ctggaagagg | 240 |
| atggaggtcg ggcagcaggc cctgttggtc aactcttccc agccgtggga gcccctgcag | 300 |
| ctgcatgtgg ataaagccgt cagtggcctt cgcagcctca ccactctgct tcgggctctg | 360 |
| ggagcccaga aggaagccat ctcccctcca gatgcggcct cagctgctcc actccgaaca | 420 |
| atcactgctg acactttccg caaactcttc cgagtctact ccaatttcct ccggggaaag | 480 |
| ctgaagctgt acacagggga ggcctgcagg acagggaca gatga | 525 |

```
<210> SEQ ID NO 4
<211> LENGTH: 174
<212> TYPE: PRT
<213> ORGANISM: Homo sapiens

<400> SEQUENCE: 4

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
                35                  40                  45

Ala Glu Asn Ile Thr Thr Gly Cys Ala Glu His Cys Ser Leu Asn Glu
            50                  55                  60

Asn Ile Thr Val Pro Asp Thr Lys Val Asn Phe Tyr Ala Trp Lys Arg
65                  70                  75                  80

Met Glu Val Gly Gln Gln Ala Leu Leu Val Asn Ser Ser Gln Pro Trp
                85                  90                  95

Glu Pro Leu Gln Leu His Val Asp Lys Ala Val Ser Gly Leu Arg Ser
                100                 105                 110

Leu Thr Thr Leu Leu Arg Ala Leu Gly Ala Gln Lys Glu Ala Ile Ser
            115                 120                 125

Pro Pro Asp Ala Ala Ser Ala Ala Pro Leu Arg Thr Ile Thr Ala Asp
            130                 135                 140

Thr Phe Arg Lys Leu Phe Arg Val Tyr Ser Asn Phe Leu Arg Gly Lys
145                 150                 155                 160

Leu Lys Leu Tyr Thr Gly Glu Ala Cys Arg Thr Gly Asp Arg
                165                 170

<210> SEQ ID NO 5
<211> LENGTH: 495
<212> TYPE: DNA
<213> ORGANISM: Homo sapiens

<400> SEQUENCE: 5
```

| | |
|---|---|
| atgggggtgc acgaatgtcc tgcctggctg tggcttctcc tgtccctgct gtcgctccct | 60 |
| ctgggcctcc cagtcctggg cgccccacca cgcctcatct gtgacagccg agtcctggag | 120 |
| aggtacctct tggaggccaa ggaggccgag aatatcacga cgggctgtgc tgaacactgc | 180 |
| agcttgaatg agaatatcac tgtcccagac accaaagtta atttctatgc cctgttggtc | 240 |
| aactcttccc agccgtggga gcccctgcag ctgcatgtgg ataaagccgt cagtggcctt | 300 |
| cgcagcctca ccactctgct tcgggctctg gagcccaga aggaagccat ctcccctcca | 360 |
| gatgcggcct cagctgctcc actccgaaca atcactgctg acactttccg caaactcttc | 420 |
| cgagtctact ccaatttcct ccggggaaag ctgaagctgt acacagggga ggcctgcagg | 480 | acaggggaca gatga 495

<210> SEQ ID NO 6
<211> LENGTH: 164
<212> TYPE: PRT
<213> ORGANISM: Homo sapiens

<400> SEQUENCE: 6

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Leu Leu Val
65                  70                  75                  80

Asn Ser Ser Gln Pro Trp Glu Pro Leu Gln Leu His Val Asp Lys Ala
                85                  90                  95

Val Ser Gly Leu Arg Ser Leu Thr Thr Leu Leu Arg Ala Leu Gly Ala
            100                 105                 110

Gln Lys Glu Ala Ile Ser Pro Pro Asp Ala Ala Ser Ala Ala Pro Leu
        115                 120                 125

Arg Thr Ile Thr Ala Asp Thr Phe Arg Lys Leu Phe Arg Val Tyr Ser
    130                 135                 140

Asn Phe Leu Arg Gly Lys Leu Lys Leu Tyr Thr Gly Glu Ala Cys Arg
145                 150                 155                 160

Thr Gly Asp Arg

<210> SEQ ID NO 7
<211> LENGTH: 489
<212> TYPE: DNA
<213> ORGANISM: Homo sapiens

<400> SEQUENCE: 7
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggagccgt gggagcccct gcagctgcat gtggataaag ccgtcagtgg ccttcgcagc     300
ctcaccactc tgcttcgggc tctgggagcc agaaggaag ccatctcccc tccagatgcg     360
gcctcagctg ctccactccg aacaatcact gctgacactt ccgcaaaact cttccgagtc     420
tactccaatt tcctccgggg aaagctgaag ctgtacacag ggaggcctg caggacaggg     480
gacagatga                                                             489

<210> SEQ ID NO 8
<211> LENGTH: 162
<212> TYPE: PRT
<213> ORGANISM: Homo sapiens

<400> SEQUENCE: 8

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Pro Trp Glu Pro Leu Gln Leu His Val Asp Lys Ala Val Ser
                 85                  90                  95

Gly Leu Arg Ser Leu Thr Thr Leu Leu Arg Ala Leu Gly Ala Gln Lys
            100                 105                 110

Glu Ala Ile Ser Pro Pro Asp Ala Ala Ser Ala Ala Pro Leu Arg Thr
            115                 120                 125

Ile Thr Ala Asp Thr Phe Arg Lys Leu Phe Arg Val Tyr Ser Asn Phe
130                 135                 140

Leu Arg Gly Lys Leu Lys Leu Tyr Thr Gly Glu Ala Cys Arg Thr Gly
145                 150                 155                 160

Asp Arg

<210> SEQ ID NO 9
<211> LENGTH: 475
<212> TYPE: DNA
<213> ORGANISM: Homo sapiens

<400> SEQUENCE: 9
atgggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccaggc cctgttggtc aactcttccc agccgtggga   240
gcccctgcag ctgcatgtgg ataaagccgt cagtggcctt cgcagcctca ccactctgct   300 tcgggtctg ggagcccaga aggaagccat ctcccctcca gatgcggcct cagctgctcc   360
actccgaaca atcactgctg acactttccg caaactcttc cgagtctact ccaatttcct   420
ccggggaaag ctgaagctgt acacagggga ggcctgcagg acagggaca gatga          475

<210> SEQ ID NO 10
<211> LENGTH: 87
<212> TYPE: PRT
<213> ORGANISM: Homo sapiens

<400> SEQUENCE: 10

Met Gly Val His Glu Cys Pro Ala Trp Leu Trp Leu Leu Leu Ser Leu
1               5                  10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
 50                  55                  60

Asn Ile Thr Val Pro Gly Pro Val Gly Gln Leu Phe Pro Ala Val Gly
 65                  70                  75                  80

Ala Pro Ala Ala Ala Cys Gly
                 85

<210> SEQ ID NO 11
<211> LENGTH: 301
<212> TYPE: DNA
<213> ORGANISM: Homo sapiens

<400> SEQUENCE: 11

```
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaacaatca ctgctgacac tttccgcaaa ctcttccgag tctactccaa     240
tttcctccgg ggaaagctga agctgtacac aggggaggcc tgcaggacag ggacagatg      300
a                                                                    301
```

<210> SEQ ID NO 12
<211> LENGTH: 68
<212> TYPE: PRT
<213> ORGANISM: Homo sapiens

<400> SEQUENCE: 12

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Asn His Cys
65

<210> SEQ ID NO 13
<211> LENGTH: 399
<212> TYPE: DNA
<213> ORGANISM: Mus musculus

<400> SEQUENCE: 13

```
atgggggtgc ccgaacgtcc caccctgctg cttttactct ccttgctact gattcctctg      60
ggcctcccag tcctctgtgc tccccacgc ctcatctgcg acagtcgagt tctggagagg      120
tacatcttag aggccaagga ggcagaaaat gtcacgatgg ttgtgcaga aggtcccaga      180
ctgagtgaaa atattacagt cccagatacc aaagtcaact tctatgcttg gaaaagaatg     240
gagaaggaat tgatgtcgcc tcagatacc accccacctg ctccactccg aacactcaca     300
gtggatactt tctgcaagct cttccgggtc tacgccaact tcctccgggg gaaactgaag     360
ctgtacacgg gagaggtctg caggagaggg acaggtga                            399
```

<210> SEQ ID NO 14
<211> LENGTH: 132
<212> TYPE: PRT
<213> ORGANISM: Mus musculus

<400> SEQUENCE: 14

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Pro Arg Leu Ile
            20                  25                  30

```
Cys Asp Ser Arg Val Leu Glu Arg Tyr Ile Leu Glu Ala Lys Glu Ala
            35                  40                  45

Glu Asn Val Thr Met Gly Cys Ala Glu Gly Pro Arg Leu Ser Glu Asn
 50                  55                  60

Ile Thr Val Pro Asp Thr Lys Val Asn Phe Tyr Ala Trp Lys Arg Met
 65                  70                  75                  80

Glu Lys Glu Leu Met Ser Pro Pro Asp Thr Thr Pro Ala Pro Leu
                 85                  90                  95

Arg Thr Leu Thr Val Asp Thr Phe Cys Lys Leu Phe Arg Val Tyr Ala
            100                 105                 110

Asn Phe Leu Arg Gly Lys Leu Lys Leu Tyr Thr Gly Glu Val Cys Arg
            115                 120                 125

Arg Gly Asp Arg
        130

<210> SEQ ID NO 15
<211> LENGTH: 387
<212> TYPE: DNA
<213> ORGANISM: Mus musculus

<400> SEQUENCE: 15
atgggggtgc cgaacgtcc caccctgctg cttttactct ccttgctact gattcctctg      60
ggcctcccag tcctctgtgc tcccccacgc ctcatctgcg acagtcgagt tctggagagg    120
tacatcttag aggccaagga ggcagaaaat gtcacgatgg gttgtgcaga aggtcccaga    180
ctgagtgaaa atattacagt cccagatacc aaagtcaact tctatgcttg gaaaagaatg    240
gaggtggaag aacaggccat agaagtttgg caaggcctgt ccctgctctc agaagccatc    300
ctgcaggccc aggccctgct agccaacttc ctccggggga aactgaagct gtacacggga    360
gaggtctgca ggagagggga caggtga                                        387

<210> SEQ ID NO 16
<211> LENGTH: 128
<212> TYPE: PRT
<213> ORGANISM: Mus musculus

<400> SEQUENCE: 16

Met Gly Val Pro Glu Arg Pro Thr Leu Leu Leu Leu Ser Leu Leu
 1               5                  10                  15

Leu Ile Pro Leu Gly Leu Pro Val Leu Cys Ala Pro Pro Arg Leu Ile
             20                  25                  30

Cys Asp Ser Arg Val Leu Glu Arg Tyr Ile Leu Glu Ala Lys Glu Ala
            35                  40                  45

Glu Asn Val Thr Met Gly Cys Ala Glu Gly Pro Arg Leu Ser Glu Asn
 50                  55                  60

Ile Thr Val Pro Asp Thr Lys Val Asn Phe Tyr Ala Trp Lys Arg Met
 65                  70                  75                  80

Glu Val Glu Glu Gln Ala Ile Glu Val Trp Gln Gly Leu Ser Leu Leu
                 85                  90                  95

Ser Glu Ala Ile Leu Gln Ala Gln Ala Leu Leu Ala Asn Phe Leu Arg
            100                 105                 110

Gly Lys Leu Lys Leu Tyr Thr Gly Glu Val Cys Arg Arg Gly Asp Arg
            115                 120                 125

<210> SEQ ID NO 17
<211> LENGTH: 513
```

<212> TYPE: DNA
<213> ORGANISM: Mus musculus

<400> SEQUENCE: 17

```
atgggggtgc ccgaacgtcc caccctgctg cttttactct ccttgctact gattcctctg     60
ggcctcccag tcctctgtgc tcccccacgc ctcatctgcg acagtcgagt tctggagagg    120
tacatcttag aggccaagga ggcagaaaat gtcacgatgg gttgtgcaga aggtcccaga    180
ctgagtgaaa atattacagt cccagatacc aaagtcaact tctatgcttg aaaagaatg     240
gaggtggaag aacaggccat agaagtttgg caaggcctgt ccctgctctc agaagccatc    300
ctgcaggccc aggccctgct agccaattcc tcccagccac cagagaccct tcagcttcat    360
atagacaaag ccatcagtgg tctacgtagc ctcacttcac tgcttcgggt actgggagct    420
cagaaggaat tgatgtcgcc tccagatacc accccacctg ctccactccg aacactcaca    480
gtggatactt tctgcaggag aggggacagg tga                                 513
```

<210> SEQ ID NO 18
<211> LENGTH: 170
<212> TYPE: PRT
<213> ORGANISM: Mus musculus

<400> SEQUENCE: 18

```
Met Gly Val Pro Glu Arg Pro Thr Leu Leu Leu Leu Ser Leu Leu
1               5                  10                  15

Leu Ile Pro Leu Gly Leu Pro Val Leu Cys Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn Ser Ser Gln
            100                 105                 110

Pro Pro Glu Thr Leu Gln Leu His Ile Asp Lys Ala Ile Ser Gly Leu
        115                 120                 125

Arg Ser Leu Thr Ser Leu Leu Arg Val Leu Gly Ala Gln Lys Glu Leu
    130                 135                 140

Met Ser Pro Pro Asp Thr Thr Pro Pro Ala Pro Leu Arg Thr Leu Thr
145                 150                 155                 160

Val Asp Thr Phe Cys Arg Arg Gly Asp Arg
                165                 170
```

<210> SEQ ID NO 19
<211> LENGTH: 279
<212> TYPE: DNA
<213> ORGANISM: Mus musculus

<400> SEQUENCE: 19

```
atgggggtgc ccgaacgtcc caccctgctg cttttactct ccttgctact gattcctctg     60
ggcctcccag tcctctgtgc tcccccacgc ctcatctgcg acagtcgagt tctggagagg    120
tacatcttag aggccaagga ggcagaaaat gtcacgatgg gttgtgcaga aggtcccaga    180
ctgagtgaaa atattacagt cccagatacc aaagtcaact tcctccgggg gaaactgaag    240
```
ctgtacacgg gagaggtctg caggagaggg gacaggtga    279

<210> SEQ ID NO 20
<211> LENGTH: 92
<212> TYPE: PRT
<213> ORGANISM: Mus musculus

<400> SEQUENCE: 20

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Pro Arg Leu Ile
        20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Leu Arg Gly Lys Leu Lys
65                  70                  75                  80

Leu Tyr Thr Gly Glu Val Cys Arg Arg Gly Asp Arg
                85                  90

<210> SEQ ID NO 21
<211> LENGTH: 591
<212> TYPE: DNA
<213> ORGANISM: Mus musculus

<400> SEQUENCE: 21
atgggggtgc ccgaacgtcc caccctgctg cttttactct ccttgctact gattcctctg    60
ggcctcccag tcctctgtgc tcccccacgc ctcatctgcg acagtcgagt tctggagagg   120
tacatcttag aggccaagga ggcagaaaat gtcacgatgg gttgtgcaga aggtcccaga   180
ctgagtgaaa atattacagt cccagatacc aaagtcaact tctatgcttg aaaagaatg    240
gaggtggaag aacaggccat agaagtttgg caaggcctgt ccctgctctc agaagctgta   300
cacgggagag tctgcaggag aggggacag gtgacatgct gctgccaccg tggtggaccg   360
acgaacttgc tccccgtcac tgtgtcatgc caaccctcca ccactcccaa ccctcatcaa   420
acgggtcatt accttcttac cagtctgtcc catggacact ccagcaccag cagtgacatc   480
ctcgggccca agaaacttc ccagagctcc attctgaaat ctaaagatgt cgctggacaa    540
gcccgaggcc cagagaaga gagcctcag aatcagctcg gatttgttta g              591

<210> SEQ ID NO 22
<211> LENGTH: 196
<212> TYPE: PRT
<213> ORGANISM: Mus musculus

<400> SEQUENCE: 22

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Pro Arg Leu Ile
        20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Val His Gly Arg Gly Leu Gln Glu Arg Gly Gln Val Thr
            100                 105                 110

Cys Cys Cys His Arg Gly Gly Pro Thr Asn Leu Leu Pro Val Thr Val
        115                 120                 125

Ser Cys Gln Pro Ser Thr Thr Pro Asn Pro His Gln Thr Gly His Tyr
130                 135                 140

Leu Leu Thr Ser Leu Ser His Gly His Ser Ser Thr Ser Ser Asp Ile
145                 150                 155                 160

Leu Gly Ala Arg Arg Thr Ser Gln Ser Ser Ile Leu Lys Ser Lys Asp
                165                 170                 175

Val Ala Gly Gln Ala Arg Gly Pro Arg Glu Glu Glu Pro Gln Asn Gln
            180                 185                 190

Leu Gly Phe Val
        195

<210> SEQ ID NO 23
<211> LENGTH: 159
<212> TYPE: DNA
<213> ORGANISM: Homo sapiens

<400> SEQUENCE: 23
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacg                            159

<210> SEQ ID NO 24
<211> LENGTH: 53
<212> TYPE: PRT
<213> ORGANISM: Homo sapiens

<400> SEQUENCE: 24

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr
    50

<210> SEQ ID NO 25
<211> LENGTH: 225
<212> TYPE: DNA
<213> ORGANISM: Homo sapiens

<400> SEQUENCE: 25
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttc                     225

<210> SEQ ID NO 26
<211> LENGTH: 82
<212> TYPE: PRT

<213> ORGANISM: Homo sapiens

<400> SEQUENCE: 26

```
Met Gly Val His Glu Cys Pro Ala Trp Leu Trp Leu Leu Leu Ser Leu
1               5                   10                  15
Leu Ser Leu Pro Leu Gly Leu Pro Val Leu Gly Ala Pro Pro Arg Leu
                20                  25                  30
Ile Cys Asp Ser Arg Val Leu Glu Arg Tyr Leu Leu Glu Ala Lys Glu
            35                  40                  45
Ala Glu Asn Ile Thr Thr Gly Cys Ala Glu His Cys Ser Leu Asn Glu
        50                  55                  60
Asn Ile Thr Val Pro Asp Thr Lys Val Asn Phe Tyr Ala Trp Lys Arg
65                  70                  75                  80
Met Glu
```

<210> SEQ ID NO 27
<211> LENGTH: 243
<212> TYPE: DNA
<213> ORGANISM: Mus musculus

<400> SEQUENCE: 27

| | |
|---|---:|
| atgggggtgc cgaacgtcc cacctgctg cttttactct ccttgctact gattcctctg | 60 |
| ggcctcccag tcctctgtgc tcccccacgc ctcatctgcg acagtcgagt tctggagagg | 120 |
| tacatcttag aggccaagga ggcagaaaat gtcacgatgg gttgtgcaga aggtcccaga | 180 |
| ctgagtgaaa atattacagt cccagatacc aaagtcaact tctatgcttg gaaaagaatg | 240 |
| gag | 243 |

<210> SEQ ID NO 28
<211> LENGTH: 81
<212> TYPE: PRT
<213> ORGANISM: Mus musculus

<400> SEQUENCE: 28

```
Met Gly Val Pro Glu Arg Pro Thr Leu Leu Leu Leu Ser Leu Leu
1               5                   10                  15
Leu Ile Pro Leu Gly Leu Pro Val Leu Cys Ala Pro Pro Arg Leu Ile
                20                  25                  30
Cys Asp Ser Arg Val Leu Glu Arg Tyr Ile Leu Glu Ala Lys Glu Ala
            35                  40                  45
Glu Asn Val Thr Met Gly Cys Ala Glu Gly Pro Arg Leu Ser Glu Asn
        50                  55                  60
Ile Thr Val Pro Asp Thr Lys Val Asn Phe Tyr Ala Trp Lys Arg Met
65                  70                  75                  80
Glu
```

<210> SEQ ID NO 29
<211> LENGTH: 326
<212> TYPE: DNA
<213> ORGANISM: Mus musculus

<400> SEQUENCE: 29

| | |
|---|---:|
| atgggggtgc cgaacgtcc cacctgctg cttttactct ccttgctact gattcctctg | 60 |
| ggcctcccag tcctctgtgc tcccccacgc ctcatctgcg acagtcgagt tctggagagg | 120 |
| tacatcttag aggccaagga ggcagaaaat gtcacgatgg gttgtgcaga aggtcccaga | 180 |
| ctgagtgaaa atattacagt cccagatacc aaagtcaact tctatgcttg gaaaagaatg | 240 |

```
gaggtggaag aacaggccat agaagtttgg caaggcctgt ccctgctctc agaagccatc    300
ctgcaggccc aggccctgct agccaa                                        326
```

<210> SEQ ID NO 30
<211> LENGTH: 109
<212> TYPE: PRT
<213> ORGANISM: Mus musculus

<400> SEQUENCE: 30

```
Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn
            100                 105
```

<210> SEQ ID NO 31
<211> LENGTH: 336
<212> TYPE: DNA
<213> ORGANISM: Homo sapiens

<400> SEQUENCE: 31

```
gtcgggcagc aggccgtaga agtctggcag ggcctggccc tgctgtcgga agctgtcctg    60
cggggccagg ccctgttggt caactcttcc cagccgtggg agcccctgca gctgcatgtg   120
gataaagccg tcagtggcct tcgcagcctc accactctgc ttcgggctct gggagcccag   180
aaggaagcca tctcccctcc agatgcggcc tcagctgctc cactccgaac aatcactgct   240
gacactttcc gcaaactctt ccgagtctac tccaatttcc tccggggaaa gctgaagctg   300
tacacagggg aggcctgcag gacaggggac agatga                             336
```

<210> SEQ ID NO 32
<211> LENGTH: 111
<212> TYPE: PRT
<213> ORGANISM: Homo sapiens

<400> SEQUENCE: 32

```
Val Gly Gln Gln Ala Val Glu Val Trp Gln Gly Leu Ala Leu Leu Ser
1               5                   10                  15

Glu Ala Val Leu Arg Gly Gln Ala Leu Leu Val Asn Ser Ser Gln Pro
            20                  25                  30

Trp Glu Pro Leu Gln Leu His Val Asp Lys Ala Val Ser Gly Leu Arg
        35                  40                  45

Ser Leu Thr Thr Leu Leu Arg Ala Leu Gly Ala Gln Lys Glu Ala Ile
    50                  55                  60

Ser Pro Pro Asp Ala Ala Ser Ala Ala Pro Leu Arg Thr Ile Thr Ala
65                  70                  75                  80

Asp Thr Phe Arg Lys Leu Phe Arg Val Tyr Ser Asn Phe Leu Arg Gly
                85                  90                  95
```

```
Lys Leu Lys Leu Tyr Thr Gly Glu Ala Cys Arg Thr Gly Asp Arg
            100                 105                 110
```

<210> SEQ ID NO 33
<211> LENGTH: 234
<212> TYPE: DNA
<213> ORGANISM: Homo sapiens

<400> SEQUENCE: 33

```
cccctgcagc tgcatgtgga taaagccgtc agtggccttc gcagcctcac cactctgctt    60
cgggctctgg gagcccagaa ggaagccatc tcccctccag atgcggcctc agctgctcca   120
ctccgaacaa tcactgctga cactttccgc aaactcttcc gagtctactc caatttcctc   180
cggggaaagc tgaagctgta cacaggggag gcctgcagga caggggacag atga         234
```

<210> SEQ ID NO 34
<211> LENGTH: 80
<212> TYPE: PRT
<213> ORGANISM: Homo sapiens

<400> SEQUENCE: 34

```
Pro Trp Glu Pro Leu Gln Leu His Val Asp Lys Ala Val Ser Gly Leu
1               5                   10                  15

Arg Ser Leu Thr Thr Leu Leu Arg Ala Leu Gly Ala Gln Lys Glu Ala
            20                  25                  30

Ile Ser Pro Pro Asp Ala Ala Ser Ala Ala Pro Leu Arg Thr Ile Thr
        35                  40                  45

Ala Asp Thr Phe Arg Lys Leu Phe Arg Val Tyr Ser Asn Phe Leu Arg
    50                  55                  60

Gly Lys Leu Lys Leu Tyr Thr Gly Glu Ala Cys Arg Thr Gly Asp Arg
65                  70                  75                  80
```

<210> SEQ ID NO 35
<211> LENGTH: 156
<212> TYPE: DNA
<213> ORGANISM: Mus musculus

<400> SEQUENCE: 35

```
aaggaattga tgtcgcctcc agataccacc ccacctgctc cactccgaac actcacagtg    60
gatactttct gcaagctctt ccgggtctac gccaacttcc tccggggggaa actgaagctg   120 tacacgggag aggtctgcag gagagggac aggtga                              156
```

<210> SEQ ID NO 36
<211> LENGTH: 51
<212> TYPE: PRT
<213> ORGANISM: Mus musculus

<400> SEQUENCE: 36

```
Lys Glu Leu Met Ser Pro Pro Asp Thr Thr Pro Pro Ala Pro Leu Arg
1               5                   10                  15

Thr Leu Thr Val Asp Thr Phe Cys Lys Leu Phe Arg Val Tyr Ala Asn
            20                  25                  30

Phe Leu Arg Gly Lys Leu Lys Leu Tyr Thr Gly Glu Val Cys Arg Arg
        35                  40                  45

Gly Asp Arg
    50
```

<210> SEQ ID NO 37

```
<211> LENGTH: 61
<212> TYPE: DNA
<213> ORGANISM: Mus musculus

<400> SEQUENCE: 37
cttcctccgg gggaaactga agctgtacac gggagaggtc tgcaggagag gggacaggtg      60
a                                                                     61

<210> SEQ ID NO 38
<211> LENGTH: 19
<212> TYPE: PRT
<213> ORGANISM: Mus musculus

<400> SEQUENCE: 38

Phe Leu Arg Gly Lys Leu Lys Leu Tyr Thr Gly Glu Val Cys Arg Arg
1               5                   10                  15

Gly Asp Arg

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaacttccaa ggatgaagac ttgcagc                                         27

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtggcagcag catgtcacct gtc                                             23

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tatggatcca tgggggtgcc cgaacgtccc ac                                   32

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tatggatcct cacctgtccc ctctcctgca gac                                  33

<210> SEQ ID NO 43
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 43
gtcgtgactg ggaaaaccct ggcg                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agcggataac aatttcacac agga                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45 gatggggtg cacgaatgtc ctgc                                           24

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cacacctggt catctgtccc ctgtc                                         25

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaagaattcc ctgtcccctc tcctgcagac ctc                                33

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tatggatcca tgggggtgca cgaatgtcc                                     29

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agagaattct ctgtcccctg tcctgcag                                           28

<210> SEQ ID NO 50
<211> LENGTH: 53
<212> TYPE: PRT
<213> ORGANISM: Homo sapiens

<400> SEQUENCE: 50

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr
    50

<210> SEQ ID NO 51
<211> LENGTH: 53
<212> TYPE: PRT
<213> ORGANISM: Artificial Sequence
<220> FEATURE:
<223> OTHER INFORMATION: Description of Artificial Sequence: Synthetic
      Homo sapiens point mutation polypeptide

<400> SEQUENCE: 51

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Ala Tyr Leu Leu Glu Ala Lys Glu
        35                  40                  45

Ala Glu Asn Ile Thr
    50

<210> SEQ ID NO 52
<211> LENGTH: 53
<212> TYPE: PRT
<213> ORGANISM: Artificial Sequence
<220> FEATURE:
<223> OTHER INFORMATION: Description of Artificial Sequence: Synthetic
      Homo sapiens point mutation polypeptide

<400> SEQUENCE: 52

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Glu Tyr Leu Leu Glu Ala Lys Glu
        35                  40                  45

Ala Glu Asn Ile Thr
    50

<210> SEQ ID NO 53
<211> LENGTH: 43
<212> TYPE: PRT
<213> ORGANISM: Artificial Sequence

```
<220> FEATURE:
<223> OTHER INFORMATION: Description of Artificial Sequence: Synthetic
      Homo sapiens ha-10 deletion mutant polypeptide

<400> SEQUENCE: 53

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu
        35                  40

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      Homo sapiens hA-20 deletion mutant polypeptide

<400> SEQUENCE: 54

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile

<210> SEQ ID NO 55
<211> LENGTH: 159
<212> TYPE: DNA
<213> ORGANISM: Homo sapiens

<400> SEQUENCE: 55
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacg                            159

<210> SEQ ID NO 56
<211> LENGTH: 159
<212> TYPE: DNA
<213> ORGANISM: Artificial Sequence
<220> FEATURE:
<223> OTHER INFORMATION: Description of Artificial Sequence: Synthetic
      hAmA (Mutant Alanin hWT-EPO Helix A)
      polynucleotide

<400> SEQUENCE: 56
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
gcgtacctct tggaggccaa ggaggccgag aatatcacg                            159

<210> SEQ ID NO 57
<211> LENGTH: 159
<212> TYPE: DNA
<213> ORGANISM: Artificial Sequence
<220> FEATURE:
<223> OTHER INFORMATION: Description of Artificial Sequence: Synthetic
      hAmE (Mutant Glutamic-Acid hWT-EPO Helix A)
      polynucleotide

<400> SEQUENCE: 57
atgggggtgc acgaatgtcc tgcctggctg tggcttctcc tgtccctgct gtcgctccct      60
```

```
ctgggcctcc cagtcctggg cgccccacca cgcctcatct gtgacagccg agtcctggag    120
gagtacctct tggaggccaa ggaggccgag aatatcacg                           159
```

<210> SEQ ID NO 58
<211> LENGTH: 129
<212> TYPE: DNA
<213> ORGANISM: Artificial Sequence
<220> FEATURE:
<223> OTHER INFORMATION: Description of Artificial Sequence: Synthetic
      hA-10 (hWT-EPO Helix A minus 10aa) polynucleotide

<400> SEQUENCE: 58

```
atggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctc                                                           129
```

<210> SEQ ID NO 59
<211> LENGTH: 99
<212> TYPE: DNA
<213> ORGANISM: Artificial Sequence
<220> FEATURE:
<223> OTHER INFORMATION: Description of Artificial Sequence: Synthetic
      hA-20 (hWT-EPO Helix A minus 20aa) oligonucleotide

<400> SEQUENCE: 59

```
atggggtgc acgaatgtcc tgcctggctg tggcttctcc tgtccctgct gtcgctccct    60
ctgggcctcc cagtcctggg cgccccacca cgcctcatc                          99
```

<210> SEQ ID NO 60
<211> LENGTH: 48
<212> TYPE: DNA
<213> ORGANISM: Homo sapiens

<400> SEQUENCE: 60

```
gccccaccac gcctcatctg tgacagccga gtcctggaga ggtacctc                48
```

<210> SEQ ID NO 61
<211> LENGTH: 16
<212> TYPE: PRT
<213> ORGANISM: Homo sapiens

<400> SEQUENCE: 61

```
Ala Pro Pro Arg Leu Ile Cys Asp Ser Arg Val Leu Glu Arg Tyr Leu
1               5                   10                  15
```

<210> SEQ ID NO 62
<211> LENGTH: 27
<212> TYPE: PRT
<213> ORGANISM: Homo sapiens

<400> SEQUENCE: 62

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25
```

<210> SEQ ID NO 63
<211> LENGTH: 81
<212> TYPE: DNA
<213> ORGANISM: Homo sapiens

<400> SEQUENCE: 63

```
atggggtgc acgaatgtcc tgcctggctg tggcttctcc tgtccctgct gtcgctccct    60
ctgggcctcc cagtcctggg c                                             81
```

<210> SEQ ID NO 64
<211> LENGTH: 495
<212> TYPE: DNA
<213> ORGANISM: Homo sapiens

<400> SEQUENCE: 64

```
atggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacgg tcgggcagca ggccgtagaa   180
gtctggcagg gcctggccct gctgtcggaa gctgtcctgc ggggccaggc cctgttggtc   240
aactcttccc agccgtggga gcccctgcag ctgcatgtgg ataaagccgt cagtggcctt   300
cgcagcctca ccactctgct tcgggctctg ggagcccaga aggaagccat ctcccctcca   360
gatgcggcct cagctgctcc actccgaaca atcactgctg cactttccg caaactcttc    420
cgagtctact ccaatttcct ccggggaaag ctgaagctgt acacagggga ggcctgcagg   480
acaggggaca gatga                                                    495
```

<210> SEQ ID NO 65
<211> LENGTH: 78
<212> TYPE: DNA
<213> ORGANISM: Homo sapiens

<400> SEQUENCE: 65

```
gccccaccac gcctcatctg tgacagccga gtcctggaga ggtacctctt ggaggccaag    60
gaggccgaga atatcacg                                                  78
```

<210> SEQ ID NO 66
<211> LENGTH: 26
<212> TYPE: PRT
<213> ORGANISM: Homo sapiens

<400> SEQUENCE: 66

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr
            20                  25
```

<210> SEQ ID NO 67
<211> LENGTH: 8
<212> TYPE: PRT
<213> ORGANISM: Homo sapiens

<400> SEQUENCE: 67

```
Glu Asn Ile Thr Val Gly Gln Gln
1               5
```

<210> SEQ ID NO 68
<211> LENGTH: 8
<212> TYPE: PRT
<213> ORGANISM: Homo sapiens

<400> SEQUENCE: 68

```
Val Gly Gln Gln Ala Leu Leu Val
1               5
```

```
<210> SEQ ID NO 69
<211> LENGTH: 8
<212> TYPE: PRT
<213> ORGANISM: Homo sapiens

<400> SEQUENCE: 69

Val Asn Phe Tyr Ala Leu Leu Val
1               5

<210> SEQ ID NO 70
<211> LENGTH: 8
<212> TYPE: PRT
<213> ORGANISM: Homo sapiens

<400> SEQUENCE: 70

Lys Arg Met Glu Pro Trp Glu Pro
1               5

<210> SEQ ID NO 71
<211> LENGTH: 8
<212> TYPE: PRT
<213> ORGANISM: Homo sapiens

<400> SEQUENCE: 71

Ile Thr Val Pro Gly Pro Val Gly
1               5

<210> SEQ ID NO 72
<211> LENGTH: 7
<212> TYPE: PRT
<213> ORGANISM: Homo sapiens

<400> SEQUENCE: 72

Leu Asn Glu Asn Asn His Cys
1               5

<210> SEQ ID NO 73
<211> LENGTH: 8
<212> TYPE: PRT
<213> ORGANISM: Mus musculus

<400> SEQUENCE: 73

Lys Arg Met Glu Lys Glu Leu Met
1               5

<210> SEQ ID NO 74
<211> LENGTH: 8
<212> TYPE: PRT
<213> ORGANISM: Mus musculus

<400> SEQUENCE: 74

Leu Leu Ala Asn Phe Leu Arg Gly
1               5

<210> SEQ ID NO 75
<211> LENGTH: 8
<212> TYPE: PRT
<213> ORGANISM: Mus musculus

<400> SEQUENCE: 75

Asp Thr Phe Cys Arg Arg Gly Asp
1               5

<210> SEQ ID NO 76
```

```
<211> LENGTH: 8
<212> TYPE: PRT
<213> ORGANISM: Mus musculus

<400> SEQUENCE: 76

Lys Val Asn Phe Leu Arg Gly Lys
1               5

<210> SEQ ID NO 77
<211> LENGTH: 8
<212> TYPE: PRT
<213> ORGANISM: Mus musculus

<400> SEQUENCE: 77

Leu Ser Glu Ala Val His Gly Arg
1               5

<210> SEQ ID NO 78
<211> LENGTH: 579
<212> TYPE: DNA
<213> ORGANISM: Mus musculus

<400> SEQUENCE: 78 atggggtgc  ccgaacgtcc  caccctgctg  cttttactct  ccttgctact  gattcctctg    60
ggcctcccag  tcctctgtgc  tcccccacgc  ctcatctgcg  acagtcgagt  tctggagagg   120
tacatcttag  aggccaagga  ggcagaaaat  gtcacgatgg  gttgtgcaga  aggtcccaga   180
ctgagtgaaa  atattacagt  cccagatacc  aaagtcaact  tctatgcttg  aaaagaatg    240 gaggtggaag  aacaggccat  agaagtttgg  caaggcctgt  ccctgctctc  agaagccatc   300
ctgcaggccc  aggccctgct  agccaattcc  tcccagccac  cagagaccct  tcagcttcat   360
atagacaaag  ccatcagtgg  tctacgtagc  ctcacttcac  tgcttcgggt  actgggagct   420
cagaaggaat  tgatgtcgcc  tccagatacc  accccacctg  ctccactccg  aacactcaca   480
gtggatactt  tctgcaagct  cttccgggtc  tacgccaact  tcctccgggg  gaaactgaag   540
ctgtacacgg  agaggtctg  caggagaggg  acaggtga                             579

<210> SEQ ID NO 79
<211> LENGTH: 582
<212> TYPE: DNA
<213> ORGANISM: Homo sapiens

<400> SEQUENCE: 79 atggggtgc  acgaatgtcc  tgcctggctg  tggcttctcc  tgtccctgct  gtcgctccct    60
ctgggcctcc  cagtcctggg  cgccccacca  cgcctcatct  gtgacagccg  agtcctggag   120
aggtacctct  tggaggccaa  ggaggccgag  aatatcacga  cgggctgtgc  tgaacactgc   180
agcttgaatg  agaatatcac  tgtcccagac  accaaagtta  atttctatgc  ctggaagagg   240
atggaggtcg  ggcagcaggc  cgtagaagtc  tggcagggcc  tggccctgct  gtcggaagct   300
gtcctgcggg  gccaggccct  gttggtcaac  tcttcccagc  cgtgggagcc  cctgcagctg   360
catgtggata  agccgtcag  tggccttcgc  agcctcacca  ctctgcttcg  ggctctgcga   420
gcccagaagg  aagccatctc  ccctccagat  gcggcctcag  ctgctccact  ccgaacaatc   480
actgctgaca  ctttccgcaa  actcttccga  gtctactcca  atttcctccg  ggaaagctg    540 aagctgtaca  caggggaggc  ctgcaggaca  ggggacagat  ga                      582

<210> SEQ ID NO 80
<211> LENGTH: 193
```

```
<212> TYPE: PRT
<213> ORGANISM: Homo sapiens

<400> SEQUENCE: 80

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 81
<211> LENGTH: 192
<212> TYPE: PRT
<213> ORGANISM: Mus musculus

<400> SEQUENCE: 81

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn Ser Ser Gln
            100                 105                 110

Pro Pro Glu Thr Leu Gln Leu His Ile Asp Lys Ala Ile Ser Gly Leu
        115                 120                 125

Arg Ser Leu Thr Ser Leu Leu Arg Val Leu Gly Ala Gln Lys Glu Leu
    130                 135                 140

Met Ser Pro Pro Asp Thr Thr Pro Pro Ala Pro Leu Arg Thr Leu Thr
```

-continued

```
145                 150                 155                 160
Val Asp Thr Phe Cys Lys Leu Phe Arg Val Tyr Ala Asn Phe Leu Arg
                165                 170                 175
Gly Lys Leu Lys Leu Tyr Thr Gly Glu Val Cys Arg Arg Gly Asp Arg
                180                 185                 190
```